(12) United States Patent
Nagalakshmi et al.

(10) Patent No.: US 9,580,463 B2
(45) Date of Patent: Feb. 28, 2017

(54) HEPATITIS C VIRUS INHIBITORS

(71) Applicant: BRISTOL-MYERS SQUIBB COMPANY, Princeton, NJ (US)

(72) Inventors: Pulicharla Nagalakshmi, Bangalore (IN); Kandhasamy Sarkunam, Hosur (IN); Kishore V. Renduchintala, Bangalore (IN); Paul Michael Scola, Glastonbury, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/768,229

(22) PCT Filed: Mar. 3, 2014

(86) PCT No.: PCT/US2014/019810
§ 371 (c)(1),
(2) Date: Aug. 17, 2015

(87) PCT Pub. No.: WO2014/137869
PCT Pub. Date: Sep. 12, 2014

(65) Prior Publication Data
US 2015/0376233 A1    Dec. 31, 2015

Related U.S. Application Data

(60) Provisional application No. 61/774,136, filed on Mar. 7, 2013.

(51) Int. Cl.
| | | |
|---|---|---|
| *A61K 38/06* | (2006.01) | |
| *C07K 5/083* | (2006.01) | |
| *C07K 5/10* | (2006.01) | |
| *C07K 5/103* | (2006.01) | |
| *A61K 45/06* | (2006.01) | |
| *A61K 38/07* | (2006.01) | |

(52) U.S. Cl.
CPC ............. *C07K 5/081* (2013.01); *A61K 38/06* (2013.01); *A61K 45/06* (2013.01); *C07K 5/1002* (2013.01); *C07K 5/1013* (2013.01); *A61K 38/07* (2013.01)

(58) Field of Classification Search
None
See application file for complete search history.

(56) References Cited

U.S. PATENT DOCUMENTS

| | | | |
|---|---|---|---|
| 5,223,432 A | 6/1993 | Wirz et al. | |
| 7,449,479 B2 | 11/2008 | Wang et al. | |
| 7,582,605 B2 | 9/2009 | Moore et al. | |
| 7,601,709 B2 | 10/2009 | Miao et al. | |
| 7,605,126 B2 | 10/2009 | Niu et al. | |
| 7,635,683 B2 | 12/2009 | Gai et al. | |
| 7,915,291 B2 | 3/2011 | Wang et al. | |
| 8,232,246 B2 | 7/2012 | McDaniel et al. | |
| 8,268,776 B2 | 9/2012 | Sun et al. | |
| 8,299,094 B2 | 10/2012 | Wang et al. | |
| 8,309,685 B2 | 11/2012 | Petter et al. | |
| 8,338,606 B2 | 12/2012 | Perrone et al. | |
| 8,415,374 B2 | 4/2013 | Lemm et al. | |
| 8,507,722 B2 | 8/2013 | Wang | |
| 8,710,229 B2 | 4/2014 | Wang et al. | |
| 2005/0209135 A1 | 9/2005 | Busacca et al. | |
| 2006/0199773 A1 | 9/2006 | Sausker et al. | |
| 2006/0257980 A1 | 11/2006 | Li | |
| 2007/0078081 A1 | 4/2007 | Casarez et al. | |
| 2008/0279821 A1 | 11/2008 | Niu et al. | |
| 2013/0302414 A1 | 11/2013 | Perrone | |
| 2014/0235617 A1 | 8/2014 | Gao et al. | |

FOREIGN PATENT DOCUMENTS

| | | |
|---|---|---|
| WO | WO 98/17679 A1 | 4/1998 |
| WO | WO 98/22106 A1 | 5/1998 |
| WO | WO 99/07733 A2 | 2/1999 |
| WO | WO 99/07734 A2 | 2/1999 |
| WO | WO 00/09543 A2 | 2/2000 |

(Continued)

OTHER PUBLICATIONS

Eley, T. et al., "Improved Bioavailability and Mitigated Food Effect for Asunaprevir (ASV) Utilizing a Lipid-Based Formulation: Similar Exposure with 100mg BID Softgel Capsule (SGC) Relative to 200mg BID of Phase 2 Tablet", Abstract No. A-1247, Interscience Conference on Antimicrobial Agents and Chemotherapy, (Sep. 12, 2012).

(Continued)

*Primary Examiner* — Thomas S Heard
(74) *Attorney, Agent, or Firm* — Pamela A. Mingo

(57) ABSTRACT

Hepatitis C virus inhibitors having the general formula (I) are disclosed. Compositions comprising the compounds and methods for using the compounds to inhibit HCV are also disclosed.

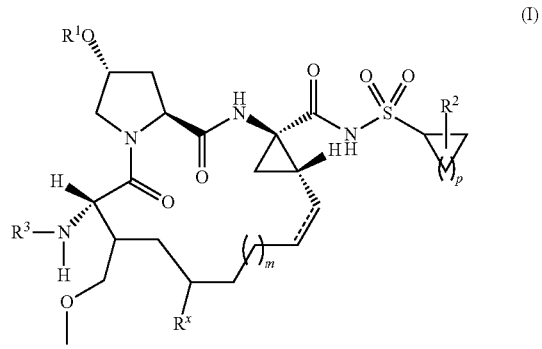

21 Claims, No Drawings

(56) References Cited

FOREIGN PATENT DOCUMENTS

| | | |
|---|---|---|
| WO | WO 00/09558 A1 | 2/2000 |
| WO | WO 00/59929 A1 | 10/2000 |
| WO | WO 02/08244 A2 | 1/2002 |
| WO | WO 02/060926 A2 | 8/2002 |
| WO | WO 03/053349 A2 | 7/2003 |
| WO | WO 03/062265 A2 | 7/2003 |
| WO | WO 03/064416 A1 | 8/2003 |
| WO | WO 03/064455 A2 | 8/2003 |
| WO | WO 03/064456 A1 | 8/2003 |
| WO | WO 03/066103 A1 | 8/2003 |
| WO | WO 03/099274 A1 | 12/2003 |
| WO | WO 03/099316 A1 | 12/2003 |
| WO | WO 2004/009121 A1 | 1/2004 |
| WO | WO 2004/032827 A2 | 4/2004 |
| WO | WO 2004/037855 A1 | 5/2004 |
| WO | WO 2004/043339 A2 | 5/2004 |
| WO | WO 2004/072243 A2 | 8/2004 |
| WO | WO 2004/093798 A2 | 11/2004 |
| WO | WO 2004/093915 A1 | 11/2004 |
| WO | WO 2004/094452 A2 | 11/2004 |
| WO | WO 2004/101602 A2 | 11/2004 |
| WO | WO 2004/101605 A1 | 11/2004 |
| WO | WO 2004/103996 A1 | 12/2004 |
| WO | WO 2004/113365 A2 | 12/2004 |
| WO | WO 2005/010029 A1 | 2/2005 |
| WO | WO 2005/028501 A1 | 3/2005 |
| WO | WO 2005/037214 A2 | 4/2005 |
| WO | WO 2005/037860 A2 | 4/2005 |
| WO | WO 2005/046712 A1 | 5/2005 |
| WO | WO 2005/051410 A1 | 6/2005 |
| WO | WO 2005/051980 A1 | 6/2005 |
| WO | WO 2005/054430 A2 | 6/2005 |
| WO | WO 2005/070955 A1 | 8/2005 |
| WO | WO 2005/073216 A2 | 8/2005 |
| WO | WO 2005/095403 A2 | 10/2005 |
| WO | WO 2005/116054 A1 | 12/2005 |
| WO | WO 2006/000085 A1 | 1/2006 |
| WO | WO 2006/007700 A1 | 1/2006 |
| WO | WO 2006/007708 A1 | 1/2006 |
| WO | WO 2006/016930 A2 | 2/2006 |
| WO | WO 2006/020276 A2 | 2/2006 |
| WO | WO 2006/026352 A1 | 3/2006 |
| WO | WO 2006/033878 A1 | 3/2006 |
| WO | WO 2006/043145 A1 | 4/2006 |
| WO | WO 2006/086381 A2 | 8/2006 |
| WO | WO 2006/096652 A2 | 9/2006 |
| WO | WO 2006/119061 A2 | 11/2006 |
| WO | WO 2006/122188 A2 | 11/2006 |
| WO | WO 2006/130552 A2 | 12/2006 |
| WO | WO 2006/130553 A2 | 12/2006 |
| WO | WO 2006/130554 A2 | 12/2006 |
| WO | WO 2006/130607 A2 | 12/2006 |
| WO | WO 2006/130626 A2 | 12/2006 |
| WO | WO 2006/130627 A2 | 12/2006 |
| WO | WO 2006/130628 A2 | 12/2006 |
| WO | WO 2006/130666 A2 | 12/2006 |
| WO | WO 2006/130686 A2 | 12/2006 |
| WO | WO 2006/130687 A2 | 12/2006 |
| WO | WO 2006/130688 A2 | 12/2006 |
| WO | WO 2007/001406 A2 | 1/2007 |
| WO | WO 2007/008657 A2 | 1/2007 |
| WO | WO 2007/009109 A2 | 1/2007 |
| WO | WO 2007/009227 A1 | 1/2007 |
| WO | WO 2007/011658 A1 | 1/2007 |
| WO | WO 2007/014918 A1 | 2/2007 |
| WO | WO 2007/014919 A1 | 2/2007 |
| WO | WO 2007/014920 A1 | 2/2007 |
| WO | WO 2007/014921 A1 | 2/2007 |
| WO | WO 2007/014922 A1 | 2/2007 |
| WO | WO 2007/014923 A1 | 2/2007 |
| WO | WO 2007/014924 A1 | 2/2007 |
| WO | WO 2007/014925 A1 | 2/2007 |
| WO | WO 2007/014926 A1 | 2/2007 |
| WO | WO 2007/014927 A2 | 2/2007 |
| WO | WO 2007/015787 A1 | 2/2007 |
| WO | WO 2007/015824 A2 | 2/2007 |
| WO | WO 2007/015855 A1 | 2/2007 |
| WO | WO 2007/016441 A1 | 2/2007 |
| WO | WO 2007/016476 A2 | 2/2007 |
| WO | WO 2007/017144 A2 | 2/2007 |
| WO | WO 2007/025307 A2 | 3/2007 |
| WO | WO 2007/030656 A1 | 3/2007 |
| WO | WO 2007/044893 A2 | 4/2007 |
| WO | WO 2007/044933 A1 | 4/2007 |
| WO | WO 2007/056120 A1 | 5/2007 |
| WO | WO 2007/082131 A1 | 7/2007 |
| WO | WO 2007/106317 A2 | 9/2007 |
| WO | WO 2007/120595 A2 | 10/2007 |
| WO | WO 2007/131966 A1 | 11/2007 |
| WO | WO 2007/143694 A2 | 12/2007 |
| WO | WO 2007/148135 A1 | 12/2007 |
| WO | WO 2008/002924 A2 | 1/2008 |
| WO | WO 2008/005511 A2 | 1/2008 |
| WO | WO 2008/005565 A2 | 1/2008 |
| WO | WO 2008/008502 A1 | 1/2008 |
| WO | WO 2008/008776 A2 | 1/2008 |
| WO | WO 2008/019266 A2 | 2/2008 |
| WO | WO 2008/019289 A2 | 2/2008 |
| WO | WO 2008/019303 A2 | 2/2008 |
| WO | WO 2008/021733 A2 | 2/2008 |
| WO | WO 2008/021871 A2 | 2/2008 |
| WO | WO 2008/021956 A2 | 2/2008 |
| WO | WO 2008/021960 A2 | 2/2008 |
| WO | WO 2008/022006 A2 | 2/2008 |
| WO | WO 2008/051475 A2 | 5/2008 |
| WO | WO 2008/051477 A2 | 5/2008 |
| WO | WO 2008/051514 A2 | 5/2008 |
| WO | WO 2008/057208 A2 | 5/2008 |
| WO | WO 2008/057209 A1 | 5/2008 |
| WO | WO 2008/057871 A2 | 5/2008 |
| WO | WO 2008/057873 A2 | 5/2008 |
| WO | WO 2008/057875 A2 | 5/2008 |
| WO | WO 2008/057995 A2 | 5/2008 |
| WO | WO 2008/059046 A1 | 5/2008 |
| WO | WO 2008/060927 A2 | 5/2008 |
| WO | WO 2008/064057 A1 | 5/2008 |
| WO | WO 2008/064061 A1 | 5/2008 |
| WO | WO 2008/064066 A1 | 5/2008 |
| WO | WO 2008/070358 A2 | 6/2008 |
| WO | WO 2008/086161 A1 | 7/2008 |
| WO | WO 2008/092954 A2 | 8/2008 |
| WO | WO 2008/092955 A1 | 8/2008 |
| WO | WO 2008/095058 A1 | 8/2008 |
| WO | WO 2008/095999 A1 | 8/2008 |
| WO | WO 2008/096001 A1 | 8/2008 |
| WO | WO 2008/096002 A1 | 8/2008 |
| WO | WO 2008/098368 A1 | 8/2008 |
| WO | WO 2008/101665 A1 | 8/2008 |
| WO | WO 2008/106130 A2 | 9/2008 |
| WO | WO 2008/128921 A1 | 10/2008 |
| WO | WO 2008/134395 A1 | 11/2008 |
| WO | WO 2008/134397 A1 | 11/2008 |
| WO | WO 2008/134398 A1 | 11/2008 |
| WO | WO 2008/137779 A2 | 11/2008 |
| WO | WO 2008/141227 A1 | 11/2008 |
| WO | WO 2009/005676 A2 | 1/2009 |
| WO | WO 2009/005677 A2 | 1/2009 |
| WO | WO 2009/005690 A2 | 1/2009 |
| WO | WO 2009/010804 A1 | 1/2009 |
| WO | WO 2009/014730 A1 | 1/2009 |
| WO | WO 2009/047264 A1 | 4/2009 |
| WO | WO 2009/053828 A2 | 4/2009 |
| WO | WO 2009/055335 A2 | 4/2009 |
| WO | WO 2009/064955 A1 | 5/2009 |
| WO | WO 2009/064975 A1 | 5/2009 |
| WO | WO 2009/070689 A1 | 6/2009 |
| WO | WO 2009/070692 A1 | 6/2009 |
| WO | WO 2009/073713 A1 | 6/2009 |
| WO | WO 2009/073719 A1 | 6/2009 |
| WO | WO 2009/073780 A1 | 6/2009 |
| WO | WO 2009/076166 A2 | 6/2009 |
| WO | WO 2009/076173 A2 | 6/2009 |
| WO | WO 2009/079352 A1 | 6/2009 |

(56) References Cited

FOREIGN PATENT DOCUMENTS

| | | |
|---|---|---|
| WO | WO 2009/079353 A1 | 6/2009 |
| WO | WO 2009/080542 A1 | 7/2009 |
| WO | WO 2009/082697 A1 | 7/2009 |
| WO | WO 2009/082701 A1 | 7/2009 |
| WO | WO 2009/085659 A1 | 7/2009 |
| WO | WO 2009/094438 A1 | 7/2009 |
| WO | WO 2009/094443 A1 | 7/2009 |
| WO | WO 2009/108507 A1 | 9/2009 |
| WO | WO 2009/117594 A1 | 9/2009 |
| WO | WO 2009/129109 A1 | 10/2009 |
| WO | WO 2009/134624 A1 | 11/2009 |
| WO | WO 2009/134987 A1 | 11/2009 |
| WO | WO 2009/139792 A1 | 11/2009 |
| WO | WO 2009/140475 A1 | 11/2009 |
| WO | WO 2009/140500 A1 | 11/2009 |
| WO | WO 2009/142842 A2 | 11/2009 |
| WO | WO 2009/146347 A1 | 12/2009 |
| WO | WO 2009/148923 A1 | 12/2009 |
| WO | WO 2010/011566 A1 | 1/2010 |
| WO | WO 2010/015545 A1 | 2/2010 |
| WO | WO 2010/030359 A2 | 3/2010 |
| WO | WO 2010/031829 A1 | 3/2010 |
| WO | WO 2010/031832 A2 | 3/2010 |
| WO | WO 2010/033466 A1 | 3/2010 |
| WO | WO 2010/034105 A1 | 4/2010 |
| WO | WO 2010/036551 A1 | 4/2010 |
| WO | WO 2010/036871 A1 | 4/2010 |
| WO | WO 2010/036896 A1 | 4/2010 |
| WO | WO 2010/059937 A1 | 5/2010 |
| WO | WO 2010/065577 A1 | 6/2010 |
| WO | WO 2010/068760 A2 | 6/2010 |
| WO | WO 2010/068761 A2 | 6/2010 |
| WO | WO 2010/075127 A1 | 7/2010 |
| WO | WO 2010/077783 A1 | 7/2010 |
| WO | WO 2010/080389 A1 | 7/2010 |
| WO | WO 2010/088394 A1 | 8/2010 |
| WO | WO 2010/115981 A1 | 10/2010 |
| WO | WO 2010/116248 A1 | 10/2010 |
| WO | WO 2010/132163 A1 | 11/2010 |
| WO | WO 2010/145523 A1 | 12/2010 |
| WO | WO 2011/002807 A1 | 1/2011 |
| WO | WO 2011/002808 A1 | 1/2011 |
| WO | WO 2011/005646 A2 | 1/2011 |
| WO | WO 2011/014487 A1 | 2/2011 |
| WO | WO 2011/025849 A1 | 3/2011 |
| WO | WO 2011/034518 A1 | 3/2011 |
| WO | WO 2011/038283 A1 | 3/2011 |
| WO | WO 2011/038293 A1 | 3/2011 |
| WO | WO 2011/041551 A1 | 4/2011 |
| WO | WO 2011/046811 A1 | 4/2011 |
| WO | WO 2011/049908 A2 | 4/2011 |
| WO | WO 2011/063501 A1 | 6/2011 |
| WO | WO 2011/063502 A1 | 6/2011 |
| WO | WO 2011/072370 A1 | 6/2011 |
| WO | WO 2011/091757 A1 | 8/2011 |
| WO | WO 2011/112558 A2 | 9/2011 |
| WO | WO 2011/150190 A2 | 12/2011 |
| WO | WO 2011/156337 A2 | 12/2011 |
| WO | WO 2012/018829 A1 | 2/2012 |
| WO | WO 2012/019299 A1 | 2/2012 |
| WO | WO 2012/037259 A1 | 3/2012 |
| WO | WO 2012/040040 A1 | 3/2012 |
| WO | WO 2012/040167 A1 | 3/2012 |
| WO | WO 2012/040242 A1 | 3/2012 |
| WO | WO 2012/047764 A1 | 4/2012 |
| WO | WO 2012/054874 A1 | 4/2012 |
| WO | WO 2012/082672 A2 | 6/2012 |
| WO | WO 2012/092409 A2 | 7/2012 |
| WO | WO 2012/092411 A2 | 7/2012 |
| WO | WO 2012/151195 A1 | 11/2012 |
| WO | WO 2012/166459 A1 | 12/2012 |
| WO | WO 2012/173983 A1 | 12/2012 |
| WO | WO 2013/028465 A1 | 2/2013 |
| WO | WO 2013/028470 A1 | 2/2013 |
| WO | WO 2013/028471 A1 | 2/2013 |
| WO | WO 2013/040568 A1 | 3/2013 |
| WO | WO 2013/066753 A1 | 5/2013 |
| WO | WO 2013/074386 A2 | 5/2013 |
| WO | WO 2013/106689 A1 | 7/2013 |
| WO | WO 2013/120371 A1 | 8/2013 |
| WO | WO 2014/008285 A1 | 1/2014 |
| WO | WO 2014/019344 A1 | 2/2014 |
| WO | WO 2014/025736 A1 | 2/2014 |
| WO | WO 2014/062196 A1 | 4/2014 |
| WO | WO 2014/070964 A1 | 5/2014 |
| WO | WO 2014/070974 A1 | 5/2014 |
| WO | WO 2014/071007 A1 | 5/2014 |
| WO | WO 2014/071032 A1 | 5/2014 |

OTHER PUBLICATIONS

Lauer, G.M. et al., "Hepatitis C Virus Infection", The New England Journal of Medicine, vol. 345, No. 1, pp. 41-52 (2001).

Llinàs-Brunet, M. et al., "A Systematic Approach to the Optimization of Substrate-Based Inhibitors of the Hepatitis C Virus NS3 Protease: Discovery of Potent and Specific Tripeptide Inhibitors", Journal of Medicinal Chemistry, vol. 47, No. 26, pp. 6584-6594 (2004).

Poupart, M.-A. et al., "Solid-Phase Synthesis of Peptidomimetic Inhibitors for the Hepatitis C Virus NS3 Protease", The Journal of Organic Chemistry, vol. 66, No. 14, pp. 4743-4751 (2001).

Ribeiro, C.M.R. et al., "Ultrasound in enzymatic resolution of ethyl 3-hydroxy-3-phenylpropanoate", Tetrahedron Letters, vol. 42, pp. 6477-6479 (2001).

Tsantrizos, Y.S. et al., "Olefin ring-closing metathesis as a powerful tool in drug discovery and development—potent macrocyclic inhibitors of the hepatitis C virus NS3 protease", Journal of Organometallic Chemistry, vol. 691, pp. 5163-5174 (2006).

Wirz, B. et al., "Enzymatic preparation of homochiral 2-isobutyl succinic acid derivatives", Tetrahedron: Asymmetry, vol. 8, No. 2, pp. 187-189 (1997).

Yang, S. et al., "Chemoenzymatic Synthesis of (R)-(—)-Citramalic Acid", Synthesis, pp. 365-366 (1992).

HEPATITIS C VIRUS INHIBITORS

CROSS-REFERENCE TO RELATED APPLICATIONS

This application claims priority to U.S. Provisional Patent Application 61/774,136 filed Mar. 7, 2013, hereby incorporated by reference in its entirety.

The present disclosure is generally directed to antiviral compounds, and more specifically directed to compounds which inhibit the function of the NS3 protease (also referred to herein as "serine protease") encoded by Hepatitis C virus (HCV), compositions comprising such compounds, and methods for inhibiting the function of the NS3 protease.

HCV is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma.

Presently, the most effective HCV therapy employs a combination of alpha-interferon and ribavirin, leading to sustained efficacy in 40% of patients. Recent clinical results demonstrate that pegylated alpha-interferon is superior to unmodified alpha-interferon as monotherapy. However, even with experimental therapeutic regimens involving combinations of pegylated alpha-interferon and ribavirin, a substantial fraction of patients do not have a sustained reduction in viral load. Thus, there is a clear and unmet need to develop effective therapeutics for treatment of HCV infection.

HCV is a positive-stranded RNA virus. Based on a comparison of the deduced amino acid sequence and the extensive similarity in the 5' untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. Six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one cleaves at the NS2-NS3 junction; the second one is a serine protease contained within the N-terminal region of NS3 and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a co-factor for the NS3 protease and possibly assisting in the membrane localization of NS3 and other viral replicase components. The complex formation of the NS3 protein with NS4A is essential for efficient polyprotein processing, enhancing the proteolytic cleavage at all of the sites. The NS3 protein also exhibits nucleoside triphosphatase and RNA helicase activities. NS5B is a RNA-dependent RNA polymerase that is involved in the replication of HCV.

The present disclosure provides peptide compounds that can inhibit the functioning of the NS3 protease, e.g., in combination with the NS4A protease. Further, the present disclosure describes the administration of combination therapy to a patient whereby a compound in accordance with the present disclosure, which is effective to inhibit the HCV NS3 protease, can be administered with additional compounds having anti-HCV activity.

In its first aspect the present disclosure provides a compound of formula (I)

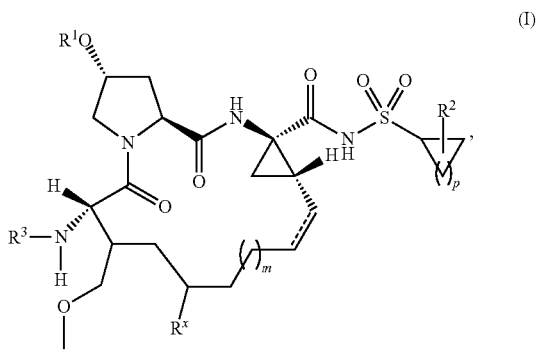

or a pharmaceutically acceptable salt thereof, wherein
p is 1 or 2;
----- is a single or double bond;
m is 0, 1, or 2;
$R^1$ is selected from

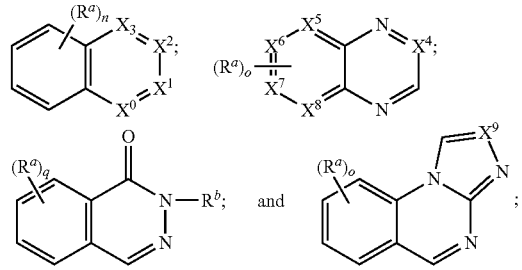

wherein $R^1$ is attached to the parent molecular moiety through any substitutable carbon atom in the group;
n is 0, 1, 2, 3, 4, 5, or 6;
o is 0, 1, 2, 3, 4, or 5;
q is 0, 1, 2, 3, or 4;
$X^0$ is selected from CH and N;
$X^1$ is selected from CH and N;
$X^2$ and $X^3$ are independently selected from CH, C($R^a$) and N; provided that at least one of $X^1$, $X^2$, and $X^3$ is other than N;
$X^4$ is selected from CH and $CR^a$;
one of $X^5$, $X^6$, $X^7$, and $X^8$ is N and the others are selected from CH and $CR^a$;
$X^9$ is selected from $CR^a$, CH, and N;
each $R^a$ is independently selected from alkenyloxy, alkoxy, alkoxyalkoxy, alkoxycarbonyl, alkyl, benzodioxanyl, carboxamido, carboxy, carboxyalkoxy, cyano, cycloalkyl, cycloalkylalkoxy, cycloalkyloxy, deuteroalkoxy, dialkylamino, halo, haloalkyl, haloalkoxy, haloalkoxycarbonyl, hydroxy, imidazolyl, morpholinyl, oxazolyl, phenyl, piperazinyl, pyrazolyl, pyridinyl, pyrrolidinyl, thiazolyl, and —NR$^q$R$^{q'}$, wherein the imidazolyl, the morpholinyl, the oxazolyl, the phenyl, the piperazinyl, the pyridinyl, the pyrrolidinyl, and the thiazolyl are optionally substituted with one or two groups independently selected from alkoxy, alkyl, alkylsulfonyl, halo, haloalkoxy, haloalkyl, and morpholinyl; and wherein two adjacent R$^a$ groups, together with the carbon atoms to which they are attached, can optionally form a ring selected from dioxanyl, dioxolanyl, furanyl, morpholinyl, pyranyl, and phenyl, wherein the ring is optionally substituted with one or two groups independently selected from alkyl and halo;

R$^b$ is alkyl;

R$^x$ is selected from hydrogen and methyl;

R$^2$ is selected from hydrogen, alkyl, deuteroalkyl, halo, haloalkoxy, haloalkyl, and hydroxyalkyl;

R$^3$ is selected from hydrogen, alkoxyalkoxycarbonyl, alkoxycarbonyl, alkylaminocarbonyl, alkylcarbonyl, cycloalkylalkoxycarbonyl, cycloalkylcarbonyl, cycloalkyloxycarbonyl, deuteroalkoxycarbonyl, deuterohaloalkoxycarbonyl, dialkylaminocarbonyl, dialkylaminocarbonylcarbonyl, haloalkoxycarbonyl, haloalkylaminocarbonyl, haloalkylcarbonyl, heterocyclylcarbonyl, heterocyclyloxycarbonyl, phenylcarbonyl, and phenyloxycarbonyl, wherein the cycloalkyl part of the cycloalkylalkoxycarbonyl, the cycloalkylcarbonyl, and the cycloalkyloxycarbonyl, the heterocyclyl part of the heterocyclylcarbonyl and the heterocyclyloxycarbonyl, and the phenyl part of the phenylcarbonyl and the phenyloxycarbonyl, is optionally substituted with one, two, or three groups independently selected from alkyl, alkylamino, alkylcarbonyl, cycloalkyl, dialkylamino, halo, haloalkoxy, and haloalkyl; and one of R$^q$ and R$^{q'}$ is selected from hydrogen and alkyl and the other is selected from alkylcarbonyl and phenylcarbonyl.

In a first embodiment of the first aspect the present disclosure provides a compound of formula (I), or a pharmaceutically acceptable salt thereof, wherein p is 1. In a second embodiment of the first aspect, ---- is a double bond. In a third embodiment of the first aspect, m is 1. In a fourth embodiment of the first aspect R$^1$ is

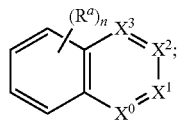

wherein R$^1$ is attached to the parent molecular moiety through any substitutable carbon atom in the group;

n is 1, q is 0, 1, 2, 3, or 4;

X$^0$ is selected from CH and N;

X$^1$ is selected from CH and N;

X$^2$ and X$^3$ are independently selected from CH, C(R$^a$) and N; provided that at least one of X$^1$, X$^2$, and X$^3$ is other than N;

X$^4$ is selected from CH and CR$^a$;

each R$^a$ is independently selected from alkoxy, alkyl, halo, and haloalkyl.

In a fifth embodiment of the first aspect the present disclosure provides a compound of formula (I), or a pharmaceutically acceptable salt thereof, wherein R$^2$ is selected from hydrogen, alkyl, and haloalkyl.

In a sixth embodiment of the first aspect the present disclosure provides a compound of formula (I), or a pharmaceutically acceptable salt thereof, wherein R$^3$ is selected from alkoxycarbonyl and haloalkoxycarbonyl.

In a seventh embodiment of the first aspect the present disclosure provides a compound of formula (I), or a pharmaceutically acceptable salt thereof, wherein p is 1;

---- is a double bond;

m is 1; and

R$^1$ is

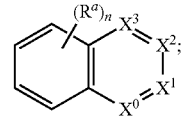

wherein wherein R$^1$ is attached to the parent molecular moiety through any substitutable carbon atom in the group;

n is 1, q is 0, 1, 2, 3, or 4;

X$^0$ is selected from CH and N;

X$^1$ is selected from CH and N;

X$^2$ and X$^3$ are independently selected from CH, C(R$^a$) and N; provided that at least one of X$^1$, X$^2$, and X$^3$ is other than N;

X$^4$ is selected from CH and CR$^a$; and each R$^a$ is independently selected from alkoxy, alkyl, halo, and haloalkyl.

In a second aspect the present disclosure provides a composition comprising a compound of formula (I), or a pharmaceutically acceptable salt thereof, and a pharmaceutically acceptable carrier. In a first embodiment of the second aspect the present disclosure provides a composition comprising a compound of formula (I), or a pharmaceutically acceptable salt thereof, at least one additional compound having anti-HCV activity, and a pharmaceutical carrier. In a second embodiment at least one of the additional compounds is an interferon or a ribavirin. In a third embodiment the interferon is selected from interferon alpha 2B, pegylated interferon alpha, consensus interferon, interferon alpha 2A, and lymphoblastoid interferon tau. In a fourth embodiment of the second aspect the present disclosure provides a composition comprising a compound of formula (I), or a pharmaceutically acceptable salt thereof, at least one additional compound having anti-HCV activity, and a pharmaceutical carrier, wherein at least one of the additional compounds is selected from interleukin 2, interleukin 6, interleukin 12, Imiquimod, ribavirin, an inosine 5'-monophosphate dehydrogenase inhibitor, amantadine, and rimantadine. In a fifth embodiment of the second aspect the present disclosure provides a composition comprising a compound of formula (I), or a pharmaceutically acceptable salt thereof, at least one additional compound having anti-HCV activity, and a pharmaceutical carrier, wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

In a third aspect the present disclosure provides a method of treating an HCV infection in a patient, comprising administering to the patient a therapeutically effective amount of a compound of formula (I), or a pharmaceutically acceptable salt thereof. In a first embodiment of the third aspect the method further comprises administering at least one additional compound having anti-HCV activity prior to, after, or simultaneously with the compound of formula (I), or a pharmaceutically acceptable salt thereof. In a second embodiment of the third aspect at least one of the additional compounds is an interferon or a ribavirin. In a third embodiment the interferon is selected from interferon alpha 2B, pegylated interferon alpha, consensus interferon, interferon alpha 2A, and lymphoblastoid interferon tau. In a fourth embodiment of the third aspect the present disclosure provides a method of treating an HCV infection in a patient, comprising administering to the patient a therapeutically effective amount of a compound of formula (I), or a pharmaceutically acceptable salt thereof, and at least one additional compound having anti-HCV activity prior to, after, or simultaneously with the compound of formula (I), or a pharmaceutically acceptable salt thereof, wherein at least one of the additional compounds is selected from interleukin 2, interleukin 6, interleukin 12, Imiquimod, ribavirin, an inosine 5'-monophosphate dehydrogenase inhibitor, amantadine, and rimantadine. In a fifth embodiment of the third aspect the present disclosure provides a method of treating an HCV infection in a patient, comprising administering to the patient a therapeutically effective amount of a compound of formula (I), or a pharmaceutically acceptable salt thereof, and at least one additional compound having anti-HCV activity prior to, after, or simultaneously with the compound of formula (I), or a pharmaceutically acceptable salt thereof, wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

Other aspects of the present disclosure may include suitable combinations of embodiments disclosed herein.

Yet other aspects and embodiments may be found in the description provided herein.

The description of the present disclosure herein should be construed in congruity with the laws and principals of chemical bonding. In some instances it may be necessary to remove a hydrogen atom in order to accommodate a substituent at any given location.

It should be understood that the compounds encompassed by the present disclosure are those that are suitably stable for use as pharmaceutical agent.

It is intended that the definition of any substituent or variable at a particular location in a molecule be independent of its definitions elsewhere in that molecule. For example, when n is 2, each of the two $R^1$ groups may be the same or different.

All patents, patent applications, and literature references cited in the specification are herein incorporated by reference in their entirety. In the case of inconsistencies, the present disclosure, including definitions, will prevail.

As used herein, the singular forms "a", "an", and "the" include plural reference unless the context clearly dictates otherwise.

The term "alkenyl," as used herein, refers to a group derived from a straight or branched chain saturated hydrocarbon containing from two to ten carbon atoms and at least one double bond. In one embodiment the alkenyl groups contain from two to six carbon atoms. In another embodiment the alkenyl groups contain from two to four carbon atoms.

The term "alkenyloxy," as used herein, refers to an alkenyl group attached to the parent molecular moiety through an oxygen atom.

The term "alkoxy," as used herein, refers to an alkyl group attached to the parent molecular moiety through an oxygen atom.

The term "alkoxyalkoxy," as used herein, refers to an alkoxyalkyl group attached to the parent molecular moiety through an oxygen atom.

The term "alkoxyalkoxycarbonyl," as used herein, refers to an alkoxyalkoxy group attached to the parent molecular moiety through a carbonyl group.

The term "alkoxyalkyl," as used herein, refers to an alkyl group substituted with one, two, or three alkoxy groups.

The term "alkoxycarbonyl," as used herein, refers to an alkoxy group attached to the parent molecular moiety through a carbonyl group.

The term "alkyl," as used herein, refers to a group derived from a straight or branched chain saturated hydrocarbon containing from one to ten carbon atoms. In one embodiment the alkyl groups contain from one to six carbon atoms. In another embodiment the alkyl groups contain from one to four carbon atoms.

The term "alkylamino," as used herein, refers to —NHR, wherein R is an alkyl group.

The term "alkylaminocarbonyl," as used herein, refers to an alkylamino group attached to the parent molecular moiety through a carbonyl group.

The term "alkylcarbonyl," as used herein, refers to an alkyl group attached to the parent molecular moiety through a carbonyl group.

The term "alkylsulfonyl," as used herein, refers to an alkyl group attached to the parent molecular moiety through a sulfonyl group.

The term "carbonyl," as used herein, refers to —C(O)—.

The term "carboxamido," as used herein, refers to —C(O)NR$^x$R$^y$, wherein R$^x$ and R$^y$ are independently selected from hydrogen and alkyl.

The term "carboxy," as used herein, refers to —CO$_2$H.

The term "carboxyalkoxy," as used herein, refers to a carboxyalkyl group attached to the parent molecular moiety through an oxygen atom.

The term "carboxyalkyl," as used herein, refers to an alkyl group substituted with one, two, or three carboxy groups.

The term "cyano," as used herein, refers to —CN.

The term "cycloalkyl," as used herein, refers to a saturated monocyclic or bicyclic hydrocarbon ring system having three to seven carbon atoms and zero heteroatoms. Representative examples of cycloalkyl groups include, but are not limited to, cyclopropyl, cyclobutyl, and cyclopentyl.

The term "cycloalkylalkoxy," as used herein, refers to a (cycloalkyl)alkyl group attached to the parent molecular moiety through an oxygen atom.

The term "cycloalkylalkoxycarbonyl," as used herein, refers to a cycloalkylalkoxy group attached to the parent molecular moiety through a carbonyl group.

The term "(cycloalkyl)alkyl," as used herein, refers to an alkyl group substituted with one, two, or three cycloalkyl groups.

The term "cycloalkylcarbonyl," as used herein, refers to a cycloalkyl group attached to the parent molecular moiety through a carbonyl group.

The term "cycloalkyloxy," as used herein, refers to a cycloalkyl group attached to the parent molecular moiety through an oxygen atom.

The term "cycloalkyloxycarbonyl," as used herein, refers to a cycloalkyloxy group attached to the parent molecular moiety through a carbonyl group.

The term "deuteroalkoxy," as used herein, refers to an alkoxy group wherein at least one hydrogen atom is replaced by a deuterium atom.

The term "deuteroalkoxycarbonyl," as used herein, refers to a deuteroalkoxy group attached to the parent molecular moiety through a carbonyl group.

The term "deuteroalkyl," as used herein, refers to an alkyl group wherein at least one hydrogen atom is replaced by a deuterium atom.

The term "deuterohaloalkoxy," as used herein, refers to a haloalkoxy group wherein at least one hydrogen atom is replaced by a deuterium atom.

The term "deuterohaloalkoxycarbonyl," as used herein, refers to a deuterohaloalkoxy group attached to the parent molecular moiety through a carbonyl group.

The term "dialkylamino," as used herein, refers to —NR$^p$R$^q$, wherein R$^p$ and R$^q$ are alkyl groups. The alkyl groups may be the same or different.

The term "dialkylaminocarbonyl," as used herein, refers to a dialkylamino group attached to the parent molecular moiety through a carbonyl group.

The term "dialkylaminocarbonylcarbonyl," as used herein, refers to a dialkylaminocarbonyl group attached to the parent molecular moiety through a carbonyl group.

The terms "halo" and "halogen," as used herein, refer to F, Cl, Br, and I.

The term "haloalkoxy," as used herein, refers to a haloalkyl group attached to the parent molecular moiety through an oxygen atom.

The term "haloalkoxycarbonyl," as used herein, refers to a haloalkoxy group attached to the parent molecular moiety through a carbonyl group.

The term "haloalkyl," as used herein, refers to an alkyl group substituted with one, two, three, or four halogen atoms.

The term "haloalkylamino," as used herein, refers to an alkyl amino group wherein the alkyl is substituted with one, two, three, or four halogen atoms.

The term "haloalkylaminocarbonyl," as used herein, refers to a haloalkylamino group attached to the parent molecular moiety through a carbonyl group.

The term "haloalkylcarbonyl," as used herein, refers to a haloalkyl group attached to the parent molecular moiety through a carbonyl group.

The term "heterocyclyl," as used herein, refers to a four-, five-, six-, or seven-membered ring containing one, two, three, or four heteroatoms independently selected from nitrogen, oxygen, and sulfur. The four-membered ring has zero double bonds, the five-membered ring has zero to two double bonds, and the six- and seven-membered rings have zero to three double bonds. The term "heterocyclyl" also includes bicyclic groups in which the heterocyclyl ring is fused to another monocyclic heterocyclyl group, or a four- to six-membered aromatic or non-aromatic carbocyclic ring; as well as bridged bicyclic groups such as 7-azabicyclo[2.2.1]hept-7-yl, 2-azabicyclo[2.2.2]oc-2-tyl, and 2-azabicyclo[2.2.2]oc-3-tyl. The heterocyclyl groups of the present disclosure can be attached to the parent molecular moiety through any carbon atom or nitrogen atom in the group. Examples of heterocyclyl groups include, but are not limited to, benzothienyl, furyl, imidazolyl, indolinyl, indolyl, isothiazolyl, isoxazolyl, morpholinyl, oxazolyl, piperazinyl, piperidinyl, pyrazolyl, pyridinyl, pyrrolidinyl, pyrrolopyridinyl, pyrrolyl, thiazolyl, thienyl, thiomorpholinyl, 7-azabicyclo[2.2.1]hept-7-yl, 2-azabicyclo[2.2.2]oc-2-tyl, and 2-azabicyclo[2.2.2]oc-3-tyl.

The term "heterocyclylcarbonyl," as used herein, refers to a heterocyclyl group attached to the parent molecular moiety through a carbonyl group.

The term "heterocyclyloxy," as used herein, refers to a heterocyclyl group attached to the parent molecular moiety through an oxygen atom.

The term "heterocyclyloxycarbonyl," as used herein, refers to a heterocyclyloxy group attached to the parent molecular moiety through a carbonyl group.

The term "hydroxy," as used herein, refers to —OH.

The term "hydroxyalkyl," as used herein, refers to an alkyl group substituted with one, two, or three hydroxy groups.

The term "phenylcarbonyl," as used herein, refers to a phenyl group attached to the parent molecular moiety through a carbonyl group.

The term "phenyloxy," as used herein, refers to a phenyl group attached to the parent molecular moiety through an oxygen atom.

The term "phenyloxycarbonyl," as used herein, refers to a phenyloxy group attached to the parent molecular moiety through a carbonyl group.

The term "sulfonyl," as used herein, refers to —S(O)$_2$—.

The compounds of the present disclosure can exist as pharmaceutically acceptable salts. The term "pharmaceutically acceptable salt," as used herein, represents salts or zwitterionic forms of the compounds of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use. The salts can be prepared during the final isolation and purification of the compounds or separately by reacting a suitable basic functionality with a suitable acid. Representative acid addition salts include acetate, adipate, alginate, citrate, aspartate, benzoate, benzenesulfonate, bisulfate, butyrate, camphorate, camphorsulfonate; digluconate, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting an acidic group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine. Other representative organic amines useful for the formation of base addition salts include ethylenediamine, ethanolamine, diethanolamine, piperidine, and piperazine.

As used herein, the term "anti-HCV activity" means the compound is effective to treat the HCV virus.

The term "compounds of the disclosure", and equivalent expressions, are meant to embrace compounds of formula (I), and pharmaceutically acceptable enantiomers, diastereomers, and salts thereof. Similarly, references to intermediates, are meant to embrace their salts where the context so permits.

The term "patient" includes both human and other mammals.

The term "pharmaceutical composition" means a composition comprising a compound of the disclosure in combination with at least one additional pharmaceutical carrier, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Ingredients listed in Remington's Pharmaceutical Sciences, 18$^{th}$ ed., Mack Publishing Company, Easton, Pa. (1999) for example, may be used.

The phrase "pharmaceutically acceptable" is employed herein to refer to those compounds, materials, compositions, and/or dosage forms which are, within the scope of sound medical judgment, suitable for use in contact with the tissues of patients without excessive toxicity, irritation, allergic response, or other problem or complication commensurate with a reasonable risk/benefit ratio.

The term "therapeutically effective amount" means the total amount of each active component that is sufficient to show a meaningful patient benefit, e.g., a sustained reduction in viral load. When applied to an individual active ingredient, administered alone, the term refers to that ingredient alone. When applied to a combination, the term refers to combined amounts of the active ingredients that result in the therapeutic effect, whether administered in combination, serially or simultaneously.

The terms "treat" and "treating" refers to: (i) preventing a disease, disorder or condition from occurring in a patient which may be predisposed to the disease, disorder and/or condition but has not yet been diagnosed as having it; (ii) inhibiting the disease, disorder or condition, i.e., arresting its development; and/or (iii) relieving the disease, disorder or condition, i.e., causing regression of the disease, disorder and/or condition.

Where used in naming compounds of the present disclosure, the designations P1', P1, P2, P2*, P3, and P4, as used herein, map the relative positions of the amino acid residues of a protease inhibitor binding relative to the binding of the natural peptide cleavage substrate. Cleavage occurs in the natural substrate between P1 and P1' where the nonprime positions designate amino acids starting from the C-terminus end of the peptide natural cleavage site extending towards the N-terminus; whereas, the prime positions emanate from the N-terminus end of the cleavage site designation and extend toward the C-terminus. For example, P1' refers to the first position away from the right hand end of the C-terminus of the cleavage site (i.e. N-terminus first position); whereas P1 starts the numbering from the left hand side of the C-terminus cleavage site, P2: second position from the C-terminus, etc.). (see Berger A. & Schechter I., Transactions of the Royal Society London series (1970), B257, 249-264].

Asymmetric centers exist in the compounds of the present disclosure. For example, the compounds may include P1 cyclopropyl element of formula

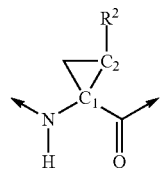

P1 wherein $C_1$ and $C_2$ each represent an asymmetric carbon atom at positions 1 and 2 of the cyclopropyl ring.

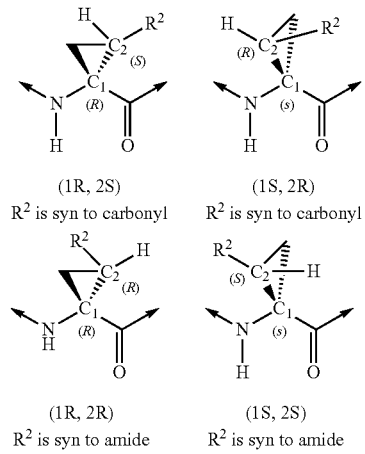

(1R, 2S)  (1S, 2R)
$R^2$ is syn to carbonyl  $R^2$ is syn to carbonyl (1R, 2R)  (1S, 2S)
$R^2$ is syn to amide  $R^2$ is syn to amide It should be understood that the disclosure encompasses all stereochemical forms, or mixtures thereof, which possess the ability to inhibit HCV protease.

Certain compounds of the present disclosure may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

Certain compounds of the present disclosure may exist in zwitterionic form and the present disclosure includes each zwitterionic form of these compounds and mixtures thereof.

When it is possible that, for use in therapy, therapeutically effective amounts of a compound of formula (I), as well as pharmaceutically acceptable salts thereof, may be administered as the raw chemical, it is possible to present the active ingredient as a pharmaceutical composition. Accordingly, the disclosure further provides pharmaceutical compositions, which include therapeutically effective amounts of compounds of formula (I) or pharmaceutically acceptable salts thereof, and one or more pharmaceutically acceptable carriers, diluents, or excipients. The compounds of formula (I) and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the disclosure there is also provided a process for the preparation of a pharmaceutical formulation including admixing a compound of formula (I), or a pharmaceutically acceptable salt thereof, with one or more pharmaceutically acceptable carriers, diluents, or excipients.

Pharmaceutical formulations may be presented in unit dose forms containing a predetermined amount of active ingredient per unit dose. Dosage levels of between about 0.01 and about 150 milligram per kilogram ("mg/kg") body weight per day, preferably between about 0.05 and about 100 mg/kg body weight per day of the compounds of the disclosure are typical in a monotherapy for the prevention and treatment of HCV mediated disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Generally, treatment is initiated with small dosages substantially less than the optimum dose of the compound. Thereafter, the dosage is increased by small increments until the optimum effect under the circumstances is reached. In general, the compound is most desirably administered at a concentration level that will generally afford antivirally effective results without causing any harmful or deleterious side effects.

When the compositions of this disclosure comprise a combination of a compound of the disclosure and one or more additional therapeutic and/or prophylactic agent, both the compound and the additional agent can be present in a dose that is less than or equal to the dosage normally administered in a monotherapy regimen. The compositions of this disclosure may be co-formulated with one or more additional therapeutic or prophylactic agents, for example, in the form of a monolithic and/or bi/multi-layer tablet or may be administered separately from the therapeutic or prophylactic agent(s).

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitably comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phospholipids, such as cholesterol, stearylamine, or phophatidylcholines.

The compounds of formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxide-polylysine substituted with palitoyl residues. Furthermore, the compounds may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouth washes.

Pharmaceutical formulations adapted for rectal administration may be presented as suppositories or as enemas.

Pharmaceutical formulations adapted for nasal administration wherein the carrier is a solid include a course powder which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

Table 1 below lists some illustrative examples of compounds that can be administered with the compounds of this disclosure. The compounds of the disclosure can be administered with other anti-HCV activity compounds in combination therapy, either jointly or separately, or by combining the compounds into a composition.

TABLE 1

| Brand Name | Physiological Class | Type of Inhibitor or Target | Source Company |
| --- | --- | --- | --- |
| NIM811 | | Cyclophilin Inhibitor | Novartis |
| Zadaxin | | Immuno-modulator | Sciclone |
| Suvus | | Methylene blue | Bioenvision |
| Actilon (CPG10101) | | TLR9 agonist | Coley |
| Batabulin (T67) | Anticancer | β-tubulin inhibitor | Tularik Inc., South San Francisco, CA |
| ISIS 14803 | Antiviral | antisense | ISIS Pharmaceuticals Inc, Carlsbad, CA/Elan Phamaceuticals Inc., New York, NY |
| Summetrel | Antiviral | antiviral | Endo Pharmaceuticals Holdings Inc., Chadds Ford, PA |
| GS-9132 (ACH-806) | Antiviral | HCV Inhibitor | Achillion/Gilead |
| Pyrazolopyrimidine compounds and salts From WO-2005047288 26 May 2005 | Antiviral | HCV Inhibitors | Arrow Therapeutics Ltd. |

TABLE 1-continued

| Brand Name | Physiological Class | Type of Inhibitor or Target | Source Company |
|---|---|---|---|
| Levovirin | Antiviral | IMPDH inhibitor | Ribapharm Inc., Costa Mesa, CA |
| Merimepodib (VX-497) | Antiviral | IMPDH inhibitor | Vertex Pharmaceuticals Inc., Cambridge, MA |
| XTL-6865 (XTL-002) | Antiviral | monoclonal antibody | XTL Biopharmaceuticals Ltd., Rehovot, Isreal |
| Telaprevir (VX-950, LY-570310) | Antiviral | NS3 serine protease inhibitor | Vertex Pharmaceuticals Inc., Cambridge, MA/Eli Lilly and Co. Inc., Indianapolis, IN |
| HCV-796 | Antiviral | NS5B Replicase Inhibitor | Wyeth/Viropharma |
| NM-283 | Antiviral | NS5B Replicase Inhibitor | Idenix/Novartis |
| GL-59728 | Antiviral | NS5B Replicase Inhibitor | Gene Labs/Novartis |
| GL-60667 | Antiviral | NS5B Replicase Inhibitor | Gene Labs/Novartis |
| 2'C MeA | Antiviral | NS5B Replicase Inhibitor | Gilead |
| PSI 6130 | Antiviral | NS5B Replicase Inhibitor | Roche |
| R1626 | Antiviral | NS5B Replicase Inhibitor | Roche |
| 2'C Methyl adenosine | Antiviral | NS5B Replicase Inhibitor | Merck |
| JTK-003 | Antiviral | RdRp inhibitor | Japan Tobacco Inc., Tokyo, Japan |
| Levovirin | Antiviral | ribavirin | ICN Pharmaceuticals, Costa Mesa, CA |
| Ribavirin | Antiviral | ribavirin | Schering-Plough Corporation, Kenilworth, NJ |
| Viramidine | Antiviral | Ribavirin Prodrug | Ribapharm Inc., Costa Mesa, CA |
| Heptazyme | Antiviral | ribozyme | Ribozyme Pharmaceuticals Inc., Boulder, CO |
| BILN-2061 | Antiviral | serine protease inhibitor | Boehringer Ingelheim Pharma KG, Ingelheim, Germany |
| SCH 503034 | Antiviral | serine protease inhibitor | Schering Plough |
| Zadazim | Immune modulator | Immune modulator | SciClone Pharmaceuticals Inc., San Mateo, CA |
| Ceplene | Immunomodulator | immune modulator | Maxim Pharmaceuticals Inc., San Diego, CA |
| CellCept | Immunosuppressant | HCV IgG immunosuppressant | F. Hoffmann-La Roche LTD, Basel, Switzerland |
| Civacir | Immunosuppressant | HCV IgG immunosuppressant | Nabi Biopharmaceuticals Inc., Boca Raton, FL |
| Albuferon-α | Interferon | albumin IFN-α2b | Human Genome Sciences Inc., Rockville, MD |
| Infergen A | Interferon | IFN alfacon-1 | InterMune Pharmaceuticals Inc., Brisbane, CA |
| Omega IFN | Interferon | IFN-ω | Intarcia Therapeutics |
| IFN-β and EMZ701 | Interferon | IFN-β and EMZ701 | Transition Therapeutics Inc., Ontario, Canada |
| Rebif | Interferon | IFN-β1a | Serono, Geneva, Switzerland |
| Roferon A | Interferon | IFN-α2a | F. Hoffmann-La Roche LTD, Basel, Switzerland |

TABLE 1-continued

| Brand Name | Physiological Class | Type of Inhibitor or Target | Source Company |
| --- | --- | --- | --- |
| Intron A | Interferon | IFN-α2b | Schering-Plough Corporation, Kenilworth, NJ |
| Intron A and Zadaxin | Interferon | IFN-α2b/α1-thymosin | RegeneRx Biopharma. Inc., Bethesda, MD/ SciClone Pharmaceuticals Inc, San Mateo, CA |
| Rebetron | Interferon | IFN-α2b/ribavirin | Schering-Plough Corporation, Kenilworth, NJ |
| Actimmune | Interferon | INF-γ | InterMune Inc., Brisbane, CA |
| Interferon-β | Interferon | Interferon-β-1a | Serono |
| Multiferon | Interferon | Long lasting IFN | Viragen/ Valentis |
| Wellferon | Interferon | Lympho-blastoid IFN-αn1 | GlaxoSmithKline plc, Uxbridge, UK |
| Omniferon | Interferon | natural IFN-α | Viragen Inc., Plantation, FL |
| Pegasys | Interferon | PEGylated IFN-α2a | F. Hoffmann-La Roche LTD, Basel, Switzerland |
| Pegasys and Ceplene | Interferon | PEGylated IFN-α2a/ immune modulator | Maxim Pharmaceuticals Inc., San Diego, CA |
| Pegasys and Ribavirin | Interferon | PEGylated IFN-α2a/ribavirin | F. Hoffmann-La Roche LTD, Basel, Switzerland |
| PEG-Intron | Interferon | PEGylated IFN-α2b | Schering-Plough Corporation, Kenilworth, NJ |
| PEG-Intron/ Ribavirin | Interferon | PEGylated IFN-α2b/ribavirin | Schering-Plough Corporation, Kenilworth, NJ |
| IP-501 | Liver protection | antifibrotic | Indevus Pharmaceuticals Inc., Lexington, MA |
| IDN-6556 | Liver protection | caspase inhibitor | Idun Pharmaceuticals Inc., San Diego, CA |
| ITMN-191 (R-7227) | Antiviral | serine protease inhibitor | InterMune Pharmaceuticals Inc., Brisbane, CA |
| GL-59728 | Antiviral | NS5B Replicase Inhibitor | Genelabs |
| ANA-971 | Antiviral | TLR-7 agonist | Anadys |
| Boceprevir | Antiviral | serine protease inhibitor | Schering Plough |
| TMS-435 | Antiviral | serine protease inhibitor | Tibotec BVBA, Mechelen, Belgium |
| BI-201335 | Antiviral | serine protease inhibitor | Boehringer Ingelheim Pharma KG, Ingelheim, Germany |
| MK-7009 | Antiviral | serine protease inhibitor | Merck |
| PF-00868554 | Antiviral | replicase inhibitor | Pfizer |
| ANA598 | Antiviral | Non-Nucleoside NS5B Polymerase Inhibitor | Anadys Pharmaceuticals, Inc., San Diego, CA, USA |
| IDX375 | Antiviral | Non-Nucleoside Replicase Inhibitor | Idenix Pharmaceuticals, Cambridge, MA, USA |
| BILB 1941 | Antiviral | NS5B Polymerase Inhibitor | Boehringer Ingelheim Canada Ltd R&D, Laval, QC, Canada |
| PSI-7851 | Antiviral | Nucleoside Polymerase Inhibitor | Pharmasset, Princeton, NJ, USA |
| PSI-7977 | Antiviral | Nucleotide NS5B Polymerase Inhibitor | Pharmasset, Princeton, NJ, USA |
| VCH-759 | Antiviral | NS5B Polymerase Inhibitor | ViroChem Pharma |

TABLE 1-continued

| Brand Name | Physiological Class | Type of Inhibitor or Target | Source Company |
|---|---|---|---|
| INX-189 | Antiviral | Nucleotide NS5B Polymerase Inhibitor | Inhibitex |
| VCH-916 | Antiviral | NS5B Polymerase Inhibitor | ViroChem Pharma |
| GS-9190 | Antiviral | NS5B Polymerase Inhibitor | Gilead |
| Peg-interferon lamda | Antiviral | Interferon | ZymoGenetics/Bristol-Myers Squibb |
| daclatasvir | Antiviral | NS5A inhibitor | Bristol-Myers Squibb |
| BMS-791325 | Antiviral | NS5B Polymerase Inhibitor | Bristol-Myers Squibb |
| ACH-3102 | Antiviral | NS5A inhibitor | Bristol-Myers Squibb |
| BMS-984478 | Antiviral | NS5A inhibitor | Bristol-Myers Squibb |
| asunaprevir | Antiviral | serine protease inhibitor | Bristol-Myers Squibb |

The compounds of the disclosure may also be used as laboratory reagents. Compounds may be instrumental in providing research tools for designing of viral replication assays, validation of animal assay systems and structural biology studies to further enhance knowledge of the HCV disease mechanisms. Further, the compounds of the present disclosure are useful in establishing or determining the binding site of other antiviral compounds, for example, by competitive inhibition.

The compounds of this disclosure may also be used to treat or prevent viral contamination of materials and therefore reduce the risk of viral infection of laboratory or medical personnel or patients who come in contact with such materials, e.g., blood, tissue, surgical instruments and garments, laboratory instruments and garments, and blood collection or transfusion apparatuses and materials.

This disclosure is intended to encompass compounds having formula (I) when prepared by synthetic processes or by metabolic processes including those occurring in the human or animal body (in vivo) or processes occurring in vitro.

The present disclosure will now be described in connection with certain embodiments which are not intended to limit its scope. On the contrary, the present disclosure covers all alternatives, modifications, and equivalents as can be included within the scope of the claims. Thus, the following examples, which include specific embodiments, will illustrate one practice of the present disclosure, it being understood that the examples are for the purposes of illustration of certain embodiments and are presented to provide what is believed to be the most useful and readily understood description of its procedures and conceptual aspects.

The abbreviations used in the present application, including particularly in the illustrative schemes and examples which follow, are well-known to those skilled in the art. Some of the abbreviations used are as follows: LAH for lithium aluminum hydride; MsCl for methanesulfonyl chloride; Ph for phenyl; THF for tetrahydrofuran; min for minutes; h or hr or hrs for hours; DCM for dichloromethane; Ts for toluenesulfonyl; DMAP for N,N-dimethylaminopyridine; tBuOK for potassium tert-butoxide; DMSO for N,N-dimethylsulfoxide; DIPEA for diisopropylethylamine; MeOH for methanol; r.t. or RT or Rt for room temperature or retention time (context will dictate); HATU for O-(7-azabenzotriazol-1-yl)-N,N,N',N'-tetramethyluronium phosphate; DCE for 1,2-dichloroethane; TBME or MTBE for methyl tert-butyl ether; EtOAC or EtOAc for ethyl acetate; pTSA for para-tolylsulfonic acid; BOC or Boc for tert-butoxycarbonyl; CDI for 1,1-carbonyldiimidazole; DBU for 1,8-diazabicyclo[5.4.0]undec-7-ene; TMS for trimethylsilane; DPPA for diphenylphosphoryl azide; OAc for acetate; Me for methyl; NBS for N-methylsuccinimide; and EtI for ethyl iodide.

The starting materials useful to synthesize the compounds of the present disclosure are known to those skilled in the art and can be readily manufactured or are commercially available.

The following methods set forth below are provided for illustrative purposes and are not intended to limit the scope of the claims. It will be recognized that it may be necessary to prepare such a compound in which a functional group is protected using a conventional protecting group then to remove the protecting group to provide a compound of the present disclosure. The details concerning the use of protecting groups in accordance with the present disclosure are known to those skilled in the art Compounds were named using ChemDraw.

Preparation of (2S,4R)-1-((2S,3R)-2-((tert-butoxycarbonyl)amino)-3-(methoxymethyl)-5-methylnon-8-enoyl)-4-hydroxypyrrolidine-2-carboxylic acid

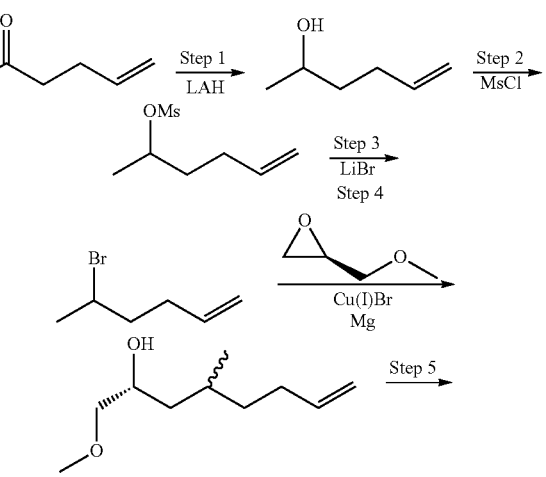

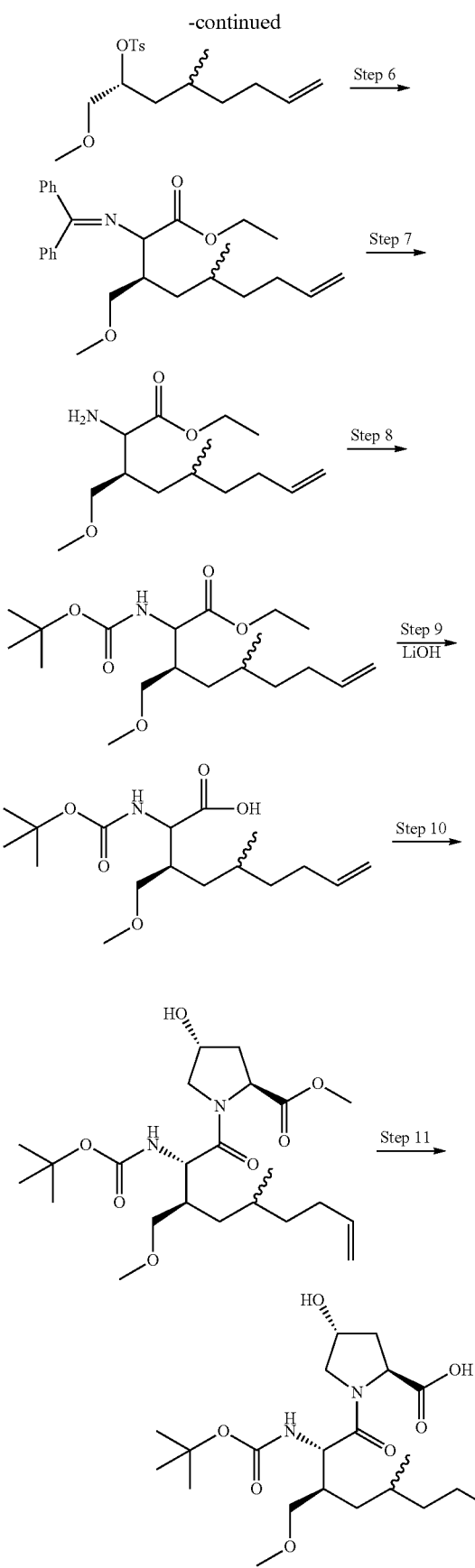

Step 1: Preparation of Hex-5-en-2-ol

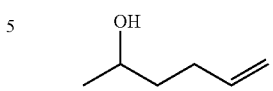

To a solution of lithium aluminum hydride in THF (LAH, 20.1 g, 106.12 mmol, 509 mL, 1M solution) was added a solution of hex-5-en-2-one (50 g, 102.04 mmol) over a period of 30 min. at −20° C. under nitrogen. The reaction mass was allowed to warm to room temperature and stirred for 1 h. The solution was cooled to −20° C. and to it was added aqueous 10% NaOH solution (~100 mL). The organic layer was separated and the aqueous layer was extracted with ether. The combined organics were dried over anhydrous sodium sulfate and concentrated to get crude compound Hex-5-en-2-ol as colorless liquid (50 g, 98%). $^1$H NMR (400 MHz, CDCl$_3$): δ ppm 5.87-5.02 (m, 1H), 4.99-4.95 (m, 2H), 3.81-3.83 (m, 1H), 2.17-2.13 (m, 2H), 1.58-1.53 (m, 2H), 1.20-1.19 (d, J=8 Hz, 3H).

Step 2: Preparation of Hex-5-en-2-yl methanesulfonate

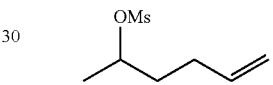

To a solution of Hex-5-en-2-ol (50 g crude, 500 mmole) in dichloromethane was added triethylamine (103 m 5 L, 750 mmol) at room temperature. The reaction mass was cooled to 0° C. and to it was added a solution of methane sulfonyl chloride (50.4 mL, 650 mmol) in DCM over a period of 30 min. The reaction mass was allowed to come to room temperature and stirred for 2 h. The solution was washed with water, dried over anhydrous sodium sulfate, filtered and concentrated under reduced pressure to get crude compound hex-5-en-2-yl methanesulfonate as light brown oily liquid (73 g, 82%). 1H NMR (400 MHz, CDCl$_3$): δ ppm 5.84-5.80 (m, 1H), 5.10-5.0 (m, 2H), 4.99-4.98 (m, 1H), 3.15 (s, 3H), 2.52-2.09 (m, 2H), 1.75-1.66 (m, 2H), 1.36-1.34 (d, J=6.4 Hz, 3H).

Step 3: Preparation of 5-bromohex-1-ene

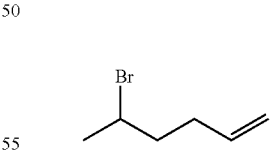

To a solution of hex-5-en-2-yl methanesulfonate (20 g, 0.112 moles) in dry THF (200 mL) was added LiBr (14.6 g, 0.168 moles) portion wise at room temperature over a period of 15 min. The reaction mass was heated at 70° C. for 3 h. The reaction mass was cooled to room temperature and was diluted with water (200 mL). The aqueous solution was extracted with ether (100 mL×3). The combined organics were dried over anhydrous Na$_2$SO$_4$ and concentrated at room temperature. The crude compound was distilled under reduced pressure at 115° C. to afford 5-bromohex-1-ene as colorless liquid (14.5 g, 80%). 1H NMR (400 MHz, CDCl$_3$):

δ ppm 5.80-5.74 (m, 1H), 5.08-4.98 (m, 2H), 4.14-4.09 (m, 1H), 2.28-2.17 (m, 2H), 1.94-1.81 (m, 2H), 1.71-1.70 (d, J=6.8 Hz, 3H); MS: GC-MS m/z 162.

Step 4: Preparation of (2R)-1-methoxy-4-methyloct-7-en-2-ol

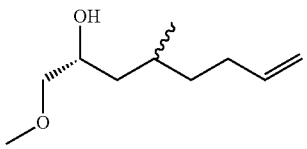

To magnesium turnings (4.14 g, 170 mmole) in dry THF (140 mL) and was added an iodine (10 mg) at room temperature. To this reaction mass was added a solution of 5-bromohex-1-ene (27.8 g, 170 mmole) in THF (200 mL). The reaction mass was heated with hot air gun to initiate the reaction. Upon completion of the reaction the solution was transferred by cannula to a solution of (R)-2-(methoxymethyl)oxirane (10 g, 114 mmol) and copper bromide (1.62 g, 11.35 mmol) in THF (100 mL) at −78° C. The reaction mass was allowed to come to room temperature and was stirred overnight. The reaction mass was quenched with saturated aq. ammonium chloride solution and extracted with diethyl ether (200 mL×3). The combined organic layers were dried over anhydrous $Na_2SO_4$ and concentrated at room temperature to get crude compound. The crude compound was purified by column chromatography (Silica gel, 10% TBME in pet ether) to get (2R)-1-methoxy-4-methyloct-7-en-2-ol (16 g, 82%) as an oil.

Step 5: Preparation of (2R)-1-methoxy-4-methyloct-7-en-2-yl 4-methylbenzenesulfonate

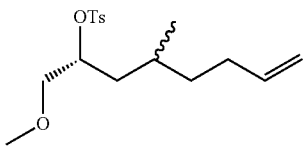 [SMILES: C=CCCC(C)C[C@H](COC)OS(=O)(=O)c1ccc(C)cc1]

To a solution of (2R)-1-methoxy-4-methyloct-7-en-2-ol (15 g, 87 mmole) in DCM (150 mL) was added pyridine (36 mL, 435 mmol) followed by 4-(dimethylamino)pyridine (DMAP, 1.06 g, 8.71 mmol) and the solution was stirred for 10 min. p-toluenesulfonyl chloride (18.26 g, 96 mmol) was added to the reaction mass at 0° C. The reaction mass was allowed to come to room temperature and stirred overnight. The reaction mass was washed with aqueous 1.5 N HCl solution, saturated aq. sodium bicarbonate solution, brine solution, dried over anhydrous $Na_2SO_4$, filter, and concentrated under reduced pressure to get crude compound (2R)-1-methoxy-4-methyloct-7-en-2-yl 4-methylbenzenesulfonate (18 g, 63%). The crude compound was taken to the next step without further purification.

Step 6: Preparation of (3R)-ethyl 2-((diphenylmethylene)amino)-3-(methoxymethyl)-5-methylnon-8-enoate

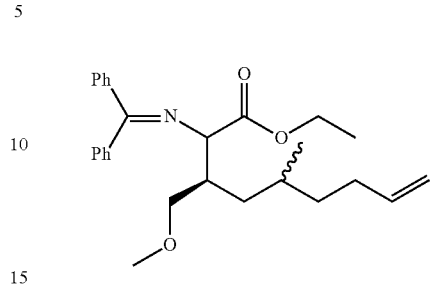

To a solution of (2R)-1-methoxy-4-methyloct-7-en-2-yl 4-methylbenzenesulfonate (15.88 g, 48.6 mmole) and N-(diphenylmethylene)glycinate ethyl ester (13 g, 48.6 moles) in toluene (500 mL) was added t-BuOK (72.9 mL, 72.9 mmole, 1 M solution in THF) at room temperature. The reaction mass was allowed to come to room temperature and was then heated at 110° C. for 18 h. The reaction mass was cooled to room temperature and quenched aqueous citric acid solution. The organic layers were dried over anhydrous $Na_2SO_4$ and concentrated under reduced pressure to get crude compound (14 g, 41%). The crude compound was taken to the next step without further purification. MS: MS m/z 423.65 ($M^+$+1).

Step 7: Preparation of (3R)-ethyl 2-amino-3-(methoxymethyl)-5-methylnon-8-enoate

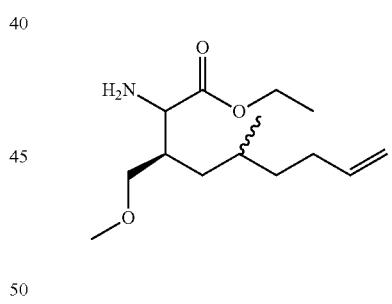

To a solution of (3R)-ethyl 2-((diphenylmethylene)amino)-3-(methoxymethyl)-5-methylnon-8-enoate (14 g, 33.2 mmol) in diethyl ether (50 mL) was added aqueous 1.5 N HCl solution (200 mL) and the reaction mass was stirred at room temperature overnight. The reaction mass was washed with diethyl ether (100 mL). The aqueous solution was basified using saturated sodium bicarbonate solution and was extracted with ethyl acetate (100 mL×3). The combined organic layers were dried over anhydrous $Na_2SO_4$, filtered, and concentrated under reduced pressure to get crude compound (4.8 g, 47.7%). The crude compound was taken to the next step without further purification.

Step 8: Preparation of (3R)-ethyl 2-((tert-butoxycarbonyl)amino)-3-(methoxymethyl)-5-methylnon-8-enoate

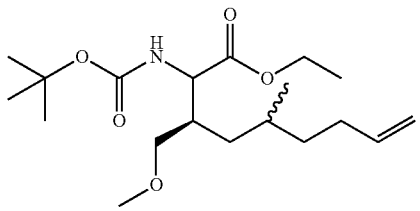 [SMILES: C=CCCC(C)C[C@@H](COC)C(NC(=O)OC(C)(C)C)C(=O)OCC]

A solution of (3R)-ethyl 2-amino-3-(methoxymethyl)-5-methylnon-8-enoate hydrochloride (4.8 g, 18.6 mmole) in DCM (40 mL) was added N,N-diisopropylethylamine (6.5 mL, 37.3 mmole) followed by di-tert-butyl dicarbonate (6.5 mL, 28 mmole) at room temperature. The reaction mass was stirred at room temperature overnight. The reaction mass was diluted with DCM and washed with water. The organic layer was dried over anhydrous $Na_2SO_4$, filtered, and concentrated under reduced pressure to afford the crude compound. The crude compound was purified by column chromatography (Silica gel, 20% ethyl acetate in pet-ether) to get 4.9 g, (66%) of (3R)-ethyl 2-((tert-butoxycarbonyl)amino)-3-(methoxymethyl)-5-methylnon-8-enoate as an oil. $^1$H NMR (400 MHz, DMSO-$d_6$): δ ppm 5.8 (m, 1H), 5.5 (m, 1H), 5.1-4.9 (m, 2H), 4.3 m, 1H), 4.1 (m, 2H), 3.3 (s, 3H), 3.4 (m, 2H), 2.3 (m, 1H), 2.1 (m, 2H), 1.5 (s, 9H), 1.3 (m, 6H), 0.9 (m, 4H).

Step 9: Preparation of (3R)-2-((tert-butoxycarbonyl)amino)-3-(methoxymethyl)-5-methylnon-8-enoic acid

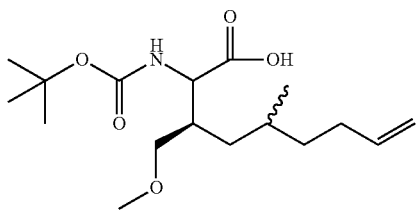 [SMILES: C=CCCC(C)C[C@@H](COC)C(NC(=O)OC(C)(C)C)C(=O)O]

To a solution of (3R)-ethyl 2-((tert-butoxycarbonyl)amino)-3-(methoxymethyl)-5-methylnon-8-enoate (4.9 g, 13.7 mmole) in THF/water (50 mL, 1:1) was added methanol (10 mL) followed by LiOH (0.98 g, 41 mmole) at room temperature. The reaction mass was stirred at room temperature overnight. The solution was concentrated under reduced pressure and the residue was diluted with water (50 mL). The aqueous solution was acidified with aqueous 1.5 N HCl solutions to pH ~3 and extracted with ethyl acetate (15 mL×3). The combined organic layers were dried over anhydrous $Na_2SO_4$ and concentrated under reduce pressure to get crude compound. The crude compound was purified by column chromatography (Silica gel, 3% methanol in DCM) to get (3R)-2-(tert-butoxycarbonylamino)-3,5-dimethylnon-8-enoic acid (4 g, 84%) of as gummy liquid. $^1$H NMR (400 MHz, DMSO-$d_6$): δ ppm 12.4 (sb, 1H), 6.72-6.65 (m, 1H), 5.81-5.75 (m, 1H), 5.04-4.93 (m, 2H), 4.12-3.91 (m, 1H), 3.6-3.10 (m, 8H), 2.18-1.98 (m, 2H), 1.5 (s, 9H), 1.35-1.02 (m, 2H), 1.0 (m, 1H), 0.98-0.85 (m, 3H).

Step 10: Preparation of (2S,4R)-methyl 1-((2S,3R)-2-((tert-butoxycarbonyl)amino)-3-(methoxymethyl)-5-methylnon-8-enoyl)-4-hydroxypyrrolidine-2-carboxylate

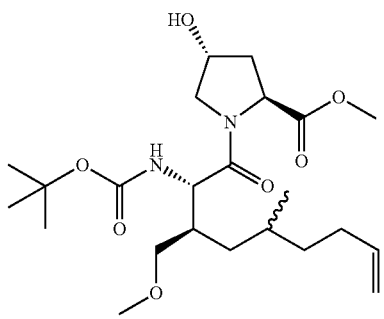 [SMILES: C=CCCC(C)C[C@@H](COC)[C@H](NC(=O)OC(C)(C)C)C(=O)N1C[C@H](O)C[C@H]1C(=O)OC]

O-(7-Azabenzotriazol-1-yl)-N,N,N',N'-tetramethyluronium hexafluorophosphate (HATU, 5.5 g, 14.5 mmol) was added to a solution of (2S,4R)-methyl 4-hydroxypyrrolidine-2-carboxylate HCl (2.65 g, 14.5 mmol), (3R)-2-((tert-butoxycarbonyl)amino)-3-(methoxymethyl)-5-methylnon-8-enoic acid (4 g, 12.14 mmol) and DIPEA (6.4 mL, 36.4 mmol) in DCM (40 mL) and stirred at RT for 16 h. The reaction was washed with 1N HCl and then brine solutions. The organics were dried with magnesium sulfate, filtered and concentrated under vacuum. The crude material was purified via silica gel chromatography using 20-60% acetone in hexanes to give the desired product (2S,4R)-methyl 1-((2S,3R)-2-((tert-butoxycarbonyl)amino)-3,5-dimethylnon-8-enoyl)-4-hydroxypyrrolidine-2-carboxylate (10.8 g, 30% yield), MS: MS m/z 427.2 (M$^+$+1) and the undesired product (2S,4R)-methyl 1-((2S,3R)-2-((tert-butoxycarbonyl)amino)-3-(methoxymethyl)-5-methylnon-8-enoyl)-4-hydroxypyrrolidine-2-carboxylate (1.4 g, 24%), MS: MS m/z 457.5 (M$^+$+1).

Step 11: Preparation of (2S,4R)-1-((2S,3R)-2-((tert-butoxycarbonyl)amino)-3-(methoxymethyl)-5-methylnon-8-enoyl)-4-hydroxypyrrolidine-2-carboxylic acid

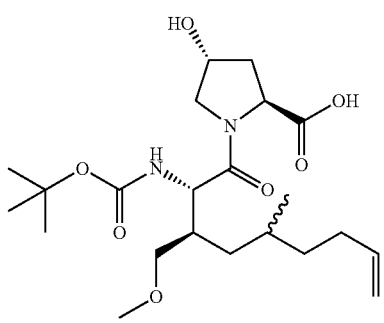 [SMILES: C=CCCC(C)C[C@@H](COC)[C@H](NC(=O)OC(C)(C)C)C(=O)N1C[C@H](O)C[C@H]1C(=O)O]

(2S,4R)-methyl 1-((2S,3R)-2-((tert-butoxycarbonyl)amino)-3-(methoxymethyl)-5-methylnon-8-enoyl)-4-hydroxypyrrolidine-2-carboxylate (1.4 g, 3.07 mmol) was dissolved in THF (20 mL), MeOH (5 mL) and to this solution was added LiOH (0.22 g, 24 mmol) in water (20.0 mL). The reaction mixture was stirred at rt for 16 h. The solvent was removed under vacuum and the resulting aqueous residue was diluted with water, and EtOAc. The mixture was neutralized with 1 N HCl and adjusted the pH ~2.5 and the mixture was extracted with EtOAc. The organic layer was collected, washed with brine, dried over Na$_2$SO$_4$, and concentrated to give (2S,4R)-1-((2S,3R)-2-((tert-butoxycarbonyl)amino)-3-(methoxymethyl)-5-methylnon-8-enoyl)-4-hydroxypyrrolidine-2-carboxylic acid (1.2 g, 80%) as yellow viscous oil. MS: MS m/z 443.45 (M$^+$+1).

Scheme: Synthesis of tert-butyl ((2R,6S,7R,13aS,14aR,16aS,Z)-14a-((cyclopropylsulfonyl)carbamoyl)-2-hydroxy-7-(methoxymethyl)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate

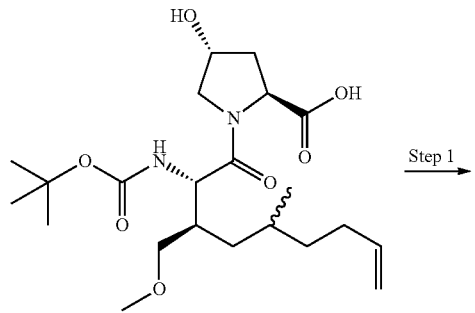

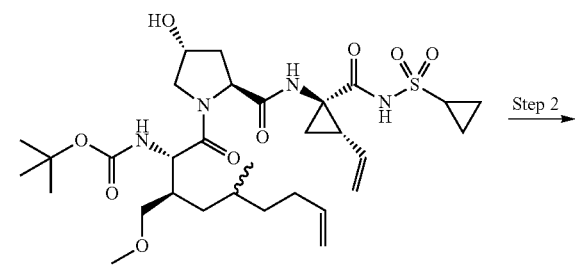

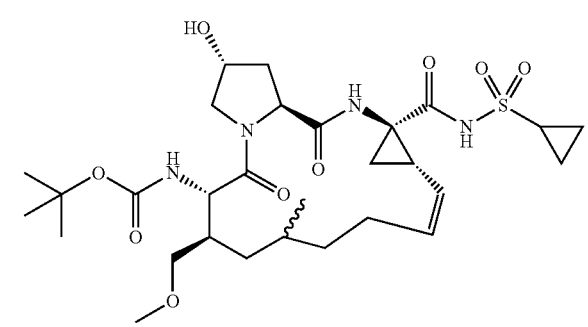 [SMILES: COC[C@@H]1CC(C)CC/C=C\[C@@H]2C[C@@]2(C(=O)NS(=O)(=O)C2CC2)NC(=O)[C@@H]2C[C@@H](O)CN2C(=O)[C@H]1NC(=O)OC(C)(C)C]

Step 1: Preparation of tert-butyl ((2S,3R)-1-((2S,4R)-2-(((1R,2S)-1-((cyclopropylsulfonyl)carbamoyl)-2-vinylcyclopropyl)carbamoyl)-4-hydroxypyrrolidin-1-yl)-3-(methoxymethyl)-5-methyl-1-oxonon-8-en-2-yl)carbamate

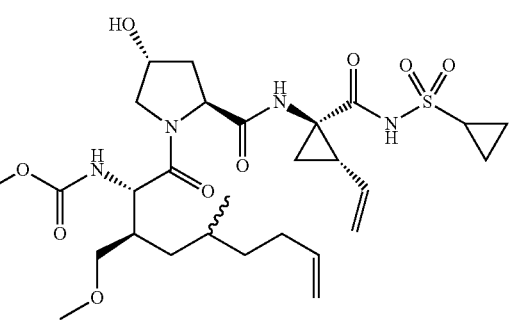

HATU (0.62 g, 1.62 mmol) was added to a solution of (2S,4R)-1-((2S,3R)-2-((tert-butoxycarbonyl)amino)-3-(methoxymethyl)-5-methylnon-8-enoyl)-4-hydroxypyrrolidine-2-carboxylic acid (0.6 g, 1.35 mmol), (1R,2S)-1-amino-N-(cyclopropylsulfonyl)-2-vinylcyclopropanecarboxamide (3.75 g, 1.62 mmol), and DIPEA (4.0 mL, 76 mmol) in DCM (25 mL). The reaction mixture was stirred at rt for 16 h. The mixture was washed with 1N HCl and then brine solution. The organic layer was collected, dried over sodium sulfate, and concentrated under vacuum. The crude material was purified by silica gel chromatography using a gradient of 20-60% acetone in hexanes. The product fractions were collected and the solvent removed under vacuum to give tert-butyl ((2S,3R)-1-((2S,4R)-2-(((1R,2S)-1-((cyclopropylsulfonyl)carbamoyl)-2-vinylcyclopropyl)carbamoyl)-4-hydroxypyrrolidin-1-yl)-3-(methoxymethyl)-5-methyl-1-oxonon-8-en-2-yl)carbamate (0.6 g, 61%). MS: MS m/z 655.6 (M$^+$+1).

Step 2: Preparation of tert-butyl ((2R,6S,7R,13aS,14aR,16aS,Z)-14a-((cyclopropylsulfonyl)carbamoyl)-2-hydroxy-7-(methoxymethyl)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate A solution of tert-butyl ((2S,3R)-1-((2S,4R)-2-(((1R,2S)-1-((cyclopropylsulfonyl)carbamoyl)-2-vinylcyclopropyl)carbamoyl)-4-hydroxypyrrolidin-1-yl)-3-(methoxymethyl)-5-methyl-1-oxonon-8-en-2-yl)carbamate (0.6 g, 0.92 mmol) in DCE (100 ml) was degassed with nitrogen for 30 min. and then (1,3-Bis-(2,4,6-trimethylphenyl)-2-imidazolidinylidene)dichloro(o-isopropoxyphenylmethylene)ruthenium), ("Hoveyda-Grubbs Catalyst 2nd Generation", 0.078 g, 0.092 mmol) was added. The reaction solution was heated to 80° C. for 4 h. The reaction solution was concentrated in vacuo and the resulting residue was purified by silica gel chromatography using a gradient of 20-60% acetone in hexanes to give the mixture of diastereomers as a brown solid (0.410 g, 71% yield). MS: MS m/z 627.6 (M$^+$+1).

Scheme: Synthesis of tert-butyl ((2R,6S,7R,13aS,14aR,16aS,Z)-2-hydroxy-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate

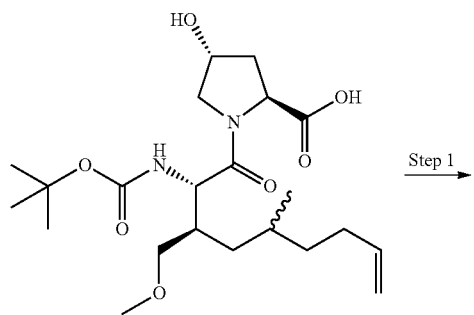

Step 1: Preparation of tert-butyl ((2S,3R)-1-((2S,4R)-4-hydroxy-2-(((1R,2S)-1-(((1-methylcyclopropyl)sulfonyl)carbamoyl)-2-vinylcyclopropyl)carbamoyl)pyrrolidin-1-yl)-3-(methoxymethyl)-5-methyl-1-oxonon-8-en-2-yl)carbamate

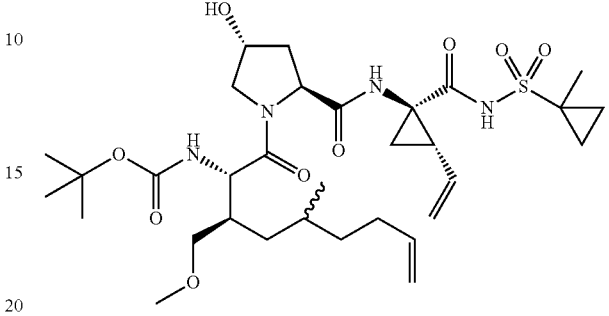

HATU (0.516 g, 1.35 mmol) was added to a solution of (2S,4R)-1-((2S,3R)-2-((tert-butoxycarbonyl)amino)-3,5-dimethylnon-8-enoyl)-4-hydroxypyrrolidine-2-carboxylic acid (0.5 g, 1.13 mmol), (1R,2S)-1-amino-N-((1-methylcyclopropyl)sulfonyl)-2-vinylcyclopropanecarboxamide hydrochloride (0.331 g, 1.35 mmol), and DIPEA (0.6 mL, 3.4 mmol) in DCM (20 mL). The reaction mixture was stirred at rt for 16 h. The mixture was washed with 1 N HCl, and then brine solution. The organic layer was collected, dried over sodium sulfate, and concentrated under vacuum. The crude material was purified by silica gel chromatography using a gradient of 20-60% acetone in hexanes. The product fractions were collected and the solvent removed under vacuum to give tert-butyl ((2S,3R)-1-((2S,4R)-4-hydroxy-2-(((1R,2S)-1-(((1-methylcyclopropyl)sulfonyl)carbamoyl)-2-vinylcyclopropyl)carbamoyl)pyrrolidin-1-yl)-3-(methoxymethyl)-5-methyl-1-oxonon-8-en-2-yl)carbamate (0.51, 57%). MS: MS m/z 669.6 (M$^+$+1).

Step 2: Preparation of tert-butyl ((2R,6S,7R,13aS,14aR,16aS,Z)-2-hydroxy-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate

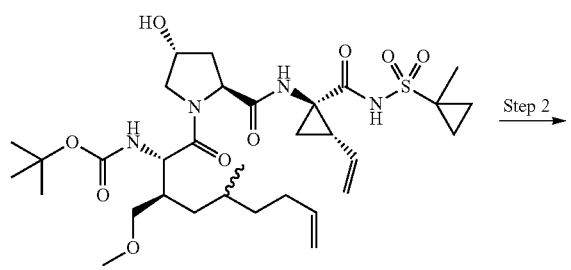

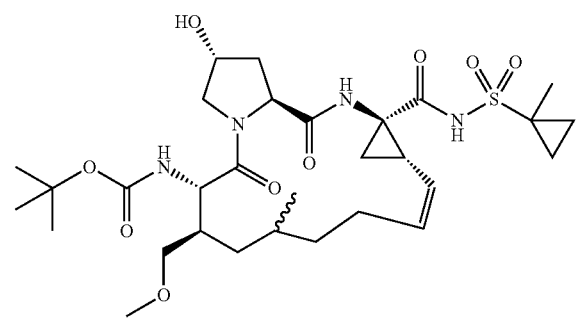

A solution of tert-butyl ((2S,3R)-1-((2S,4R)-4-hydroxy-2-(((1R,2S)-1-(((1-methylcyclopropyl)sulfonyl)carbamoyl)-2-vinylcyclopropyl)carbamoyl)pyrrolidin-1-yl)-3-(methoxymethyl)-5-methyl-1-oxonon-8-en-2-yl)carbamate (0.5 g, 0.75 mmol) in DCE (100 ml) was degassed with nitrogen for 30 min. and then (1,3-Bis-(2,4,6-trimethylphenyl)-2-imidazolidinylidene)dichloro(o-isopropoxyphenylmethylene)ruthenium) ("Hoveyda-Grubbs Catalyst 2nd Generation", 0.06 g, 0.07 mmol) was added. The reaction solution was heated to 80° C. for 25. The reaction solution was concentrated in vacuo the and resulting residue was purified by silica gel chromatography using a gradient of 20-60% acetone in hexanes to give the mixture of diastereomers as a brown solid (0.37 g, 76% yield). MS: MS m/z 641.6 (M$^+$+1).

Scheme: Synthesis of tert-butyl ((2R,6S,7R,13aS,14aR,16aS,Z)-14a-(((1-fluoromethyl)cyclopropyl)sulfonyl)carbamoyl)-2-hydroxy-7-(methoxymethyl)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate

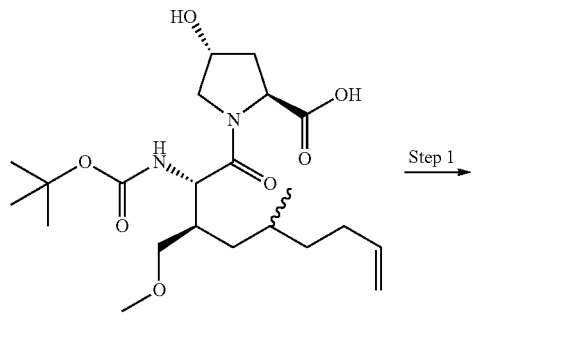

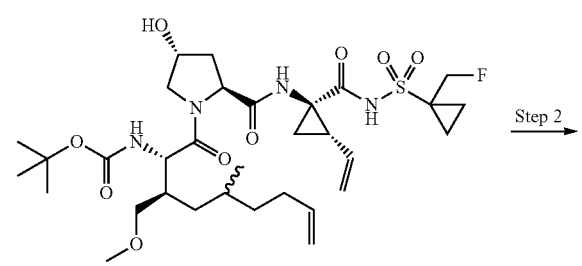

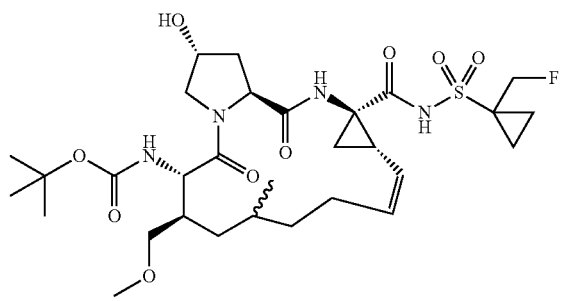

Step 1: Preparation of tert-butyl ((2S,3R)-1-((2S,4R)-2-(((1R,2S)-1-(((1-(fluoromethyl)cyclopropyl)sulfonyl)carbamoyl)-2-vinylcyclopropyl)carbamoyl)-4-hydroxypyrrolidin-1-yl)-3-(methoxymethyl)-5-methyl-1-oxonon-8-en-2-yl)carbamate

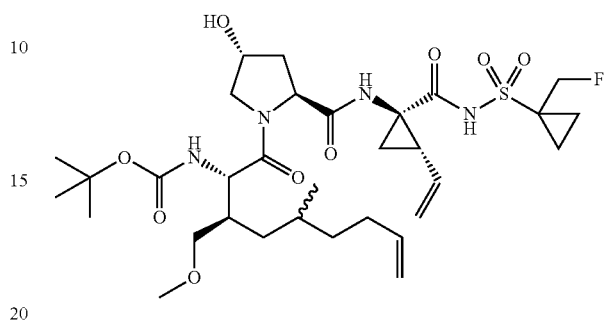

HATU (0.56 g, 1.46 mmol) was added to a solution of (2S,4R)-1-((2S,3R)-2-((tert-butoxycarbonyl)amino)-3,5-dimethylnon-8-enoyl)-4-hydroxypyrrolidine-2-carboxylic acid (0.5 g, 1.13 mmol), (1R,2S)-1-amino-N-((1-(fluoromethyl)cyclopropyl)sulfonyl)-2-vinylcyclopropanecarboxamide hydrochloride (0.445 g, 1.35 mmol), and DIPEA (0.6 mL, 3.3 mmol) in DCM (20 mL). The reaction mixture was stirred at rt for 16 h. The mixture was washed with 1N HCl, and then brine solutions. The organic layer was collected, dried over sodium sulfate, and concentrated under vacuum. The crude material was purified by silica gel chromatography using a gradient of 20-60% Acetone in hexanes. The product fractions were collected and the solvent removed under vacuum to give tert-butyl ((2S,3R)-1-((2S,4R)-2-(((1R,2S)-1-(((1-(fluoromethyl)cyclopropyl)sulfonyl)carbamoyl)-2-vinylcyclopropyl)carbamoyl)-4-hydroxypyrrolidin-1-yl)-3-(methoxymethyl)-5-methyl-1-oxonon-8-en-2-yl)carbamate (400 mg, 44%). MS: MS m/z 688.2 (M$^+$+1).

Step 2: Preparation of tert-butyl ((2R,6S,7R,13aS,14aR,16aS,Z)-14a-(((1-(fluoromethyl)cyclopropyl)sulfonyl)carbamoyl)-2-hydroxy-7-(methoxymethyl)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate

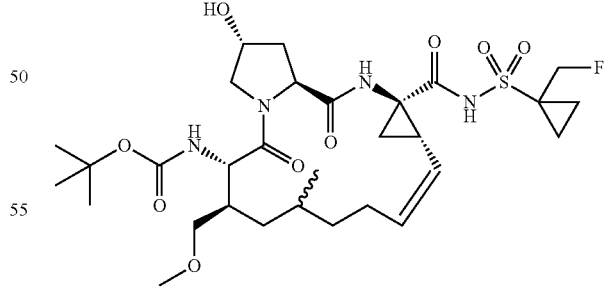

A solution of tert-butyl ((2S,3R)-1-(((2S,4R)-2-(((1R,2S)-1-(((1-(fluoromethyl)cyclopropyl)sulfonyl)carbamoyl)-2-vinylcyclopropyl)carbamoyl)-4-hydroxypyrrolidin-1-yl)-3-(methoxymethyl)-5-methyl-1-oxonon-8-en-2-yl)carbamate (0.35 g, 0.5 mmol) in DCE (100 ml) was degassed with nitrogen for 30 min. and then (1,3-Bis-(2,4,6-trimethylphenyl)-2-imidazolidinylidene)dichloro(o-isopropoxyphenylmethylene)ruthenium) ("Hoveyda-Grubbs Catalyst 2nd Generation", 0.022 g, 0.02 mmol) was added. The reaction solution was heated to 80° C. for 2 h. The reaction solution was concentrated in vacuum the and resulting residue was purified by silica gel chromatography using a gradient of 20-60% acetone in hexanes to give the mixture of diastereomers as a brown solid (0.15 g, 45% yield). MS: MS m/z 659.3 (M++1).

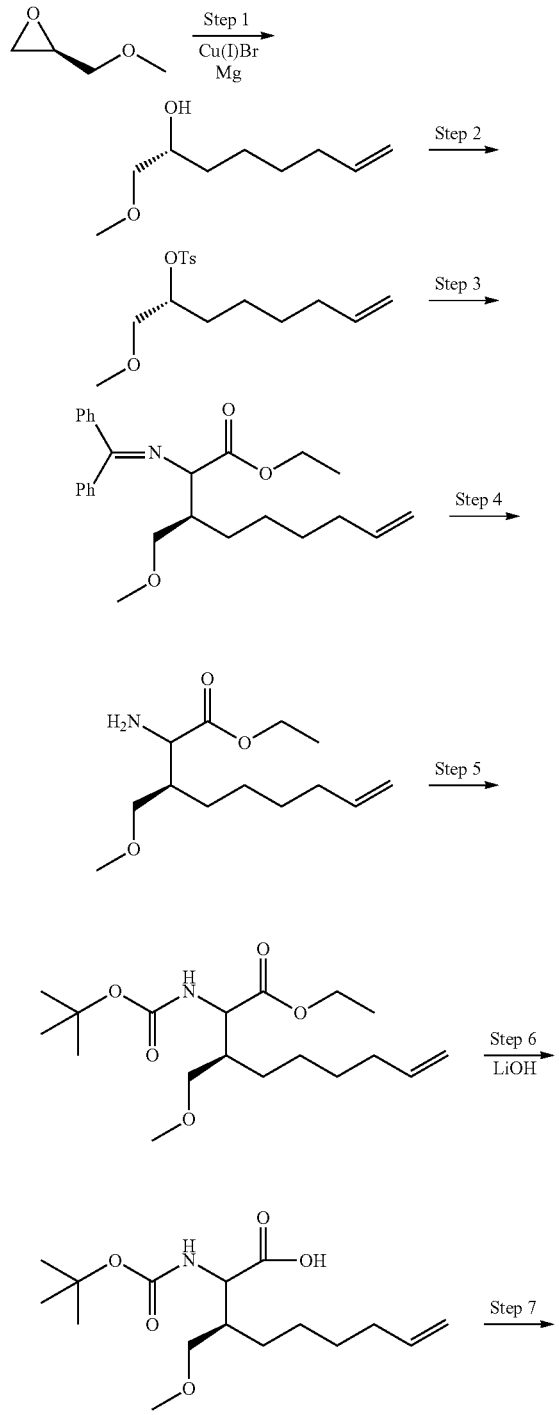

Scheme: Synthesis of (2S,4R)-1-((2S,3R)-2-((tert-butoxycarbonyl)amino)-3-(methoxymethyl)non-8-enoyl)-4-hydroxypyrrolidine-2-carboxylic acid

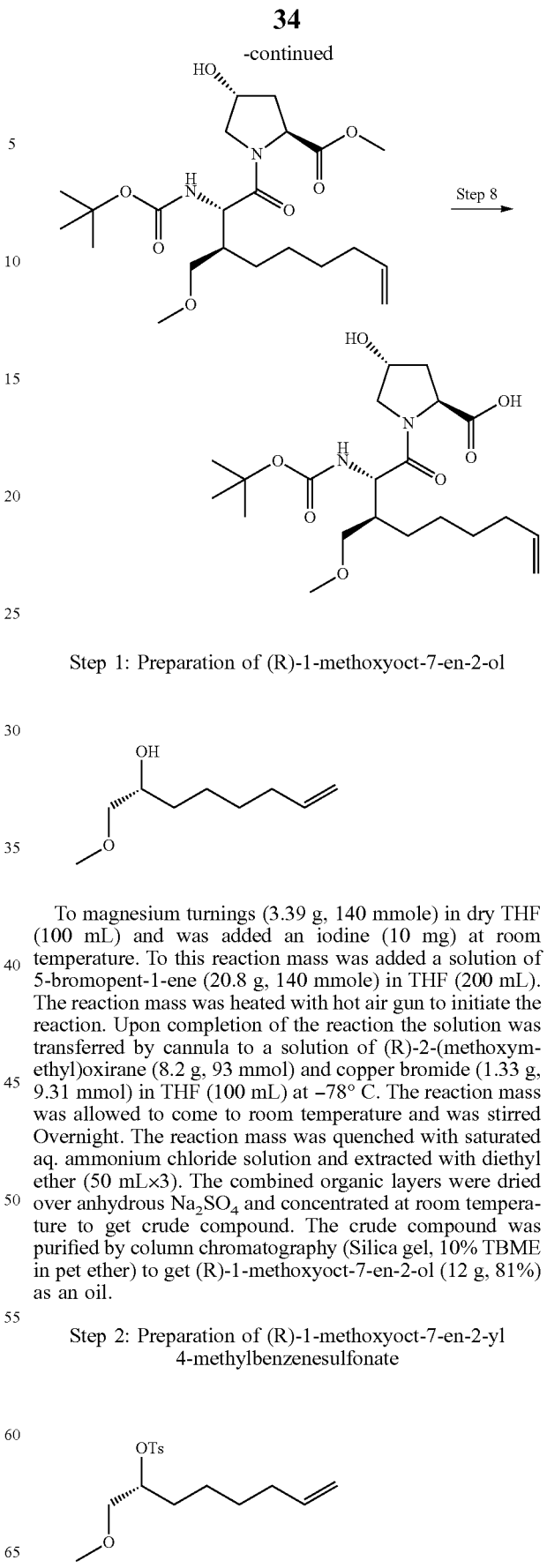

Step 1: Preparation of (R)-1-methoxyoct-7-en-2-ol

To magnesium turnings (3.39 g, 140 mmole) in dry THF (100 mL) and was added an iodine (10 mg) at room temperature. To this reaction mass was added a solution of 5-bromopent-1-ene (20.8 g, 140 mmole) in THF (200 mL). The reaction mass was heated with hot air gun to initiate the reaction. Upon completion of the reaction the solution was transferred by cannula to a solution of (R)-2-(methoxymethyl)oxirane (8.2 g, 93 mmol) and copper bromide (1.33 g, 9.31 mmol) in THF (100 mL) at −78° C. The reaction mass was allowed to come to room temperature and was stirred Overnight. The reaction mass was quenched with saturated aq. ammonium chloride solution and extracted with diethyl ether (50 mL×3). The combined organic layers were dried over anhydrous $Na_2SO_4$ and concentrated at room temperature to get crude compound. The crude compound was purified by column chromatography (Silica gel, 10% TBME in pet ether) to get (R)-1-methoxyoct-7-en-2-ol (12 g, 81%) as an oil.

Step 2: Preparation of (R)-1-methoxyoct-7-en-2-yl 4-methylbenzenesulfonate

To a solution of (R)-1-methoxyoct-7-en-2-ol (13 g, 82 mmole) in DCM (150 mL) was added pyridine (33.2 mL, 411 mmol) followed by 4-(dimethylamino)pyridine (DMAP, 1 g, 8.22 mmole) and the solution was stirred for 10 min. p-toluenesulfonyl chloride (17.23 g, 90 mmole) was added to the reaction mass at 0° C. The reaction mass was allowed to come to room temperature and stirred overnight. The reaction mass was washed with aqueous 1.5 N HCl solution, saturated aq. bicarbonate solution, brine solution, dried over anhydrous Na$_2$SO$_4$, filter, and concentrated under reduced pressure to get crude compound (R)-1-methoxyoct-7-en-2-yl 4-methylbenzenesulfonate (15 g, 58%). The crude compound was taken to the next step without further purification.

Step 3: Preparation of (3R)-ethyl 2-((diphenylmethylene)amino)-3-(methoxymethyl)non-8-enoate

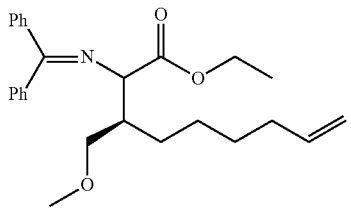 [SMILES: C=CCCCC[C@@H](COC)C(N=C(c1ccccc1)c1ccccc1)C(=O)OCC]

To a solution of (R)-1-methoxyoct-7-en-2-yl 4-methylbenzenesulfonate (10 g, 32 mmole) and N-(diphenylmethylene)glycinate ethyl ester (8.56 g, 32 mmole) in toluene (100 mL) was added t-BuOK (48 mL, 48 mmole, 1 M solution in THF) at 0° C. The reaction mass was allowed to come to room temperature and was heated at 110° C. for 4 h. The reaction mass was cooled to room temperature, quenched with water and extracted with ethyl acetate (200 mL×3). The combined organic layers were dried over anhydrous Na$_2$SO$_4$, filtered and concentrated under reduced pressure to get crude compound (3R)-ethyl 2-((diphenylmethylene)amino)-3-(methoxymethyl)non-8-enoate (11 g, 22%). The crude compound was taken to the next step without further purification.

Step 4: Preparation of (3R)-ethyl 2-amino-3-(methoxymethyl)non-8-enoate

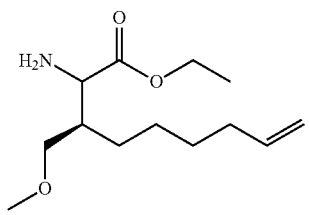 [SMILES: C=CCCCC[C@@H](COC)C(N)C(=O)OCC]

To a solution of (3R)-ethyl 2-((diphenylmethylene)amino)-3-(methoxymethyl)non-8-enoate (10 g, 25.54 mmol) in diethyl ether (20 mL) was added aqueous 1.5 N HCl solution (50 mL) and the reaction mass was stirred at room temperature overnight. The reaction mass was washed with diethyl ether (50 mL). The aqueous solution was basified using saturated sodium bicarbonate solution and was extracted with ethyl acetate (20 mL×3). The combined organic layers were dried over anhydrous Na$_2$SO$_4$, filtered, and concentrated under reduced pressure to get crude compound (3R)-ethyl 2-amino-3-(methoxymethyl)non-8-enoate hydrochloride (3 g, 50%). The crude compound was taken to the next step without further purification.

Step 5: Preparation of (3R)-ethyl 2-((tert-butoxycarbonyl)amino)-3-(methoxymethyl)non-8-enoate

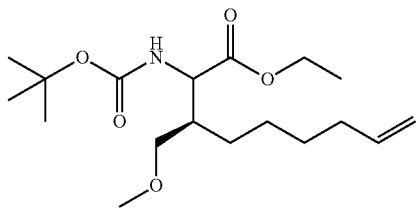 [SMILES: C=CCCCC[C@@H](COC)C(NC(=O)OC(C)(C)C)C(=O)OCC]

A solution of (3R)-ethyl 2-amino-3-(methoxymethyl)non-8-enoate hydrochloride (4 g, 0.017 moles) in DCM (40 mL) was added N,N-diisopropylethylamine (DIPEA, 5.7 mL, 0.033 moles) followed by di-tert-butyl dicarbonate (4.5 g, 0.020 moles) at room temperature. The reaction mass was stirred at room temperature overnight. The reaction mass was diluted with DCM and washed with water. The organic layer was dried over anhydrous Na$_2$SO$_4$, filtered, and concentrated under reduced pressure to afford the crude compound. The crude compound was purified by column chromatography (Silica gel, 20% ethyl acetate in pet-ether) to get (3R)-ethyl 2-amino-3-(methoxymethyl) non-8-enoate hydrochloride (5.1 g, 90%) as an oil.

Step 6: Preparation of (3R)-2-((tert-butoxycarbonyl)amino)-3-(methoxymethyl)non-8-enoic acid

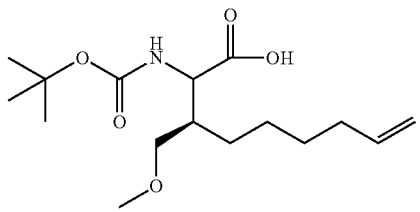 [SMILES: C=CCCCC[C@@H](COC)C(NC(=O)OC(C)(C)C)C(=O)O]

To a solution of (3R)-ethyl 2-((tert-butoxycarbonyl)amino)-3-(methoxymethyl)non-8-enoate (5 g, 0.014 moles) in THF/water (60 mL, 1:1) was added methanol (10 mL) followed by LiOH (1.4 g, 0.058 moles) at room temperature. The reaction mass was stirred at room temperature overnight. The solution was concentrated under reduced pressure and the residue was diluted with water (50 mL). The aqueous solution was acidified with aqueous 1.5 N HCl solution to pH ~3 and extracted with ethyl acetate (25 mL×3). The combined organic layers were dried over anhydrous Na$_2$SO$_4$ and concentrated under reduce pressure to get crude compound. The crude compound was purified by column chromatography (Silica gel, 3% methanol in DCM) to get 3.0 g (65%) of (3R)-2-((tert-butoxycarbonyl)amino)-3-(methoxymethyl)non-8-enoic acid as gummy liquid. $^1$H NMR (400 MHz, DMSO-d6): δ PPM 12.4 (sb, 1H), 6.82-6.65 (m, 1H), 5.81-5.75 (m, 1H), 5.04-4.93 (m, 2H), 4.12-3.91 (m, 1H), 3.31-3.14 (m, 3H), 2.10-1.9 (m, 5H), 1.4 (s, 9H), 1.35-1.15 (m, 6H).

Step 7: Preparation of (2S,4R)-methyl 1-((2S,3R)-2-((tert-butoxycarbonyl)amino)-3-(methoxymethyl)non-8-enoyl)-4-hydroxypyrrolidine-2-carboxylate

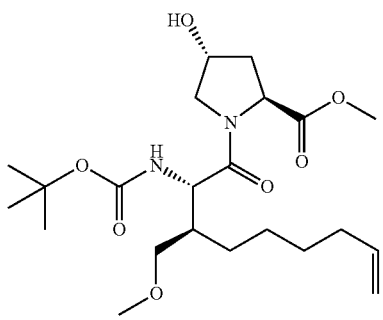 [SMILES: C=CCCCC[C@@H](COC)[C@H](NC(=O)OC(C)(C)C)C(=O)N1C[C@H](O)C[C@H]1C(=O)OC]

O-(7-Azabenzotriazol-1-yl)-N,N,N',N'-tetramethyluronium hexafluorophosphate (HATU, 4.22 g, 11.1 mmol) was added to a solution of (2S,4R)-methyl 4-hydroxypyrrolidine-2-carboxylate HCl (2.0 g, 11.1 mmol), (3R)-2-((tert-butoxycarbonyl)amino)-3-(methoxymethyl)non-8-enoic acid (3.5 g, 11.1 mmol) and DIPEA (5.8 mL, 33.3 mmol) in DCM (50 mL) and stirred at RT for 16 h. The reaction was washed with 1N HCl and then brine solution. The organics were dried with magnesium sulfate, filtered and concentrated under vacuum. The crude material was purified via silica gel chromatography using 20-60% Acetone in hexanes to give the desired product (2S,4R)-methyl 1-((2S,3R)-2-((tert-butoxycarbonyl)amino)-3-(methoxymethyl)non-8-enoyl)-4-hydroxypyrrolidine-2-carboxylate (1.75 g, 11% yield), MS: MS m/z 443.4 (M$^+$+1).

Step 8: Preparation of (2S,4R)-1-((2S,3R)-2-((tert-butoxycarbonyl)amino)-3-(methoxymethyl)non-8-enoyl)-4-hydroxypyrrolidine-2-carboxylic acid

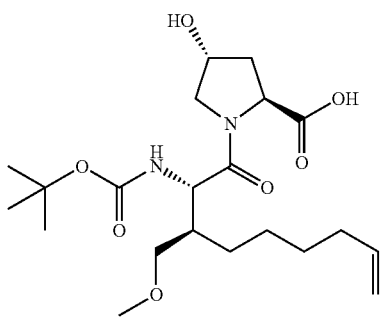 [SMILES: C=CCCCC[C@@H](COC)[C@H](NC(=O)OC(C)(C)C)C(=O)N1C[C@H](O)C[C@H]1C(=O)O]

(2S,4R)-methyl 1-((2S,3R)-2-((tert-butoxycarbonyl)amino)-3-(methoxymethyl)non-8-enoyl)-4-hydroxypyrrolidine-2-carboxylate (1.75 g, 3.9 mmol) was dissolved in THF (15 mL), MeOH (5 mL) and to this solution was added LiOH (0.38 g, 15.8 mmol) in water (15 mL). The reaction mixture was stirred at rt for 16 h. The solvent was removed under vacuum and the resulting aqueous residue was diluted with water, and EtOAc. The mixture was neutralized with 1 N HCl and adjusted the pH ~2.5 and the mixture was extracted with EtOAc. The organic layer was collected, washed with brine, dried over Na$_2$SO$_4$, and concentrated to give (2S,4R)-1-((2S,3R)-2-((tert-butoxycarbonyl)amino)-3-(methoxym- ethyl)non-8-enoyl)-4-hydroxypyrrolidine-2-carboxylic acid (1.25 g, 70% yield) as yellow viscous oil. MS: MS m/z 429.4 (M$^+$+1).

Scheme: Synthesis of tert-butyl ((2R,6S,7R,13aS,14aR,16aS,Z)-14a-((cyclopropylsulfonyl)carbamoyl)-2-hydroxy-7-(methoxymethyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate

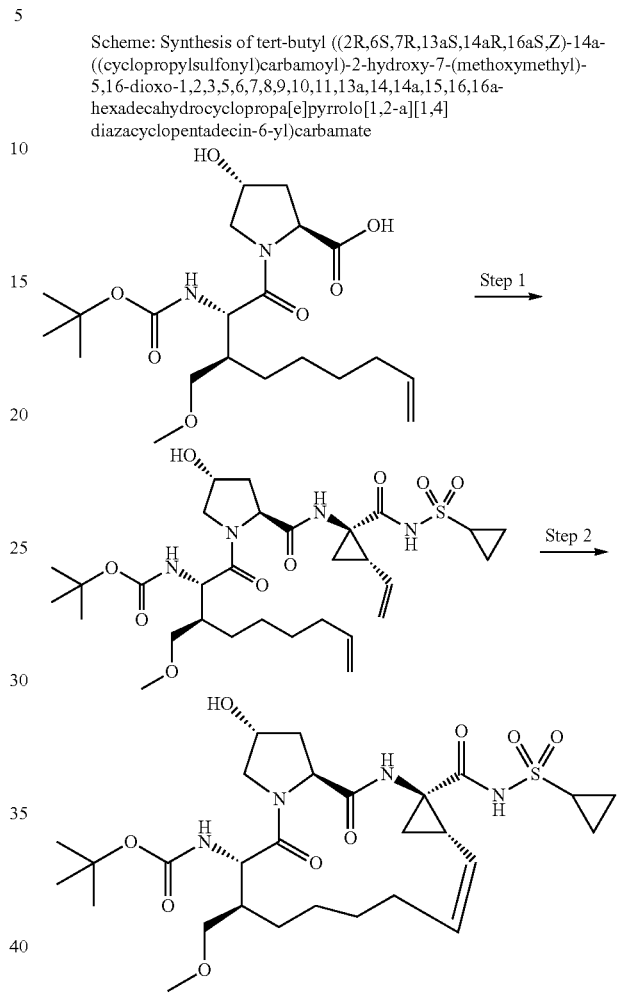

Step 1: Preparation of tert-butyl ((2S,3R)-1-((2S,4R)-2-(((1R,2S)-1-((cyclopropylsulfonyl)carbamoyl)-2-vinylcyclopropyl)carbamoyl)-4-hydroxypyrrolidin-1-yl)-3-(methoxymethyl)-1-oxonon-8-en-2-yl)carbamate

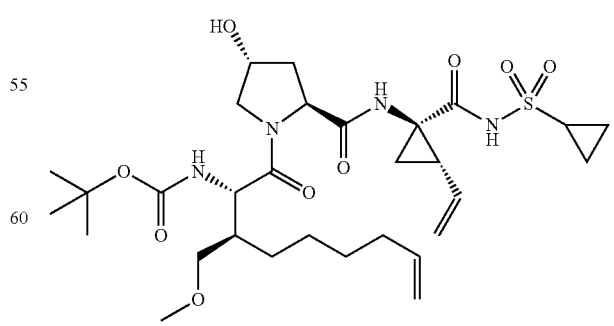

HATU (0.488 g, 1.28 mmol) was added to a solution of (2S,4R)-1-((2S,3R)-2-((tert-butoxycarbonyl)amino)-3-

(methoxymethyl)non-8-enoyl)-4-hydroxypyrrolidine-2-carboxylic acid (0.5 g, 1.16 mmol), (1R,2S)-1-amino-N-(cyclopropylsulfonyl)-2-vinylcyclopropanecarboxamide, pTSA (0.57 g, 1.28 mmol), and DIPEA (0.8 mL, 4.67 mmol) in DCM (30 mL). The reaction mixture was stirred at rt for 16 h. The mixture was washed with 1N HCl, and then brine. The organic layer was collected, dried over sodium sulfate, and concentrated under vacuum. The crude material was purified by silica gel chromatography using a gradient of 20-60% Acetone in hexanes. The product fractions were collected and the solvent removed under vacuum to give tert-butyl ((2S,3R)-1-((2S,4R)-2-(((1R,2S)-1-((cyclopropylsulfonyl)carbamoyl)-2-vinylcyclopropyl)carbamoyl)-4-hydroxypyrrolidin-1-yl)-3-(methoxymethyl)-1-oxonon-8-en-2-yl)carbamate (350 mg, 47%) as pale yellow gummy mass. MS: MS m/z 441.46 ($M^+$+1).

Step 2: Preparation of tert-butyl ((2R,6S,7R,13aS,14aR,16aS,Z)-14a-((cyclopropylsulfonyl)carbamoyl)-2-hydroxy-7-(methoxymethyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate

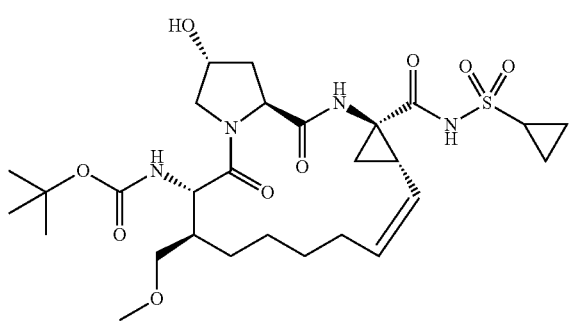 [SMILES: COC[C@@H]1CCCC/C=C\[C@@H]2C[C@@]2(C(=O)NS(=O)(=O)C2CC2)NC(=O)[C@@H]2C[C@@H](O)CN2C(=O)[C@H]1NC(=O)OC(C)(C)C]

A solution of tert-butyl ((2S,3R)-1-((2S,4R)-2-(((1R,2S)-1-((cyclopropylsulfonyl)carbamoyl)-2-vinylcyclopropyl)carbamoyl)-4-hydroxypyrrolidin-1-yl)-3-(methoxymethyl)-1-oxonon-8-en-2-yl)carbamate (0.35 g, 0.54 mmol) in DCE (50 ml) was degassed with nitrogen for 30 min. and then (1,3-Bis-(2,4,6-trimethylphenyl)-2-imidazolidinylidene)dichloro(o-isopropoxyphenylmethylene)ruthenium) ("Hoveyda-Grubbs Catalyst 2nd Generation", 0.046 g, 0.054 mmol) was added. The reaction solution was heated to 80° C. for 2 h. The reaction solution was concentrated in vacuum and the resulting residue was purified by silica gel chromatography using a gradient of 20-60% acetone in hexanes to give the mixture of diastereomers as a brown solid (0.2 g, 52% yield). MS: MS m/z 613.5 ($M^+$+1).

Scheme: Synthesis of tert-butyl ((2R,6S,7R,13aS,14aR,16aS,Z)-2-hydroxy-7-(methoxymethyl)-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate

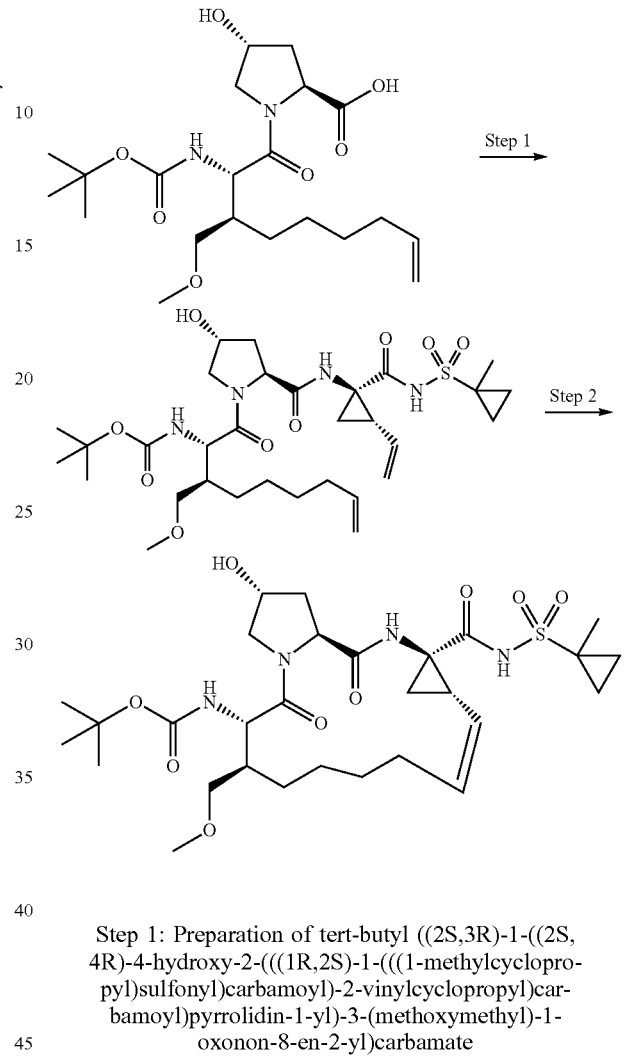

Step 1: Preparation of tert-butyl ((2S,3R)-1-((2S,4R)-4-hydroxy-2-(((1R,2S)-1-(((1-methylcyclopropyl)sulfonyl)carbamoyl)-2-vinylcyclopropyl)carbamoyl)pyrrolidin-1-yl)-3-(methoxymethyl)-1-oxonon-8-en-2-yl)carbamate

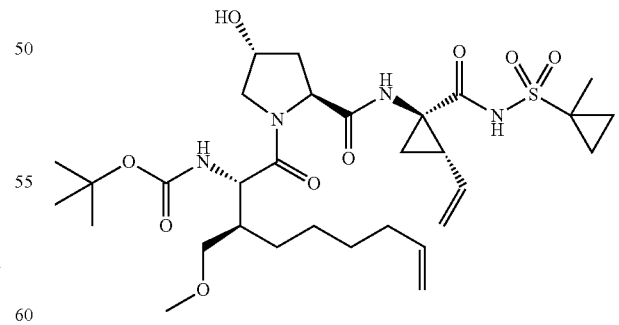

HATU (2.1 g, 5.6 mmol) was added to a solution of (2S,4R)-1-((2S,3R)-2-((tert-butoxycarbonyl)amino)-3-(methoxymethyl)non-8-enoyl)-4-hydroxypyrrolidine-2-carboxylic acid (2.0 g, 4.7 mmol), (1R,2S)-1-amino-N-((1-methylcyclopropyl)sulfonyl)-2-vinylcyclopropanecarboxamide (1.6 g, 5.6 mmol), and DIPEA (2.5 mL, 14 mmol) in DCM (25 mL). The reaction mixture was stirred at rt for 16 h. The mixture was washed with 1N HCl and then brine. The organic layer was collected, dried over sodium sulfate, and concentrated under vacuum. The crude material was purified by silica gel chromatography using a gradient of 20-60% Acetone in hexanes. The product fractions were collected and the solvent removed under vacuum to give ((2S,3R)-1-((2S,4R)-4-hydroxy-2-(((1R,2S)-1-(((1-methylcyclopropyl)sulfonyl)carbamoyl)-2-vinylcyclopropyl)carbamoyl)pyrrolidin-1-yl)-3-(methoxymethyl)-1-oxonon-8-en-2-yl)carbamate (1.5 g, 49%) as crystalline solid. MS: MS m/z 655.6 (M⁺+1).

Step 2: Preparation of tert-butyl ((2R,6S,7R,13aS,14aR,16aS,Z)-2-hydroxy-7-(methoxymethyl)-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate

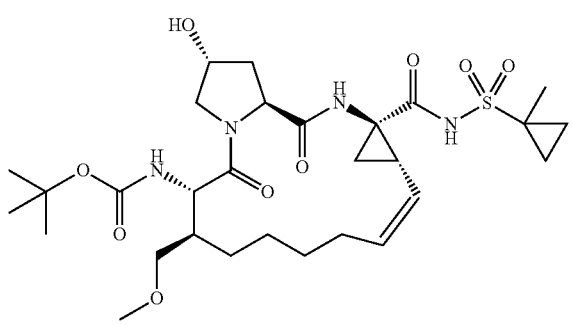 [SMILES: COC[C@@H]1CCCC/C=C\[C@@H]2C[C@@]2(C(=O)NS(=O)(=O)C2(C)CC2)NC(=O)[C@@H]2C[C@@H](O)CN2C(=O)[C@H]1NC(=O)OC(C)(C)C]

A solution of tert-butyl ((2S,3R)-1-((2S,4R)-4-hydroxy-2-(((1R,2S)-1-(((1-methylcyclopropyl)sulfonyl)carbamoyl)-2-vinylcyclopropyl)carbamoyl)pyrrolidin-1-yl)-3-(methoxymethyl)-1-oxonon-8-en-2-yl)carbamate (1.6 g, 2.44 mmol) in DCE (100 ml) was degassed with nitrogen for 30 min. and then (1,3-Bis-(2,4,6-trimethylphenyl)-2-imidazolidinylidene)dichloro(o-isopropoxyphenylmethylene)ruthenium) ("Hoveyda-Grubbs Catalyst 2nd Generation", 0.2 g, 0.02 mmol) was added. The reaction solution was heated to 80° C. for 2 h. The reaction solution was concentrated in vacuo the and resulting residue was purified by silica gel chromatography using a gradient of 20-60% Acetone in hexanes to give tert-butyl ((2R,6S,7R,13aS,14aR,16aS,Z)-2-hydroxy-7-(methoxymethyl)-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate (700 mg, 55%) as a brown solid (5.6 g, 70% yield). MS: MS m/z 627.55 (M⁺+1).

Preparation of (1R,2S)-1-amino-N-((1-(fluoromethyl)cyclopropyl)sulfonyl)-2-vinylcyclopropanecarboxamide hydrochloride

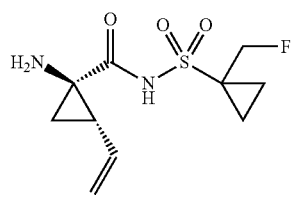 [SMILES: C=C[C@@H]1C[C@]1(N)C(=O)NS(=O)(=O)C1(CF)CC1]

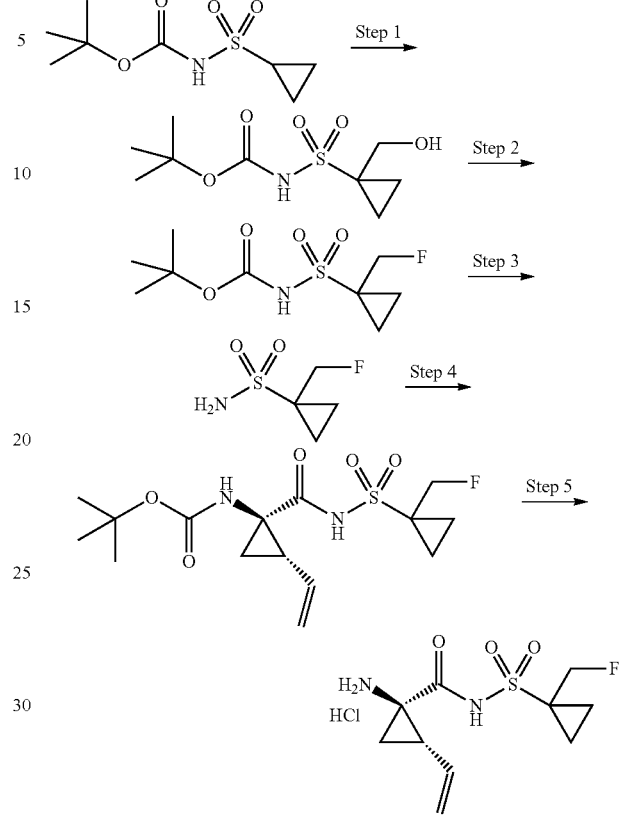

Step 1: Preparation of tert-butyl (1-(hydroxymethyl)cyclopropyl)sulfonylcarbamate To a solution of tert-butyl cyclopropylsulfonylcarbamate (30 g, 136 mmol) in 750 mL of THF was added dropwise butyllithium (1.6 M in hexane, 212 mL, 339 mmol) over 30 min at −78° C. and the resulting mixture was stirred at −78° C. for 1 h. Formaldehyde gas was generated from paraformaldehyde (by heating at 180° C.) and was purged in to the above reaction mass for 30 min at −30° C. The reaction was stirred at the same temperature for 1 h and then allowed to warm to room temperature. The reaction was quenched with aqueous ammonium chloride solution and diluted with water. The resulting mass was washed with ethyl acetate and the aqueous layer was acidified to pH ∼2 and extracted with ethyl acetate. The combined organics were dried over sodium sulfate and evaporated under reduced pressure to get desired compound (27 g, 79%) as white solid. ¹H NMR (400 MHz, DMSO-d₆): δ ppm 10.90 (sb, 1H), 4.95 (sb, 1H), 3.75 (s, 2H), 1.42 (s, 9H), 1.27 (m, 2H), 1.08 (m, 2H).

Step 2: Preparation of tert-butyl (1-(fluoromethyl)cyclopropyl)sulfonylcarbamate A solution of tert-butyl 1-hydroxymethylcyclopropylsulfonylcarbamate (26.0 g, 103 mmol) in DCM (300 mL) was cooled to −78° C. To this solution was added diethylaminosulfur trifluoride ("DAST", 41.0 mL, 310 mmol). The reaction mass was stirred at the same temperature for 30 min. The reaction mass was quenched with aqueous 1N NaOH solution. The organic layer was discarded and the aqueous layer was acidified to pH ~2 by using aq. 1.5 N HCl solutions. The aqueous solution was extracted with DCM (50 mL×4). The combined organic layers were dried over anhydrous sodium sulfate; filtered; then concentrated to afford desired tert-butyl (1-(fluoromethyl)cyclopropyl)sulfonylcarbamate (19 g, 72%) as gummy solid. $^1$H NMR (400 MHz, DMSO-d$_6$): δ ppm 11.25 (sb, 1H), 4.75 (s, 1H), 4.63 (s, 1H), 1.44 (s, 9H), 1.28 (m, 2H), 1.07 (m, 2H). $^{19}$F NMR: −211.7 (1F).

Step 3: Preparation of 1-(fluoromethyl)cyclopropane-1-sulfonamide

To a solution of tert-butyl 1-fluoromethyl cyclopropylsulfonylcarbamate (19 g, 75 mmol) in dichloromethane (200 mL) at room temperature was added trifluoroacetic acid ("TFA", 50 mL). The reaction mass was stirred at room temperature for 1 h. The solvent was evaporated under reduced pressure and the residue was diluted with hexane. The precipitated solid was isolated via filtration and washed with hexane to afford pure 1-(fluoromethyl)cyclopropane-1-sulfonamide (11 g, 96%) as an off-white solid. $^1$H NMR (400 MHz, DMSO-d$_6$): δ ppm 6.98 (sb, 2H), 4.75 (s, 1H), 4.63 (s, 1H), 1.28 (m, 2H), 1.08 (m, 2H). $^{19}$F NMR: −211.74 (1F).

Step 4: Preparation of tert-butyl (1R,2S)-1-(1-(fluoromethyl)cyclopropylsulfonylcarbamoyl)-2-vinylcyclopropylcarbamate To a solution of (1R,2S)-1-(tert-butoxycarbonylamino)-2-vinylcyclopropanecarboxylic acid (7.5 g, 33 mmol) in DMF (50 mL) was added 1,1'-carbonyldiimidazole ("CDI", 10.7 g, 66.0 mmol) and the reaction mass was heated at 55° C. for 4 h. To this reaction mass was added 1-fluoromethylcyclopropane-1-sulfonamide (6.5 g, 42.9 mmol) followed by 1,8-diazabicyclo[5.4.0]undec-7-ene ("DBU", 6.0 mL, 43 mmol). The reaction mixture was stirred at 55° C. for 18 h. The solvent was evaporated under reduced pressure and the residue was diluted with water and acidified to pH ~2 by using aq. 1.5 N HCl solutions. The precipitated solid was isolated via filtration and washed with water to afford tert-butyl (1R,2S)-1-(1-(fluoromethyl)cyclopropylsulfonylcarbamoyl)-2-vinylcyclopropylcarbamate as off-white solid (11.5 g, 96%). MS: MS m/z 361.4 (M$^+$−1).

Step 5: Preparation of (1R,2S)-1-amino-N-(1-(fluoromethyl)cyclopropylsulfonyl)-2-vinylcyclopropanecarboxamide hydrochloride A solution of tert-butyl (1R,2S)-1-(1-(fluoromethyl)cyclopropylsulfonylcarbamoyl)-2-vinylcyclopropylcarbamate (11.5 g, 31.7 mmol) in 4 N HCl in dioxane (100 mL) was stirred at room temperature for 1 h. The volatiles were removed under reduced pressure and the residue was washed with diethyl ether to afford crude (1R,2S)-1-amino-N-(1-(fluoromethyl)cyclopropylsulfonyl)-2-vinylcyclopropanecarboxamide hydrochloride (6 g, 72%). The crude compound was taken to the next step without further purification. MS: MS m/z 263.14 (M$^+$+1).

Scheme: Preparation of 1-methylcyclopropane-1-sulfonamide
Synthesis of 1-Methylcyclopropane-1-sulfonamide:

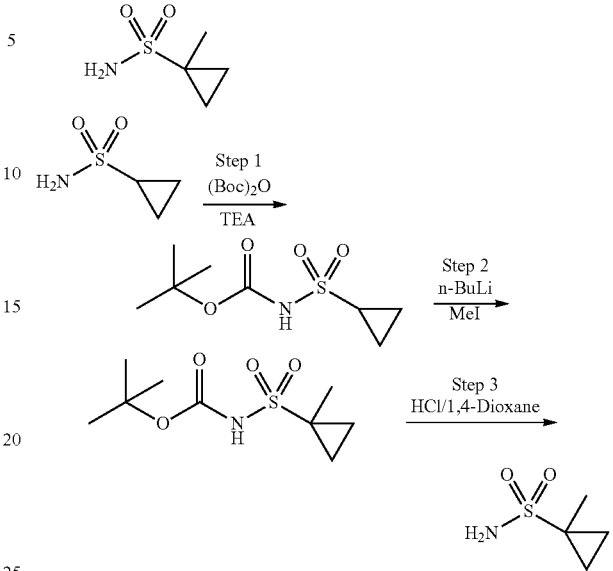

Step 1: Preparation of tert-butyl cyclopropylsulfonylcarbamate

To a solution of cyclopropanesulfonamide (100 g, 82.6 mmol) in DCM (800 ml) was added triethylamine (234 ml, 165 mmol) followed by DMAP (10.28 g, 82.6 mmol) at 0° C. under nitrogen. To this reaction mixture Boc anhydride (247 ml, 107 mmol) in DCM (400 ml) was added slowly. The resulting mixture was stirred for 4 h at room temperature. The reaction mixture was diluted with water and extracted with ethyl acetate. The combine organic layer was washed with 1.5 N HCl solution and 10% NaHCO$_3$ and dried over anhydrous sodium sulfate, filtered and evaporated under reduced pressure to get crude compound (143 g, 65%) as a solid. The crude compound was directly taken for the next step. $^1$H NMR (400 MHz, DMSO-d$_6$): δ ppm 11.08 (s, 1H), 2.90 (m, 1H), 1.48 (s, 9H), 1.06 (m, 4H).

Step 2: Preparation of tert-butyl(1-methylcyclopropyl) sulfonylcarbamate

A solution of tert-butyl cyclopropylsulfonylcarbamate (4.3 g, 20 mmol) was dissolved in dry THF (100 ml) and cooled to −78° C. To this solution was added n-BuLi (17.6 ml, 44 mmol, 2.5 M in hexane) slowly. The reaction mixture was allowed to warm to room temperature over a period of 1.5 h. This mixture was then cooled to −78° C., and a solution of n-BuLi (20 mmol, 8 ml, 2.5M in hexane) was added, stirred for 1 h and a neat solution of methyl iodide (5.68 g, 40 mmol) was added. The reaction mixture was allowed to warm to room temperature with stirring overnight; then was quenched with aqueous saturated NH$_4$Cl (100 ml) at room temperature. The mixture was extracted with EtOAc (100 ml). The organic layer was washed with brine; dried over Na$_2$SO$_4$, filtered and concentrated under reduced pressure to give a yellow oil which was crystallized from hexane to afford the product as a slightly yellow solid (3.1 g, 81%). $^1$H NMR (400 MHz, DMSO-d$_6$): δ ppm 10.97 (s, 1H), 1.44 (s, 12H), 1.35-1.33 (m, 2H), 0.93-0.91 (m, 2H).

Step 3: Preparation of 1-methylcyclopropane-1-sulfonamide

A solution of N-tert-butyl-(1-methyl)-cyclopropyl-sulfonamide (1.91 g, 10 mmol) was dissolved in 4M HCl in dioxane (30 ml) and the reaction mixture stirred at rt for 16 h. The solvent was removed in vacuo to give a yellow oil which was crystallized from EtOAc/hexane (1:4, 40 ml) to yield 1-methyl-cyclopropylsulfonamide, as a white solid (1.25 g, 96%). $^1$H NMR (400 MHz, CDCl$_3$): δ ppm 6.73 (s, 2H), 1.43 (s, 3H), 1.14-1.12 (m, 2H), 0.75-0.73 (m, 2H).

Preparation of tert-butyl ((1R,2S)-1-(((1-methylcyclopropyl)sulfonyl)carbamoyl)-2-vinylcyclopropyl)carbamate

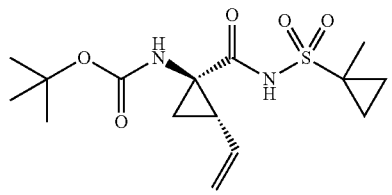 [SMILES: C=C[C@@H]1C[C@]1(NC(=O)OC(C)(C)C)C(=O)NS(=O)(=O)C1(C)CC1]

To a solution of (1R,2S)-1-(tert-butoxycarbonylamino)-2-vinylcyclopropanecarboxylic acid (25 g, 110 mmol) in THF (300 mL) was added CDI (205 g, 127 mmol) and the reaction mass was heated at 85° C. for 1 h. The reaction mass was cooled to rt and to this reaction mass was added 1-methylcyclopropane-1-sulfonamide (17.7 g, 131 mmol) followed by DBU (33.2 mL, 33.5 mmol). The reaction mixture was stirred at rt for 18 h. The solvent was evaporated under reduced pressure and the residue was diluted with water and acidified to pH ~2 by using aq. 1.5 N HCl solutions. The precipitated solid was isolated via filtration and washed with water to get desired compound (22 g, 58%) as off-white solid. $^1$H NMR (400 MHz, DMSO-d$_6$) δ ppm 11.01-11.17 (m, 1H), 7.17-7.33 (m, 1H), 5.35-5.51 (m, 1H), 5.18-5.29 (m, 1H), 4.99-5.09 (m, 1H), 2.21 (s, 1H), 1.69 (dd, J=7.78, 5.27 Hz, 1H), 1.40 (d, J=3.01 Hz, 14H), 1.20 (dd, J=9.29, 5.27 Hz, 1H), 0.82-0.96 (m, 2H). MS: MS m/z 343 (M$^+$+1).

Preparation of (1R,2S)-1-amino-N-((1-methylcyclopropyl)sulfonyl)-2-vinylcyclopropanecarboxamide hydrochloride

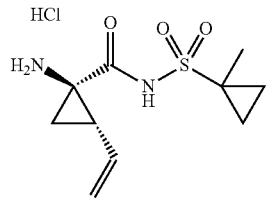 [SMILES: Cl ; C=C[C@@H]1C[C@]1(N)C(=O)NS(=O)(=O)C1(C)CC1]

A solution of tert-butyl ((1R,2S)-1-(((1-methylcyclopropyl)sulfonyl)carbamoyl)-2-vinylcyclopropyl)carbamate (40 g, 116 mmol) in 4 N HCl in dioxane (400 mL) was stirred at room temperature for 1 h. The solvent was evaporated under reduced pressure and the residue was washed with diethyl ether to get crude compound (31 g, 95%). The crude compound was used without further purification. $^1$H NMR (400 MHz, DMSO-d$_6$) δ ppm 8.97-9.29 (m, 2H), 5.47-5.66 (m, 1H), 5.32-5.44 (m, 1H), 5.22 (dd, J=10.04, 1.51 Hz, 1H), 2.38 (s, 1H), 2.03 (s, 1H), 1.71 (d, J=3.51 Hz, 1H), 1.46-1.52 (m, 4H), 1.25-1.35 (m, 1H), 0.88-1.01 (m, 2H). MS: MS m/z 245.14 (M$^+$+1).

Preparation of 1-Fluoro-4-methoxyisoquinoline

Synthesis of 1-fluoro-4-methoxyisoquinoline

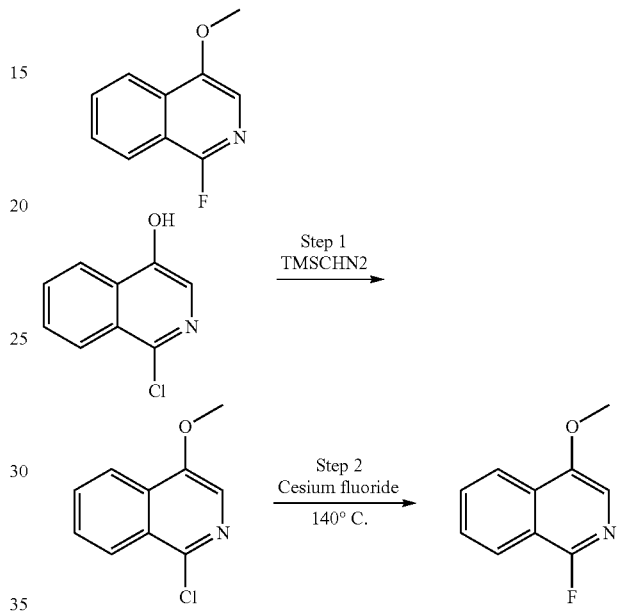

Step 1: Preparation of 1-chloro-4-methoxyisoquinoline

To a solution of 1-chloroisoquinolin-4-ol (5.0 g, 27.8 mmol) in acetonitrile (50 mL) was added TMS-diazomethane (12.73 g, 111.2 mmol) at 0° C. The reaction mixture was allowed to come to room temperature and stirred for 2 h. Solvent was evaporated under reduced pressure to get crude compound. The crude compound was purified by silica gel chromatography to get 1-chloro-4-methoxyisoquinoline (2.5 g, 46.4%) as off-white solid. $^1$H NMR (400 MHz, CD$_3$OD): δ ppm 8.29-8.17 (m, 2H), 7.97 (s, 1H), 7.91-7.82 (m, 2H), 4.05 (s, 3H); MS: MS m/z 194.7 (M$^+$+1).

Step 2: Preparation of 1-Fluoro-4-methoxyisoquinoline

To a solution of 1-chloro-4-methoxyisoquinolin (2.5 g, 12.91 mmol) in DMSO was added cesium fluoride (4.01 g, 25.82 mmol) at room temperature. The reaction vessel (Pressure tube) was sealed and heated at 145° C. for 18 h. The reaction mass was diluted with water and extracted with ethyl acetate. The organic layer was dried over anhydrous Na$_2$SO$_4$ and evaporated under reduced pressure to get crude compound. The crude compound was purified by silica gel chromatography to get desired compound (700 mg, 62%) as a white solid. $^1$H NMR (400 MHz, CD$_3$OD): δ ppm 8.10 (m, 1H), 8.08 (m, 1H), 7.78-7.75 (m, 1H), 7.69-7.65 (m, 1H), 7.49 (m, 1H), 4.04 (s, 3H); $^{19}$F NMR: δ ppm −78.66 (1F); MS: MS m/z 178.1 (M$^+$+1).

Scheme: Preparation of 1,7-difluoro-4-methoxyisoquinoline
Synthesis of 1,7-difluoro-4-methoxyisoquinoline

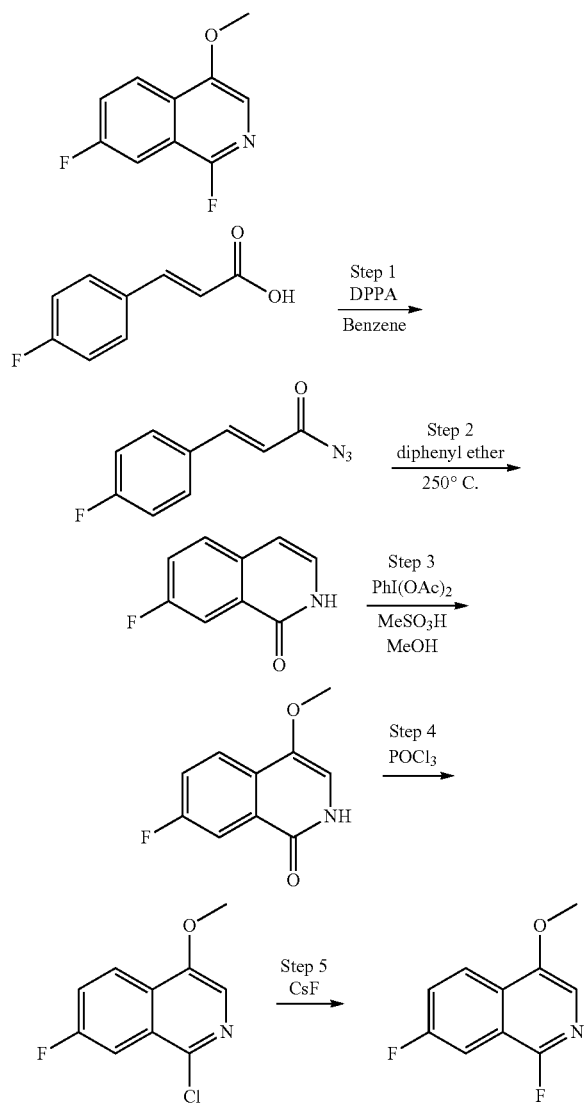

Step 1: Preparation of (E)-3-(4-fluorophenyl) acryloyl azide

To a solution of (E)-3-(4-fluorophenyl) acrylic acid (25 g, 150 mmol) in benzene (120 mL) was added triethylamine (30.5 g, 301 mmol) followed by DPPA (41.4 g, 150 mmol) at room temperature. The reaction mass was stirred at the same temperature for 18 h. The solvent was evaporated under reduced pressure and the residue was diluted with water and extracted with dichloromethane. The organic layer was dried over anhydrous sodium sulfate, filtered and evaporated to get crude compound. The crude compound was purified by conventional column chromatography (Silica gel, 60-120 mesh) using 10% ethyl acetate in pet ether as mobile phase to get the desired compound as a white solid (26 g, 90%). $^1$H NMR (400 MHz, CDCl$_3$): δ ppm 7.73-7.69 (d, J=16 Hz, 1H), 7.55-7.51 (m, 2H), 7.11-7.07 (m, 2H), 6.36-6.32 (d, J=16 Hz, 1H).

Step 2: Preparation of 7-fluoroisoquinolin-1(2H)-one

To a hot (125° C.) diphenyl ether (25 ml) was added (E)-3-(4-fluorophenyl) acryloyl azide (5 g, 26.2 mmol) portion wise. The reaction was heated at 250° C. for 4 h. The reaction mass was cooled to room temperature and diluted with pet ether. The precipitated solid was filtered washed with pet ether to get crude compound (2.45 g, 57%). The crude compound was taken to the next step without further purification. $^1$H NMR (400 MHz, CD$_3$OD): δ ppm 7.96-7.93 (m, 1H), 7.76-7.72 (m, 1H), 7.56-7.51 (m, 1H), 7.18-7.16 (m, 1H), 6.72-6.70 (m, 1H); MS: MS m/z 164.1 (M$^+$+1).

Step 3: Preparation of 7-fluoro-4-methoxyisoquinolin-1(2H)-one

To a solution of 7-fluoroisoquinolin-1(2H)-one (11 g, 67.4 mmol) in methanol was added iodozobenzenediacetate (21.7 g, 67.4 mmol) followed by methane sulphonic acid (7.78 g, 81 mmol) at room temperature. The reaction mass was heated at reflux for 3 h. The solvent was evaporated and the residue was diluted with cold water. The precipitated solid was filtered and washed with water to get crude compound (11 g, 84%) as light red color solid. $^1$H NMR (400 MHz, CD$_3$OD): δ ppm 8.06-8.04 (m, 1H), 7.96-7.93 (m, 1H), 7.62-7.54 (m, 2H), 6.74 (s, 1H), 3.89 (s, 3H); MS: MS m/z 194.1 (M$^+$+1).

Step 4: Preparation of 1-chloro-7-fluoro-4-methoxyisoquinoline

A solution of 7-fluoro-4-methoxyisoquinolin-1(2H)-one (11 g, 56.9 mmol) in POCl$_3$ (100 ml) was refluxed for 18 h. The solvent was evaporated under reduced pressure and the residue was diluted with cold water. The aqueous solution was basified by solid sodium carbonate and extracted with ethyl acetate. The combine organic layer was dried over anhydrous sodium sulfate, filtered and evaporated under reduced pressure to get crude compound. The crude compound was purified by silica gel chromatography (20% ethyl acetate in pet ether) to get desired compound (2.9 g, 24%) as off-white solid. $^1$H NMR (400 MHz, CDCl$_3$): δ ppm 8.36-8.32 (m, 1H), 7.93-7.90 (m, 1H), 7.88 (s, 1H), 7.70-7.65 (m, 1H), 4.11 (s, 3H); MS: MS m/z 212.1 (M$^+$+1).

Step 5: Preparation of 1,7-difluoro-4-methoxyisoquinoline

To a solution of 1-chloro-7-fluoro-4-methoxyisoquinoline (3.7 g, 17.48 mmol) in DMSO was added cesium fluoride (10.26 g, 69.9 mmol) at room temperature. The reaction vessel (Pressure tube) was sealed and heated at 145° C. for 18 h. The reaction mass was diluted with water and extracted with ethyl acetate. The combined organic layer was dried over anhydrous Na$_2$SO$_4$ and evaporated under reduced pressure to get crude compound. The crude compound was purified by silica gel chromatography to get desired compound (1.7 g, 49%) as white solid. $^1$H NMR (400 MHz, CD$_3$OD): δ ppm 8.20-8.18 (m, 1H), 7.69-7.66 (m, 1H), 7.54-7.47 (m, 1H), 7.46 (s, 1H), 4.04 (s, 3H); $^{19}$F NMR: δ ppm 109.65 (1F), −78.53 (1F); MS: MS m/z 196.1 (M$^+$+1).

Scheme: Preparation of 1,7-difluoro-6-methoxyisoquinoline
Synthesis of 1,7-difluoro-6-methoxyisoquinoline:

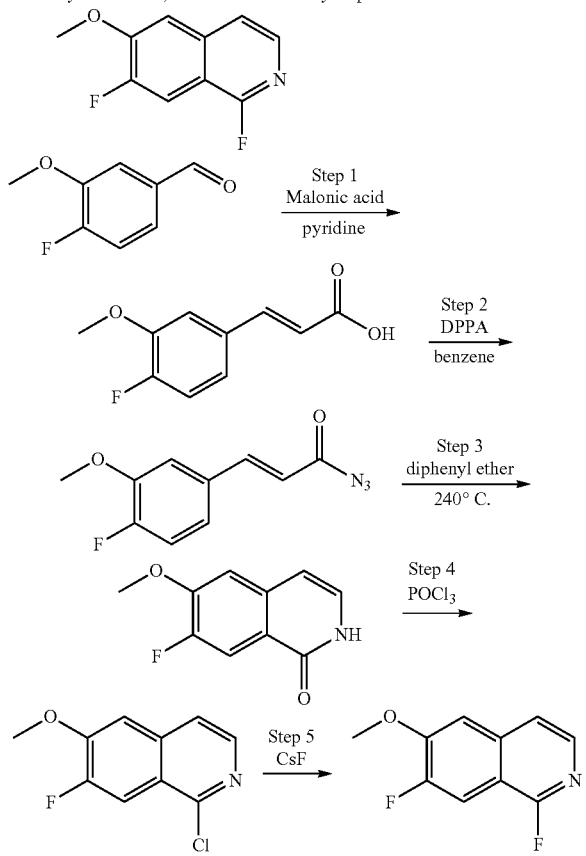

Step 1: Preparation of (E)-3-(4-fluoro-3-methoxyphenyl) acrylic acid

To a solution of 4-fluoro-3-methoxybenzaldehyde (30 g, 195 mmol) in pyridine (134 ml) and piperidine (4.12 ml) was added malonic acid (30.4 g, 292 mmol) at room temperature. The reaction mass was refluxed for 18 h. The solvent was evaporated under reduced pressure and the residue was acidified with 1.5N HCl solution. The precipitated solid was filtered washed with pet ether to get crude compound (37 g, 97%) as white solid. The crude compound was taken to the next step without further purification. $^1$H NMR (400 MHz, CDCl$_3$): δ ppm 12.37 (s, 1H), 7.59-7.55 (d, J=16 Hz, 1H), 7.53 (s, 1H), 7.26-7.22 (m, 2H), 6.59-6.55 (d, J=16 Hz, 1H), 3.89 (s, 3H); MS: MS m/z 195.0 (M$^+$−1).

Step 2: Preparation of (E)-3-(4-fluoro-3-methoxyphenyl) acryloyl azide

To a solution of (E)-3-(4-fluoro-3-methoxyphenyl) acrylic acid (5 g, 25.5 mmol) in benzene (30 ml) was added triethylamine (5.16 g, 51 mmol) followed by DPPA (7.01 g, 25.5 mmol) at room temperature. The reaction mass was stirred at the same temperature for 18 h. The solvent was evaporated under reduced pressure and the residue was diluted with water and extracted with dichloromethane. The organic layer was dried over anhydrous sodium sulfate, filtered and evaporated to get crude compound. The crude compound was purified by conventional column chromatography (Silica gel, 60-120 mesh) using 10% ethyl acetate in pet ether as mobile phase to get the desire compound as white solid (4 g, 71%). $^1$H NMR (400 MHz, CDCl$_3$): δ ppm 7.70-7.66 (d, J=16 Hz, 1H), 7.12-7.07 (m, 3H), 6.35-6.31 (d, J=16 Hz, 1H), 3.92 (s, 3H).

Step 3: Preparation of 7-fluoro-6-methoxyisoquinolin-1(2H)-one

To a hot (125° C.) diphenyl ether (20 ml) was added (E)-3-(4-fluoro-3-methoxyphenyl) acryloyl azide (4 g, 18.08 mmol) portionwise. The reaction was heated at 250° C. for 4 h. The reaction mass was cooled to room temperature and diluted with pet ether. The precipitated solid was filtered washed with pet ether to get crude compound (3.1 g, 89%). The crude compound was taken to the next step without further purification. MS: MS m/z 194.1 (M$^+$+1).

Step 4: Preparation of 1-chloro-7-fluoro-6-methoxyisoquinoline

A solution of 7-fluoro-6-methoxyisoquinolin-1(2H)-one (3.1 g, 16.05 mmol) in POCl$_3$ (25 ml) was refluxed for 18 h. The solvent was evaporated under reduced pressure and the residue was diluted with cold water. The aqueous solution was basified by solid sodium carbonate and extracted with ethyl acetate. The organic layer was dried over anhydrous sodium sulfate, filtered and evaporated under reduced pressure to get crude compound. The crude compound was purified by silica gel chromatography (20% ethyl acetate in pet ether) to get desired compound (1.9 g, 55%) as off-white solid. $^1$H NMR (400 MHz, CDCl$_3$): δ ppm 8.22-8.20 (d, J=8 Hz, 1H), 7.97-7.94 (m, 1H), 7.49-7.48 (m, 1H), 7.18-7.16 (d, J=8 Hz, 1H), 4.04 (s, 3H); MS: MS m/z 211.7 (M$^+$+1).

Step 5: Preparation of 1,7-difluoro-6-methoxyisoquinoline

To a solution of 1-chloro-7-fluoro-6-methoxyisoquinoline (1.5 g, 7.09 mmol) in DMSO was added cesium fluoride (2.15 g, 14.18 mmol) at room temperature. The reaction vessel (Pressure tube) was sealed and heated at 145° C. for 18 h. The reaction mass was diluted with water and extracted with ethyl acetate. The combined organic layer was dried over anhydrous Na$_2$SO$_4$ and evaporated under reduced pressure to get crude compound. The crude compound was purified by silica gel chromatography to get desired compound (950 mg, 68%) as white solid. $^1$H NMR (400 MHz, CDCl$_3$): δ ppm 8.0-7.98 (m, 1H), 7.77-7.74 (d, J=12 Hz, 1H), 7.42-7.40 (m, 1H), 7.21-7.19 (m, 1H), 4.04 (s, 3H); $^{19}$F NMR: δ ppm −129.05 (1F), −71.98 (1F); MS: MS m/z 196.1 (M$^+$+1).

Scheme: Preparation of 2-chloro-6-methoxy-3-(trifluoromethyl)quinoxaline and 3-chloro-6-methoxy-2-(trifluoromethyl)quinoxaline
Synthesis of 2-chloro-6-methoxy-3-(trifluoromethyl)quinoxaline & 3-chloro-6-methoxy-2-(trifluoromethyl)quinoxaline

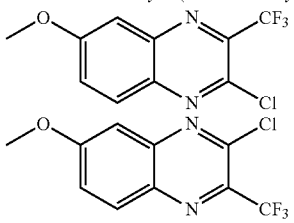

-continued

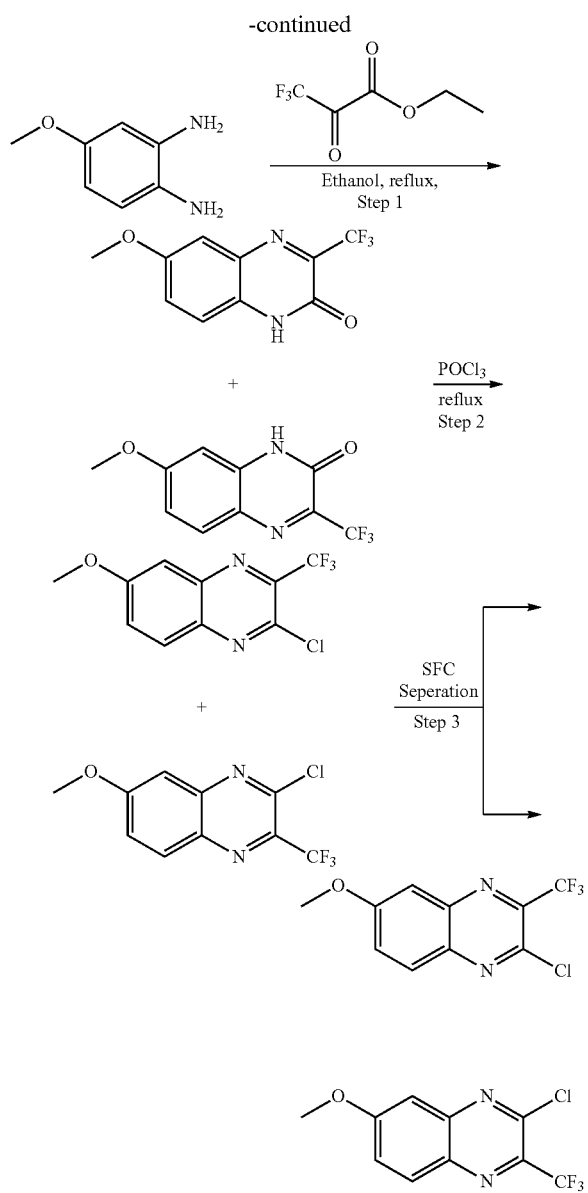

Step 1: Preparation of 6-methoxy-3-(trifluoromethyl)quinoxalin-2(1H)-one and 7-methoxy-3-(trifluoromethyl)quinoxalin-2(1H)-one To a solution of 4-methoxybenzene-1,2-diamine (1 g, 7.24 mmol) in ethanol (10 ml) was added ethyl 3,3,3-trifluoro-2-oxopropanoate (1.23 g, 7.24 mmol)). The reaction mass was heated at reflux for overnight. The solvent was evaporated under reduced pressure and the residue was diluted with ethyl acetate and then evaporated to dryness to get the crude compound. The crude compound was washed with pet ether to get the product (1.55 g, 88% yield) as a mixture of regioisomer (black solid). This crude compound was taken to the next step without separation of isomers. $^1$H NMR (400 MHz, DMSO-d$_6$): δ ppm 12.92 (br, s, 2H), 7.84-7.81 (d, J=12 Hz, 1H), 7.44-7.33 (m, 4H), 7.82 (s, 1H), 3.87 (s, 6H), MS: MS m/z 245.15 (M$^+$+1).

Steps 2 and 3: Preparation of 2-chloro-6-methoxy-3-(trifluoromethyl)quinoxaline and 3-chloro-6-methoxy-2-(trifluoromethyl)quinoxaline A solution of 6-methoxy-3-(trifluoromethyl)quinoxalin-2(1H)-one & 7-methoxy-3-(trifluoromethyl)quinoxalin-2(1H)-one (0.90 g, 3.69 mmol) in POCl$_3$ (10 ml) was refluxed for 3 h. The solvent was evaporated under reduced pressure and the residue was diluted with cold water. The aqueous solution was basified by solid sodium carbonate and extracted with ethyl acetate. The combine organic layer was dried over anhydrous sodium sulfate, filtered and evaporated under reduced pressure to get crude compound. The crude compound was purified by silica gel chromatography (20% ethyl acetate in pet ether) to get mixture of regioisomer. The mixture of regioisomer were separated by SFC purification to afford 2-chloro-6-methoxy-3-methylquinoxaline (required isomer) (0.31 g, 32%) and 3-chloro-6-methoxy-2-methylquinoxaline (0.15 g, 15.5%) as off white solids.
2-chloro-6-methoxy-3-(trifluoromethyl)quinoxaline: $^1$H NMR (400 MHz, DMSO-d$_6$): δ ppm 8.10-8.07 (d, J=12 Hz, 1H), 7.75-7.44 (m, 2H), 3.95 (s, 3H); $^{19}$F NMR: δ ppm −65.36 (1F) MS: MS m/z 263.10 (M$^+$+1).
3-chloro-6-methoxy-2-(trifluoromethyl)quinoxaline: $^1$H NMR (400 MHz, DMSO-d6): δ ppm 8.11-8.08 (d, J=12 Hz, 1H), 7.78-7.75 (d, J=12 Hz, 1H), 7.68 (s, 1H), 4.00 (s, 3H); $^{19}$F NMR: δ ppm −65.36 (1F) MS: MS m/z 263.09 (M$^+$+1).

Scheme: Preparation of Synthesis of 2-chloro-3-isopropyl-6-methoxyquinoxaline & 3-chloro-2-isopropyl-6-methoxyquinoxaline
Synthesis of 2-chloro-3-isopropyl-6-methoxyquinoxaline & 3-chloro-2-isopropyl-6-methoxyquinoxaline

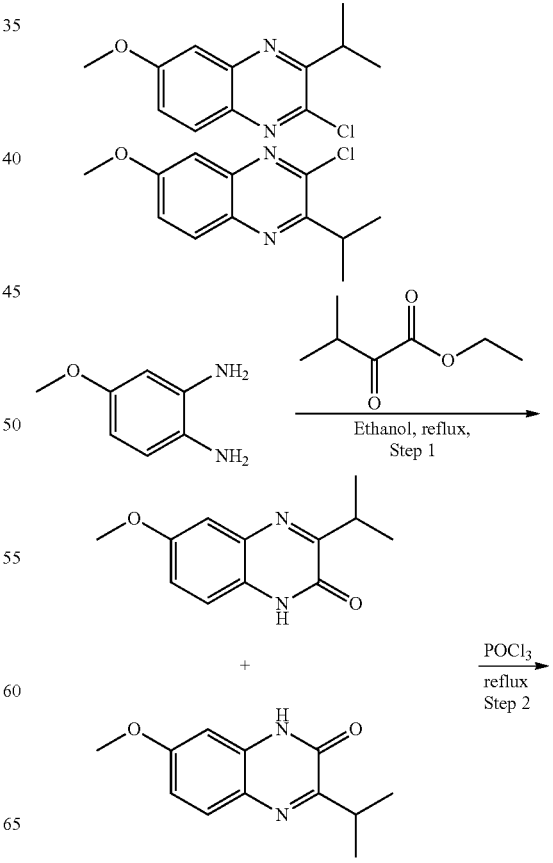

-continued

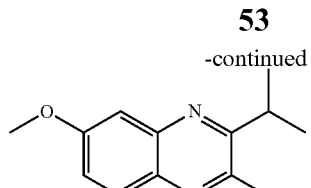

+

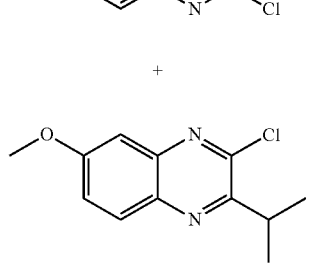

SFC Seperation →

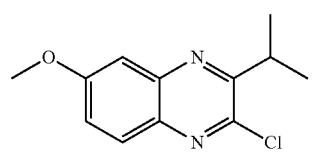

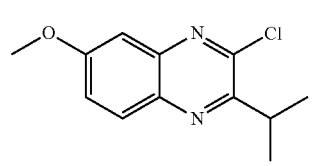

Step 1: Preparation of 3-isopropyl-6-methoxyquinoxalin-2(1H)-one and 3-isopropyl-7-methoxyquinoxalin-2(1H)-one The same procedure was followed as described for 6-methoxy-3-(trifluoromethyl)quinoxalin-2(1H)-one but ethyl 3-methyl-2-oxobutanoate was used as starting material instead of ethyl 3,3,3-trifluoro-2-oxopropanoate. MS: MS m/z 219.1 (M$^+$+1).

Step 2: Preparation of 2-chloro-3-isopropyl-6-methoxyquinoxaline and 3-chloro-2-isopropyl-6-methoxyquinoxaline The same procedure was followed as described for 2-chloro-6-methoxy-3-(trifluoromethyl)quinoxaline but 3-isopropyl-6-methoxyquinoxalin-2(1H)-one and 3-isopropyl-7-methoxyquinoxalin-2(1H)-one was used as starting material instead of 6-methoxy-3-(trifluoromethyl)quinoxalin-2(1H)-one and 7-methoxy-3-(trifluoromethyl)quinoxalin-2(1H)-one.

3-chloro-2-isopropyl-6-methoxyquinoxaline: $^1$H NMR (400 MHz, CDCl$_3$): δ ppm $^1$H NMR (400 MHz, CDCl$_3$): 7.94 (d, J=9.2 Hz, 1H) 7.38-7.35 (dd, J=9.2 Hz, 2.8 Hz, 1H) 7.27-7.26 (m, 1H) 3.91 (s, 3H) 3.70-3.63 (m, 1H) 1.40 (d, J=8 Hz, 6H). MS: MS m/z 237.05 (M$^+$+1).

2-chloro-3-isopropyl-6-methoxyquinoxaline: MS: MS m/z 237.06 (M$^+$+1).

Preparation of pyridin-2-yl (1,1,1-trifluoro-2-methylpropan-2-yl) carbonate

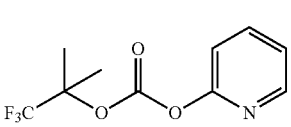

To a solution of 1,1,1-trifluoro-2-methylpropan-2-ol (10 g, 78 mmol) in DIPEA (40.9 ml, 234 mmol) was added DMAP (9.54 g, 78 mmol) and the solution was stirred 10 min at room temperature. To the solution was added dipyridin-2-yl carbonate (16.8 g, 78 mmol). The solution was stirred overnight. The reaction mass was filtered, washing with DIPEA (2*10 mL); the filtrate was concentrated under vacuum and then diluted with DCM (300 mL). The solution was washed with aq. 1.5N HCl solution (2×150 mL), followed by brine solution (100 mL). The organic phase was dried over Na2SO4, filtered and concentrated under reduced pressure to afford crude product as red color liquid. The crude compound was purified by silica gel chromatography eluting with EtOAc in pet-ether [0-5% over 25 min] as gradient, using 40 g silica column, collected the product fractions and concentrated to afford pyridin-2-yl (1,1,1-trifluoro-2-methylpropan-2-yl) carbonate (9.0 g, 36 mmol, 46% yield) as colorless liquid. $^1$H NMR (400 MHz, CDCl$_3$) δ ppm 8.41-8.40 (d, J=4.8 Hz, 1H), 7.84-7.79 (m, 1H), 7.28-7.24 (m, 1H), 7.13-7.10 (d, J=10 Hz, 1H), 1.78 (s, 6H). MS: MS m/z 250.54 (M$^+$+1).

Preparation of Compound 1010 and Compound 1011

Compound 1010

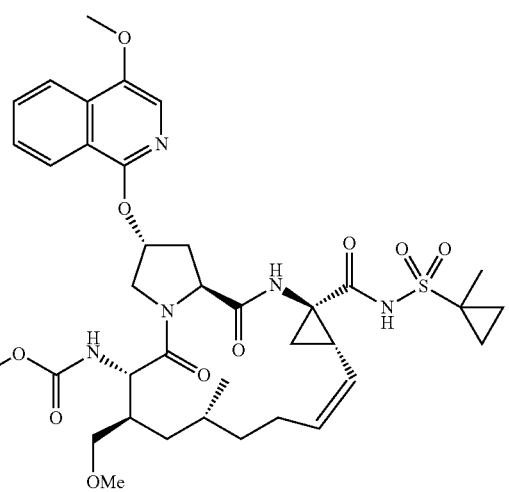

Compound 1011

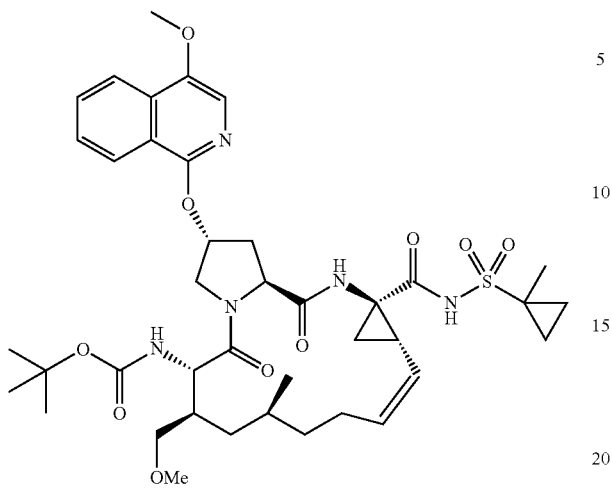

To a solution of tert-butyl ((2R,6S,7R,9R,13aS,14aR, 16aS,Z)-2-hydroxy-7-(methoxymethyl)-9-methyl-14a-(((1-methylcyclopropyl)sulfonyl)carbamoyl)-5,16-dioxo-1,2,3, 5,6,7,8,9,10,11,13a,14,14a,15,16,16a-hexadecahydrocyclopropa[e]pyrrolo[1,2-a][1,4]diazacyclopentadecin-6-yl)carbamate (50 mg, 0.078 mmole) and 1-fluoro-4-methoxyisoquinoline (13.8 mg, 0.078 mmole) in DMSO (5 mL) was added t-BuOK (0.234 mL, 0.234 mmol, 1M solution in THF) at room temperature under nitrogen atmosphere. The reaction mixture was stirred at room temperature for 2 h. The reaction mass was quenched with aqueous citric acid solution and extracted with ethyl acetate (50 mL×3). The combined organic layer was washed with water, brine solution, dried over anhydrous $Na_2SO_4$ and evaporated under reduced pressure to get crude compound tert-butyl ((2R,6S,7R,13aS,14aR,16aS,Z)-2-((4-methoxyisoquinolin-1-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate as diastereomer mixture. The crude compound was purified by prep-HPLC to get 25 mg (40%) of compound 1010 and 12 mg (19%) of compound 1011 as white solid.

Compound 1010: tert-butyl ((2R,6S,7R,9R,13aS,14aR, 16aS,Z)-2-((4-methoxyisoquinolin-1-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, $CD_3OD$): δ ppm 8.15 (m, 2H) 7.72 (t, J=7.40 Hz, 1H) 7.55 (m, 2H) 6.60 (d, J=8.03 Hz, 1H) 5.84 (br. s., 1H) 5.62 (td, J=10.23, 5.65 Hz, 1H) 5.00 (t, J=10.04 Hz, 1H) 4.79 (d, J=11.29 Hz, 1H) 4.63 (dd, J=9.91, 7.15 Hz, 1H) 4.26 (dd, J=10.54, 8.03 Hz, 1H) 4.03 (m, 4H) 3.47 (m, 2H) 2.73 (m, 2H) 2.42 (m, 2H) 1.92 (m, 2H) 1.76 (dd, J=8.28, 5.77 Hz, 1H) 1.65 (m, 1H) 1.55 (m, 5H) 1.44 (m, 3H) 1.28 (m, 4H) 1.11 (m, 9H) 1.00 (m, 4H) 0.90 (m, 2H). MS: MS m/z 796.2 ($M^+$−1).

Compound 1011: tert-butyl ((2R,6S,7R,9S,13aS,14aR,16aS, Z)-2-((4-methoxyisoquinolin-1-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16, 16a-hexadecahydrocyclopropa[e]pyrrolo[1,2-a][1,4]diazacyclopentadecin-6-yl)carbamate. MS: MS m/z 796.2 ($M^+$−1).

Preparation of (2R,6S,7R,13aS,14aR,16aS,Z)-6-amino-2-((4-methoxyisoquinolin-1-yl)oxy)-7-(methoxymethyl)-9-methyl-N-((1-methylcyclopropyl)sulfonyl)-5,16-dioxo-1,2,3,5,6,7,8,9,10,11,13a, 14,14a,15,16,16a-hexadecahydrocyclopropa[e]pyrrolo[1,2-a][1,4]diazacyclopentadecine-14a-carboxamide hydrochloride

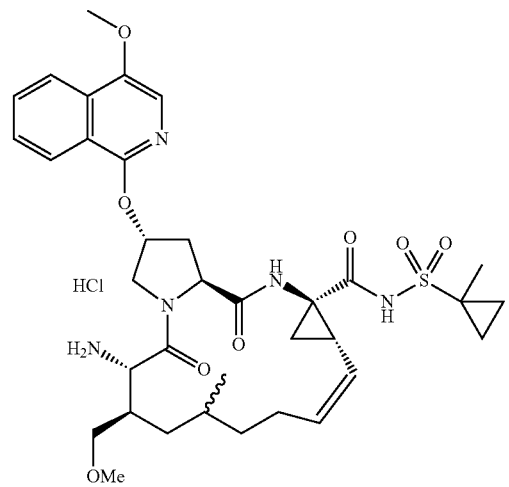 [SMILES: COC[C@@H]1CC(C)CC/C=C\[C@@H]2C[C@@]2(C(=O)NS(=O)(=O)C2(C)CC2)NC(=O)[C@@H]2C[C@@H](Oc3ncc(OC)c4ccccc34)CN2C(=O)[C@H]1N ; Cl]

A solution of tert-butyl ((2R,6S,7R,13aS,14aR,16aS,Z)-2-((4-methoxyisoquinolin-1-yl)oxy)-7-(methoxymethyl)-9-methyl-14a-(((1-methylcyclopropyl)sulfonyl)carbamoyl)-5, 16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate (95 mg, 0.119 mmol) in dioxane. HCl (10 mL) was stirred at room temperature for 30 min. The solvent was evaporated under reduced pressure to get crude compound (90 mg, 93%). The crude compound was washed with diethyl ether and taken to the next step without further purification. MS: MS m/z 698.5 ($M^+$+1).

Preparation of Compound 1016 and Compound 1017

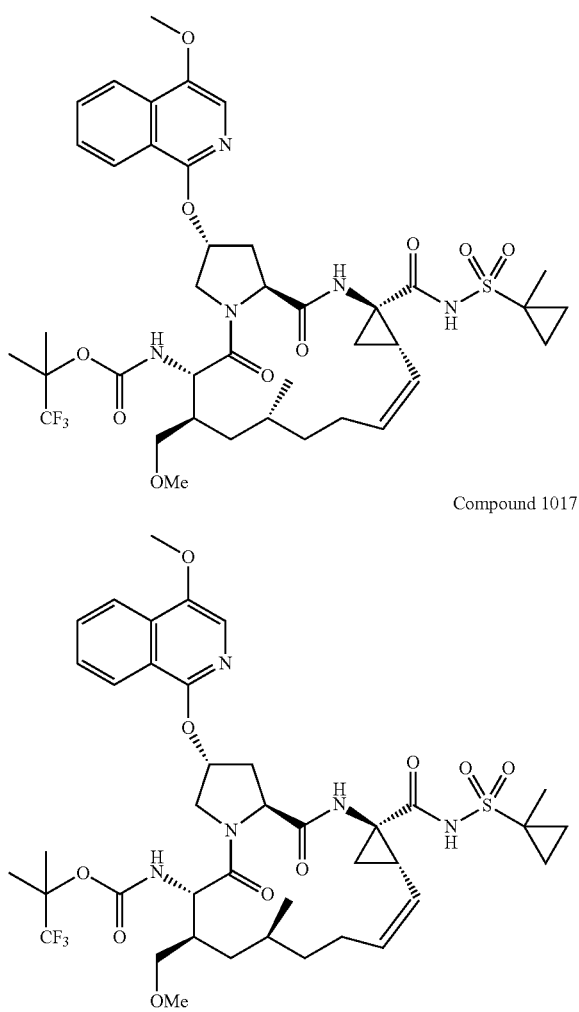

Compound 1016

Compound 1017

A solution of (2R,6S,7R,13aS,14aR,16aS,Z)-6-amino-2-((4-methoxyisoquinolin-1-yl)oxy)-7-(methoxymethyl)-9-methyl-N-((1-methylcyclopropyl)sulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide hydrochloride (90 mg, 0.110 mmol) in DCM (4 mL) was added DIPEA (0.068 mL, 0.387 mmole) followed by pyridin-2-yl (1,1,1-trifluoro-2-methylpropan-2-yl) carbonate (38 mg, 0.155 mmole). The reaction mixture was stirred at room temperature for 30 min. The reaction mass was diluted with DCM and washed with water. The organic layer was dried over anhydrous $Na_2SO_4$ and evaporated under reduced pressure to get crude compound as diastereomer mixture. The crude compound was purified by prep-HPLC to get compound 1008 (14 mg, 12%) and Compound 1009 (19 mg, 17%) as white solids.

Compound 1016: 1,1,1-trifluoro-2-methylpropan-2-yl ((2R,6S,7R,9R,13aS,14aR,16aS,Z)-2-((4-methoxyisoquinolin-1-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate.

$^1$H NMR (400 MHz, $CD_3OD$): δ ppm 8.15 (m, 2H) 7.74 (td, J=7.72, 1.13 Hz, 1H) 7.56 (m, 2H) 5.83 (br. s., 1H) 5.61 (m, 1H) 5.01 (t, J=9.91 Hz, 1H) 4.78 (s, 1H) 4.67 (dd, J=10.29, 7.28 Hz, 1H) 4.22 (m, 1H) 4.00 (m, 4H) 3.46 (m, 2H) 3.30 (s, 4H) 2.73 (m, 2H) 2.43 (m, 2H) 1.95 (m, 2H) 1.77 (dd, J=8.41, 5.65 Hz, 1H) 1.66 (d, J=10.29 Hz, 1H) 1.55 (m, 6H) 1.44 (m, 2H) 1.28 (m, 5H) 0.96 (m, 8H). $^{19}$F NMR (400 MHz, $CD_3OD$): δ ppm −85.2 (s, 3F). MS: MS m/z 850.2 ($M^+$−1).

Compound 1017: 1,1,1-trifluoro-2-methylpropan-2-yl ((2R,6S,7R,9S,13aS,14aR,16aS,Z)-2-((4-methoxyisoquinolin-1-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate.

$^1$H NMR (400 MHz, $CD_3OD$): δ ppm 8.20 (d, J=8.28 Hz, 1H) 8.12 (d, J=8.28 Hz, 1H) 7.74 (ddd, J=8.34, 7.09, 1.13 Hz, 1H) 7.57 (m, 2H) 5.85 (br. s., 1H) 5.73 (d, J=8.53 Hz, 1H) 5.04 (br. s., 1H) 4.72 (t, J=8.41 Hz, 1H) 4.53 (m, 2H) 4.04 (m, 4H) 3.49 (m, 3H) 3.37 (m, 4H) 2.72 (dd, J=13.43, 7.40 Hz, 1H) 2.59 (br. s., 1H) 2.45 (m, 2H) 2.15 (m, 1H) 1.98 (m, 1H) 1.71 (m, 1H) 1.60 (m, 3H) 1.51 (s, 3H) 1.45 (m, 4H) 1.33 (m, 2H) 1.22 (m, 2H) 0.93 (m, 6H). $^{19}$F NMR (400 MHz, $CD_3OD$): δ ppm −85.13 (s, 3F). MS: MS m/z 850.2 (M'-1).

Preparation of Compound 1001

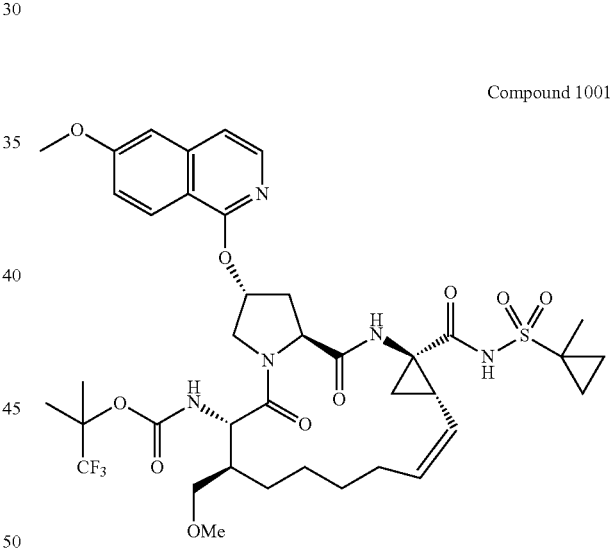

Compound 1001

Compound 1001 was prepared using the intermediates described herein and by following the general procedure described for the synthesis of Compound 1016.

Compound 1001: 1,1,1-trifluoro-2-methylpropan-2-yl ((2R,6S,7R,13aS,14aR,16aS,Z)-2-((6-methoxyisoquinolin-1-yl)oxy)-7-(methoxymethyl)-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, $CD_3OD$): δ ppm 8.11 (d, J=9.04 Hz, 1H) 7.93 (d, J=6.02 Hz, 1H) 7.27 (s, 1H) 7.21 (d, J=2.26 Hz, 1 H) 7.11 (dd, J=9.16, 2.38 Hz, 1H) 5.87 (br. s., 1H) 5.66 (d, J=8.78 Hz, 1H) 4.71 (m, 2H) 4.26 (d, J=10.79 Hz, 1H) 4.02 (dd, J=11.54, 3.26 Hz, 1H) 3.94 (s, 3H) 3.44 (d, J=2.76 Hz, 2H) 2.73 (m, 1H) 2.50 (m, 3H) 1.95 (m, 3H) 1.75 (dd, J=8.16, 5.40 Hz, 1H) 1.58 (m, 7H) 1.37 (m, 10H) 1.02 (s, 3H) 0.88

(m, 3H). $^{19}$F NMR (400 MHz, CD$_3$OD): δ ppm −85.10 (s, 3F). MS: MS m/z 838.2 (M$^+$+1).

Preparation of Compound 1002

Preparation of Compound 1003 and Compound 1004

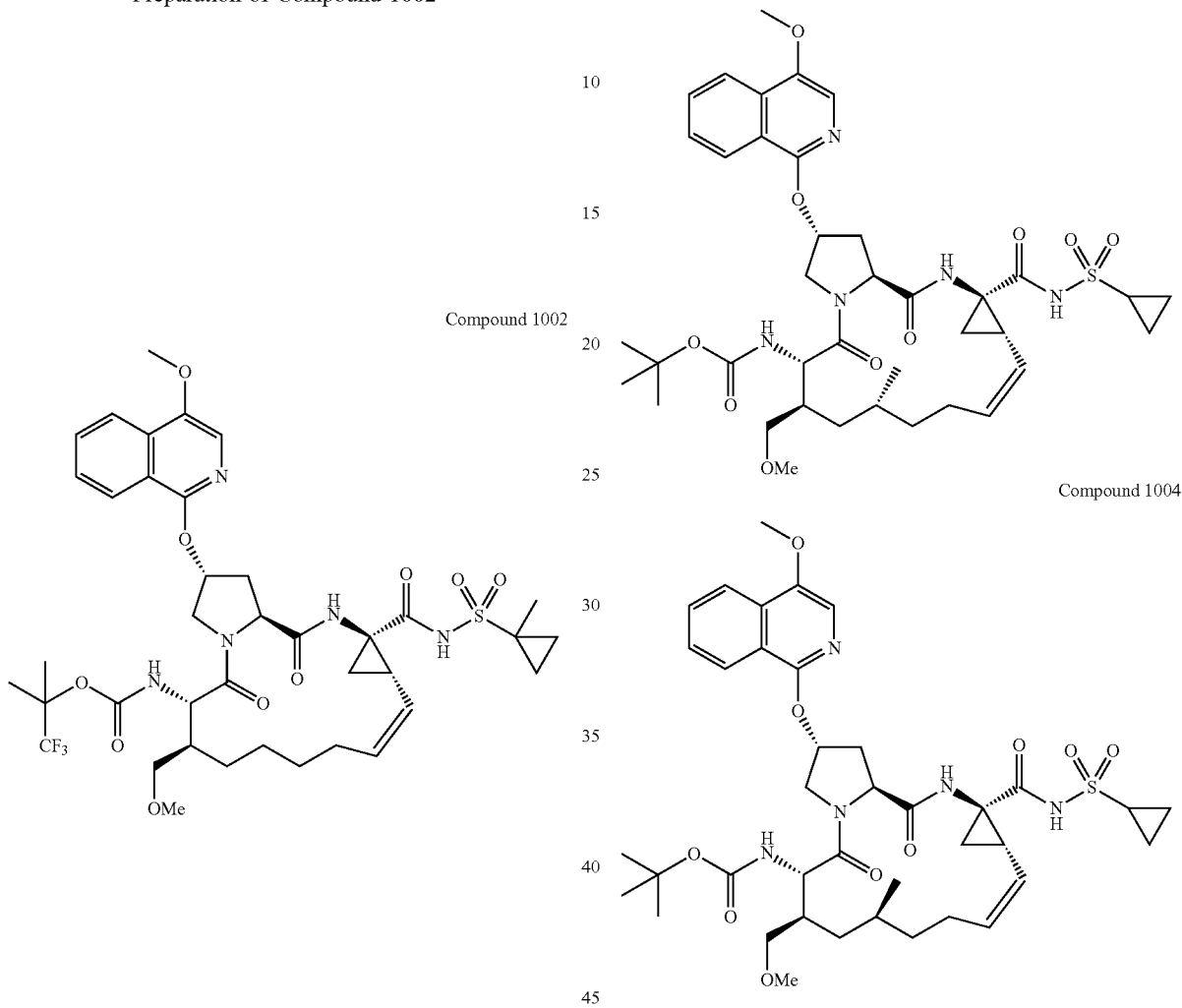

Compound 1002

Compound 1003

Compound 1004

Compound 1002 was prepared using the intermediates described herein and by following the general procedure described for the synthesis of Compound 1016.

Compound 1002: 1,1,1-trifluoro-2-methylpropan-2-yl ((2R,6S,7R,13aS,14aR,16aS,Z)-2-((4-methoxyisoquinolin-1-yl)oxy)-7-(methoxymethyl)-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, CD$_3$OD): δ ppm 8.15 (m, 2H) 7.73 (m, 1H) 7.57 (m, 2H) 5.84 (br. s., 1H) 5.69 (m, 1H) 5.06 (t, J=9.54 Hz, 1H) 4.80 (d, J=11.54 Hz, 1H) 4.70 (dd, J=9.91, 7.15 Hz, 1H) 4.24 (d, J=10.79 Hz, 1H) 4.01 (m, 4H) 3.44 (d, J=2.76 Hz, 2H) 3.29 (s, 3H) 2.75 (dd, J=13.80, 7.03 Hz, 1H) 2.52 (m, 3H) 1.94 (m, 2H) 1.75 (dd, J=8.28, 5.52 Hz, 1H) 1.63 (m, 2H) 1.52 (s, 4H) 1.43 (m, 5H) 1.32 (s, 4H) 0.88 (m, 5H). $^{19}$F NMR (400 MHz, CD$_3$OD): δ ppm −85.21 (s, 3F) MS: MS m/z 838.2 (M$^+$+1).

Compound 1003 and compound 1004 were prepared using the intermediates described herein and by following the general procedure described for the synthesis of Compound 1010.

Compound 1003: tert-butyl ((2R,6S,7R,9R,13aS,14aR,16aS,Z)-14a-((cyclopropylsulfonyl)carbamoyl)-2-((4-methoxyisoquinolin-1-yl)oxy)-7-(methoxymethyl)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, CD$_3$OD): δ ppm 8.15 (m, 2H) 7.72 (t, J=7.53 Hz, 1H) 7.55 (m, 2H) 5.83 (br. s., 1H) 5.62 (td, J=10.16, 5.52 Hz, 1H) 4.78 (d, J=11.54 Hz, 1H) 4.61 (m, 1H) 4.25 (d, J=10.79 Hz, 1H) 4.00 (m, 4H) 3.45 (m, 2H) 3.30 (s, 3H) 2.92 (m, 1H) 2.73 (m, 2H) 2.42 (m, 2H) 1.94 (m, 2H) 1.78 (m, 3H) 1.53 (m, 6H) 1.28 (m, 11H) 1.07 (m, 4H). MS: MS m/z 784.2 (M$^+$+1).

Compound 1004: tert-butyl ((2R,6S,7R,9S,13aS,14aR,16aS,Z)-14a-((cyclopropylsulfonyl)carbamoyl)-2-((4-methoxyisoquinolin-1-yl)oxy)-7-(methoxymethyl)-9-methyl-5,16-dioxo-1,2,3,5,6,7,8,9,10,11,13a,14,14a,15,16,16a-hexadecahydrocyclopropa[e]pyrrolo[1,2-a][1,4]

diazacyclopentadecin-6-yl)carbamate. $^1$H NMR (400 MHz, CD$_3$OD): δ ppm 8.15 (m, 2H) 7.73 (t, J=7.65 Hz, 1H) 7.58 (m, 2H) 5.85 (br. s., 1H) 5.71 (d, J=8.53 Hz, 1H) 4.66 (m, 2H) 4.46 (d, J=11.29 Hz, 1H) 4.07 (m, 4H) 3.47 (m, 5H) 2.89 (br. s., 1H) 2.71 (dd, J=13.55, 7.53 Hz, 1H) 2.45 (m, 3H) 2.05 (m, 3H) 1.74 (dd, J=7.78, 5.52 Hz, 1H) 1.62 (dd, J=9.41, 5.40 Hz, 1H) 1.51 (d, J=12.80 Hz, 3H) 1.28 (m, 11H) 1.04 (m, 8H). MS: MS m/z 784.2 (M$^+$+1).

Preparation of Compound 1005 and Compound 1006

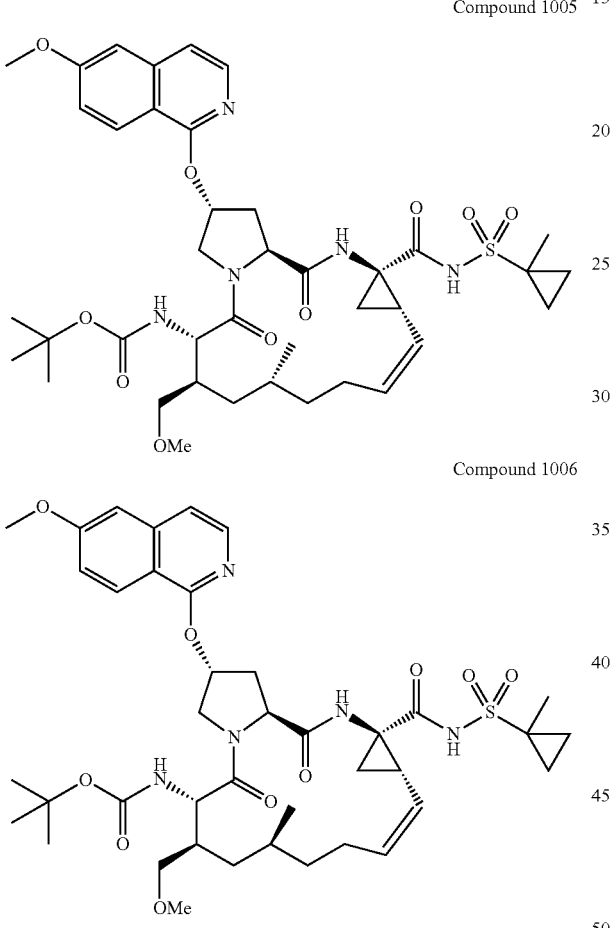

Compound 1005

Compound 1006

Compound 1005 and compound 1006 were prepared using the intermediates described herein and by following the general procedure described for the synthesis of Compound 1010.

Compound 1005: tert-butyl ((2R,6S,7R,9R,13aS,14aR,16aS,Z)-2-((6-methoxyisoquinolin-1-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, CD$_3$OD): δ ppm 8.13 (d, J=9.03 Hz, 2H) 7.92 (d, J=5.77 Hz, 1H) 7.25 (d, J=5.77 Hz, 1H) 7.19 (d, J=2.26 Hz, 1H) 7.09 (dd, J=9.16, 2.13 Hz, 1H) 5.88 (br. s., 1H) 5.61 (td, J=10.16, 5.77 Hz, 1H) 4.77 (d, J=11.80 Hz, 1H) 4.61 (m, 1H) 4.26 (m, 1H) 4.03 (dd, J=11.42, 3.14 Hz, 1H) 3.94 (s, 3H) 3.48 (m, 2H) 3.30 (s, 3H) 2.74 (m, 2H) 2.43 (m, 2H) 1.93 (m, 2H) 1.76 (dd, J=8.28, 5.77 Hz, 1H) 1.57 (m, 7H) 1.42 (m, 1H) 1.28 (m, 2H) 1.17 (s, 8H) 1.03 (m, 4H) 0.88 (br. s., 2H). MS: MS m/z 798.2 (M$^+$+1).

Compound 1006: tert-butyl ((2R,6S,7R,9S,13aS,14aR,16aS,Z)-2-((6-methoxyisoquinolin-1-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, CD$_3$OD): δ ppm 8.14 (d, J=9.04 Hz, 1H) 7.92 (d, J=5.77 Hz, 1H) 7.27 (d, J=5.77 Hz, 1H) 7.20 (d, J=1.76 Hz, 1H) 7.11 (d, J=9.29 Hz, 1H) 5.90 (br. s., 1H) 5.73 (br. s., 1H) 4.65 (m, 2H) 4.45 (d, J=10.54 Hz, 1H) 4.10 (m, 1H) 3.94 (s, 3H) 3.50 (d, J=1.51 Hz, 2H) 3.40 (br. s., 3H) 2.71 (dd, J=14.05, 7.28 Hz, 1H) 2.44 (d, J=8.78 Hz, 2H) 2.13 (br. s., 1H) 1.97 (m, 1H) 1.71 (m, 1H) 1.51 (m, 9H) 1.29 (br. s., 8H) 1.15 (m, 3H) 0.92 (m, 5H). MS: MS m/z 798.2 (M$^+$+1).

Preparation of Compound 1007

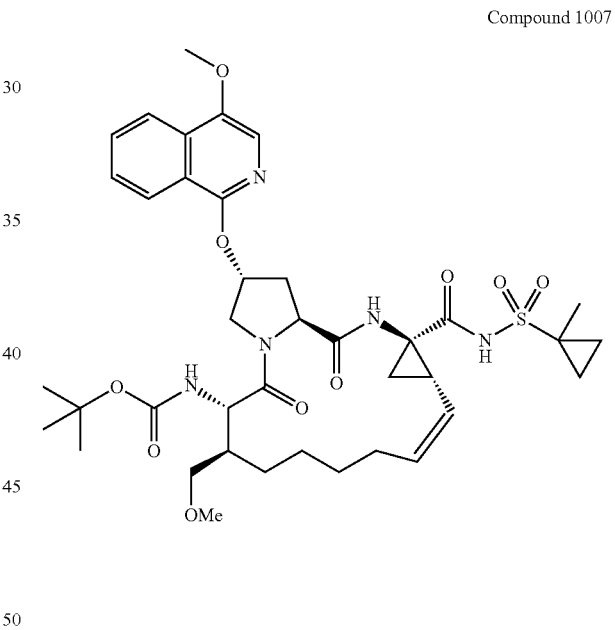

Compound 1007

Compound 1007 was prepared using the intermediates described herein and by following the general procedure described for the synthesis of Compound 1010.

Compound 1007: tert-butyl ((2R,6S,7R,13aS,14aR,16aS,Z)-2-((4-methoxyisoquinolin-1-yl)oxy)-7-(methoxymethyl)-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, CD$_3$OD): δ ppm 8.15 (m, 2H) 7.73 (t, J=7.15 Hz, 1H) 7.56 (m, 2H) 5.85 (br. s., 1H) 5.71 (m, 1H) 5.06 (m, 1H) 4.79 (m, 2H) 4.67 (dd, J=9.79, 7.28 Hz, 1H) 4.29 (d, J=10.79 Hz, 1H) 4.05 (m, 4H) 3.44 (m, 4H) 3.29 (m, 3H) 2.74 (dd, J=13.43, 7.15 Hz, 1H) 2.54 (m, 3H) 1.75 (dd, J=8.28, 5.52 Hz, 1H) 1.62 (m, 2H) 1.52 (s, 4H) 1.40 (m, 9H) 1.12 (s, 8H) 0.91 (m, 3H). MS: MS m/z 784.2 (M$^+$+1).

Preparation of Compound 1008 and Compound 1009

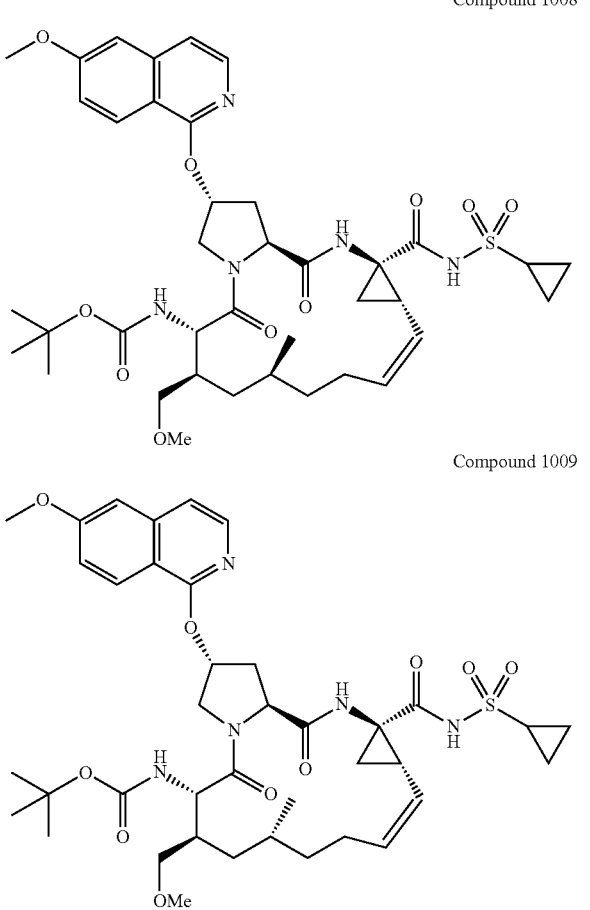

Compound 1008

Compound 1009

Compound 1008 and compound 1009 were prepared using the intermediates described herein and by following the general procedure described for the synthesis of Compound 1010.

Compound 1008: tert-butyl ((2R,6S,7R,9S,13aS,14aR,16aS,Z)-14a-((cyclopropylsulfonyl)carbamoyl)-2-((6-methoxyisoquinolin-1-yl)oxy)-7-(methoxymethyl)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, CD$_3$OD): δ ppm 8.14 (d, J=9.03 Hz, 1H) 7.91 (d, J=5.77 Hz, 1H) 7.26 (d, J=6.02 Hz, 1H) 7.20 (d, J=2.01 Hz, 1H) 7.11 (d, J=8.78 Hz, 1H) 5.88 (br. s., 1H) 5.68 (d, J=7.78 Hz, 1H) 4.66 (d, J=4.77 Hz, 2H) 4.43 (d, J=11.04 Hz, 1H) 4.11 (m, 1H) 3.94 (s, 3H) 3.51 (m, 2H) 3.43 (s, 3H) 2.83 (br. s., 1H) 2.70 (dd, J=13.18, 7.40 Hz, 1H) 2.49 (d, J=13.55 Hz, 2H) 2.30 (br. s., 1H) 2.02 (m, 4H) 1.76 (dd, J=8.03, 5.27 Hz, 1H) 1.63 (dd, J=9.54, 5.02 Hz, 1H) 1.50 (m, 3H) 1.28 (m, 9H) 1.06 (m, 10H). MS: MS m/z 784.2 (M$^+$+1).

Compound 1009: tert-butyl ((2R,6S,7R,9R,13aS,14aR,16aS,Z)-14a-((cyclopropylsulfonyl)carbamoyl)-2-((6-methoxyisoquinolin-1-yl)oxy)-7-(methoxymethyl)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, CD$_3$OD): δ ppm 8.13 (d, J=9.29 Hz, 2H) 7.91 (d, J=6.02 Hz, 1H) 7.25 (d, J=6.02 Hz, 1H) 7.19 (d, J=2.26 Hz, 1H) 7.09 (dd, J=9.16, 2.13 Hz, 1H) 5.87 (br. s., 1H) 5.59 (m, 1H) 4.75 (m, 1H) 4.60 (m, 1H) 4.26 (d, J=10.79 Hz, 1H) 4.02 (dd, J=11.42, 3.14 Hz, 1H) 3.94 (s, 3H) 3.47 (m, 2H) 3.30 (s, 3H) 2.89 (br. s., 1H) 2.71 (m, 2H) 2.44 (m, 2H) 1.93 (m, 4H) 1.77 (m, 1H) 1.57 (m, 2H) 1.46 (m, 2H) 1.28 (m, 3H) 1.18 (s, 8H) 1.08 (m, 3H) 1.01 (d, J=6.78 Hz, 4H). MS: MS m/z 784.2 (M$^+$+1).

Preparation of Compound 1012 and Compound 1013

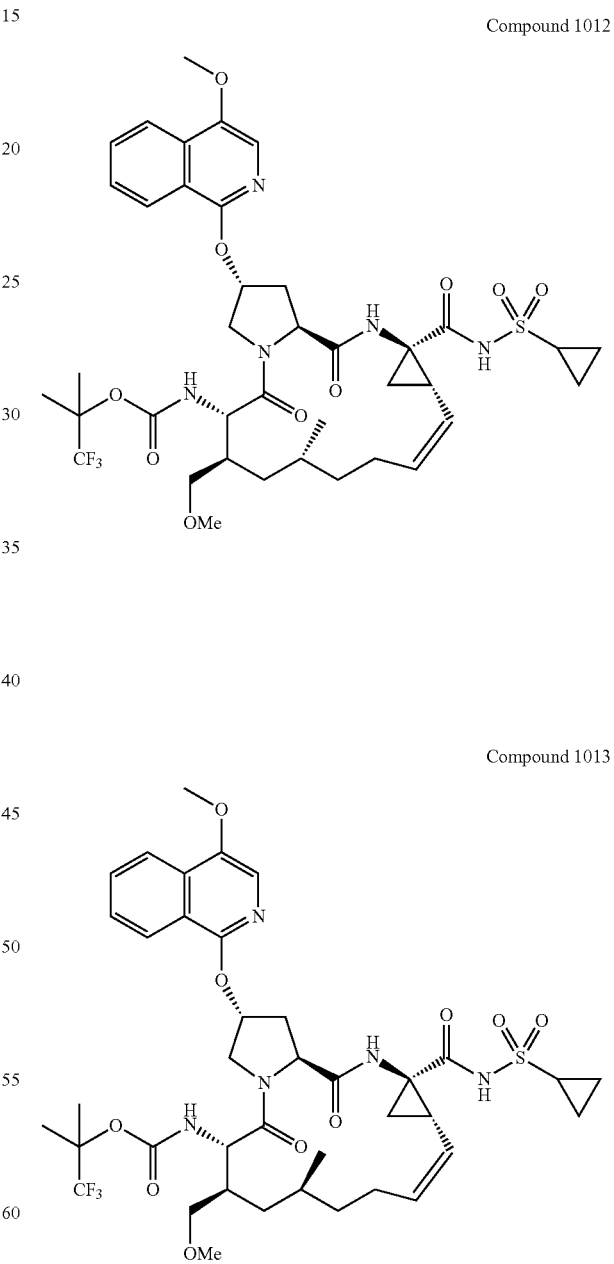

Compound 1012

Compound 1013

Compound 1012 and compound 1013 were prepared using the intermediates described herein and by following the general procedure described for the synthesis of Compound 1016.

Compound 1012: 1,1,1-trifluoro-2-methylpropan-2-yl ((2R,6S,7R,9R,13aS,14aR,16aS,Z)-14a-((cyclopropylsulfonyl)carbamoyl)-2-((4-methoxyisoquinolin-1-yl)oxy)-7-(methoxymethyl)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate.
$^1$H NMR (400 MHz, CD$_3$OD): δ ppm 8.15 (m, 2H) 7.73 (ddd, J=8.28, 7.03, 1.25 Hz, 1H) 7.56 (m, 2H) 5.83 (m, 1H) 5.62 (td, J=10.23, 5.90 Hz, 1H) 5.07 (br. s., 1H) 4.78 (s, 1H) 4.66 (dd, J=10.16, 7.15 Hz, 1H) 4.22 (m, 1H) 4.03 (s, 3H) 3.97 (d, J=3.26 Hz, 1H) 3.44 (m, 2H) 2.93 (d, J=4.52 Hz, 1H) 2.72 (m, 2H) 2.43 (m, 2H) 1.94 (m, 2H) 1.78 (dd, J=8.41, 5.65 Hz, 1H) 1.54 (m, 4H) 1.31 (m, 6H) 1.13 (m, 5H) 1.00 (m, 7H). $^{19}$F NMR (400 MHz, CD$_3$OD): δ ppm −85.2 (s, 3F) MS: MS m/z 836.2 (M$^+$−1).

Compound 1013: 1,1,1-trifluoro-2-methylpropan-2-yl ((2R,6S,7R,9S,13aS,14aR,16aS,Z)-14a-((cyclopropylsulfonyl)carbamoyl)-2-((4-methoxyisoquinolin-1-yl)oxy)-7-(methoxymethyl)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate.
$^1$H NMR (400 MHz, CD$_3$OD): δ ppm 8.20 (m, 1H) 8.19 (d, J=8.28 Hz, 2H) 8.15 (m, 1H) 8.12 (d, J=8.28 Hz, 1H) 7.74 (td, J=7.72, 1.13 Hz, 1H) 7.57 (m, 2H) 5.84 (br. s., 1H) 5.74 (m, 1H) 5.07 (t, J=9.79 Hz, 1H) 4.71 (dd, J=9.54, 7.28 Hz, 1H) 4.53 (m, 2H) 4.02 (m, 4H) 3.47 (m, 2H) 3.38 (s, 3H) 2.93 (tt, J=7.84, 4.96 Hz, 1H) 2.72 (dd, J=13.55, 7.28 Hz, 1H) 2.45 (m, 2H) 2.15 (m, 1H) 1.98 (dd, J=13.80, 7.53 Hz, 1H) 1.72 (dd, J=8.03, 5.52 Hz, 1H) 1.60 (dd, J=9.54, 5.52 Hz, 2H) 1.48 (m, 3H) 1.32 (m, 3H) 1.22 (m, 4H) 1.08 (m, 2H) 0.95 (d, J=6.78 Hz, 4H). $^{19}$F NMR (400 MHz, CD$_3$OD): δ ppm −85.2 (s, 3F). MS: MS m/z 836.2 (M$^+$−1).

Preparation of Compound 1014 and Compound 1015

Compound 1014

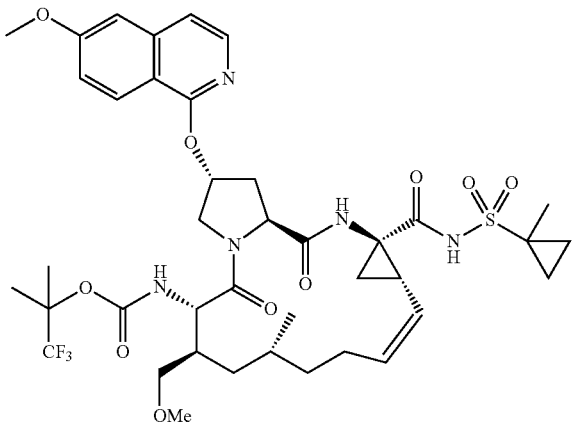

Compound 1015

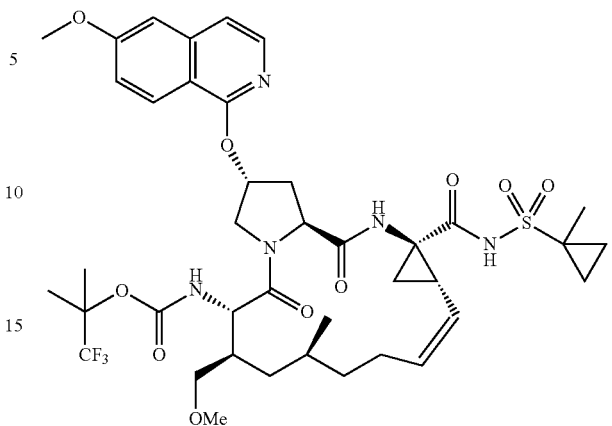

Compound 1014 and compound 1015 were prepared using the intermediates described herein and by following the general procedure described for the synthesis of Compound 1016.

Compound 1014: 1,1,1-trifluoro-2-methylpropan-2-yl ((2R,6S,7R,9R,13aS,14aR,16aS,Z)-2-((6-methoxyisoquinolin-1-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate.
$^1$H NMR (400 MHz, CD$_3$OD): δ ppm 8.11 (d, J=9.29 Hz, 1H) 7.93 (d, J=5.77 Hz, 1H) 7.27 (d, J=6.02 Hz, 1H) 7.21 (d, J=2.51 Hz, 1H) 7.11 (dd, J=9.03, 2.51 Hz, 1H) 5.88 (br. s., 1H) 5.62 (m, 1H) 5.02 (br. s., 1H) 4.77 (d, J=11.54 Hz, 1H) 4.66 (dd, J=10.16, 7.15 Hz, 1H) 4.23 (m, 1H) 4.01 (m, 1H) 3.93 (m, 3H) 3.45 (m, 2H) 3.30 (s, 4H) 2.74 (dt, J=13.30, 6.90 Hz, 2H) 2.44 (ddd, J=13.87, 9.98, 4.27 Hz, 2H) 1.94 (m, 2H) 1.77 (dd, J=8.41, 5.65 Hz, 1H) 1.56 (m, 6H) 1.44 (m, 2H) 1.36 (s, 3H) 1.27 (m, 4H) 1.04 (m, 3H) 1.00 (d, J=6.78 Hz, 3H) 0.90 (m, 2H). $^{19}$F NMR (400 MHz, CD$_3$OD): δ ppm −85.13 (s, 3F). MS: MS m/z 850.2 (M$^+$−1).

Compound 1015: 1,1,1-trifluoro-2-methylpropan-2-yl ((2R,6S,7R,9S,13aS,14aR,16aS,Z)-2-((6-methoxyisoquinolin-1-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate.
$^1$H NMR (400 MHz, CD$_3$OD): δ ppm 8.14 (d, J=9.04 Hz, 1H) 7.92 (d, J=6.02 Hz, 1H) 7.27 (d, J=5.77 Hz, 1H) 7.21 (d, J=2.51 Hz, 1H) 7.12 (dd, J=9.16, 2.38 Hz, 1H) 5.88 (br. s., 1H) 5.70 (br. s., 1H) 4.71 (m, 1H) 4.58 (m, 2H) 4.47 (d, J=11.54 Hz, 1H) 4.06 (d, J=9.29 Hz, 1H) 3.94 (s, 3H) 3.50 (d, J=1.51 Hz, 2H) 3.40 (s, 3H) 2.72 (dd, J=13.55, 7.28 Hz, 1H) 2.46 (m, 2H) 2.15 (br. s., 1H) 1.97 (m, 2H) 1.73 (br. s., 1H) 1.59 (m, 2H) 1.49 (m, 8H) 1.35 (m, 6H) 1.20 (m, 1H) 0.94 (d, J=6.53 Hz, 3H) 0.85 (br. s., 2H). $^{19}$F NMR (400 MHz, CD$_3$OD): δ ppm −85.12 (s, 3F). MS: MS m/z 850.2 (M$^+$−1).

Preparation of Compound 1018 and Compound 1019

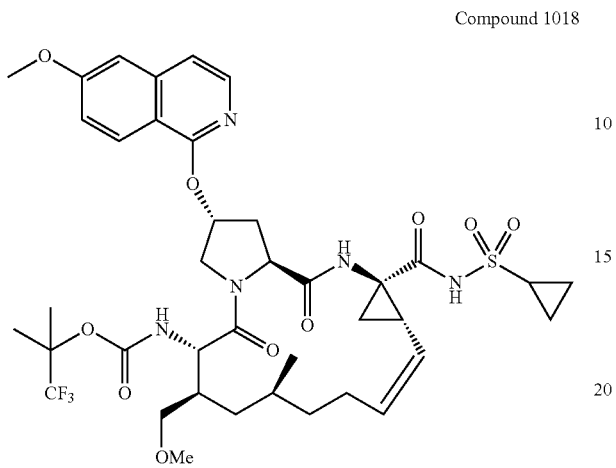

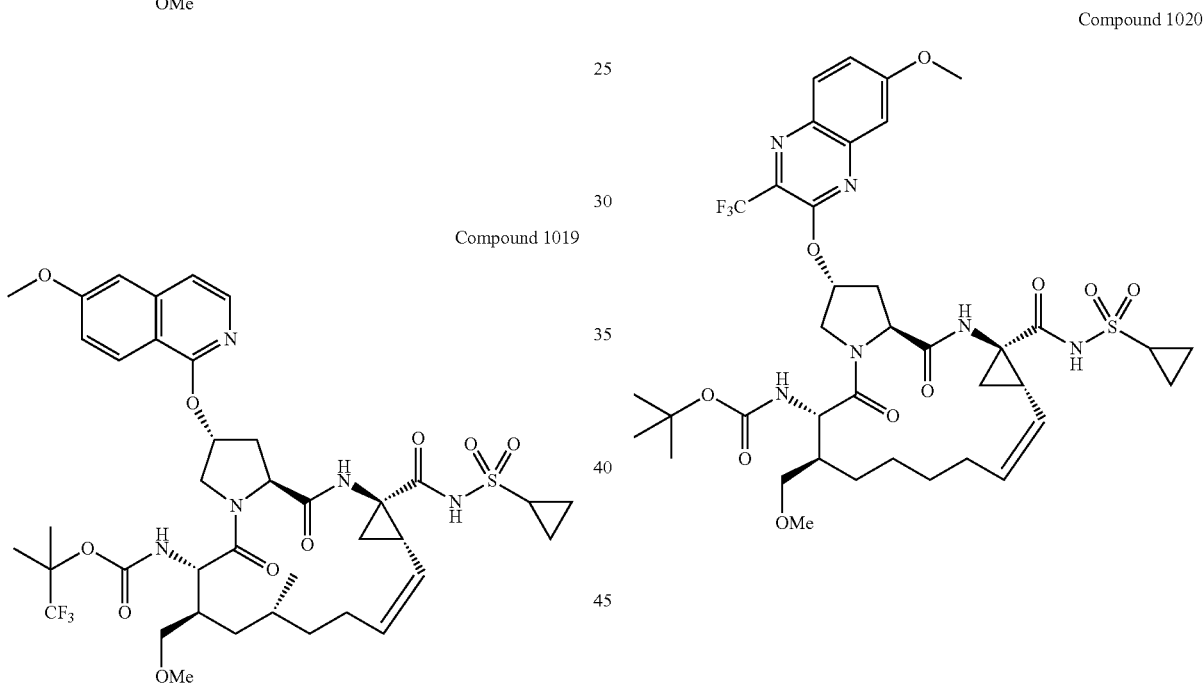

Compound 1018 and compound 1019 were prepared using the intermediates described herein and by following the general procedure described for the synthesis of Compound 1016.

Compound 1018: 1,1,1-trifluoro-2-methylpropan-2-yl ((2R,6S,7R,9S,13aS,14aR,16aS,Z)-14a-((cyclopropylsulfonyl)carbamoyl)-2-((6-methoxyisoquinolin-1-yl)oxy)-7-(methoxymethyl)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate.
$^1$H NMR (400 MHz, CD$_3$OD): δ ppm 8.14 (d, J=9.29 Hz, 1H) 7.93 (m, 1H) 7.28 (d, J=5.77 Hz, 1H) 7.22 (d, J=2.51 Hz, 1H) 7.12 (dd, J=9.03, 2.51 Hz, 1H) 5.89 (br. s., 1H) 5.74 (m, 1H) 5.08 (t, J=9.54 Hz, 1H) 4.81 (s, 1H) 4.71 (dd, J=9.54, 7.53 Hz, 1H) 4.55 (m, 1H) 4.04 (dd, J=11.54, 3.51 Hz, 1H) 3.95 (s, 3H) 3.48 (d, J=5.52 Hz, 2H) 3.38 (m, 8H) 3.28 (dt, J=3.33, 1.73 Hz, 2H) 2.93 (m, 1H) 2.72 (m, 2H) 2.45 (m, 2H) 1.72 (dd, J=8.28, 5.52 Hz, 1H) 1.55 (m, 5H) 1.32 (m, 3H) 1.06 (m, 5H). $^{19}$F NMR (400 MHz, CD$_3$OD): δ ppm −85.01 (s, 3F). MS: MS m/z 838.2 (M$^+$+1).

Compound 1019: 1,1,1-trifluoro-2-methylpropan-2-yl ((2R,6S,7R,9R,13aS,14aR,16aS,Z)-14a-((cyclopropylsulfonyl)carbamoyl)-2-((6-methoxyisoquinolin-1-yl)oxy)-7-(methoxymethyl)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate.
MS: MS m/z 838.2 (M$^+$+1).

Preparation of Compound 1020

Compound 1020 was prepared using the intermediates described herein and by following the general procedure described for the synthesis of Compound 1010.

Compound 1020: tert-butyl ((2R,6S,7R,13aS,14aR,16aS,Z)-14a-((cyclopropylsulfonyl)carbamoyl)-2-((7-methoxy-3-(trifluoromethyl)quinoxalin-2-yl)oxy)-7-(methoxymethyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, CD$_3$OD): δ ppm 7.97 (d, J=9.03 Hz, 1H) 7.38 (m, 2H) 5.97 (br. s., 1H) 5.66 (d, J=8.78 Hz, 1H) 4.66 (dd, J=9.54, 7.28 Hz, 1H) 4.19 (m, 1H) 4.04 (m, 4H) 3.40 (m, 3H) 3.28 (m, 4H) 2.89 (br. s., 1H) 2.70 (dd, J=13.68, 6.90 Hz, 1H) 2.55 (m, 3H) 1.99 (s, 2H) 1.85 (m, 1H) 1.76 (m, 1H) 1.63 (dd, J=9.41, 5.14 Hz, 2H) 1.45 (m, 7H) 1.08 (m, 10H). $^{19}$F NMR (400 MHz, CD$_3$OD): δ ppm −68.70 (s, 3F). MS: MS m/z 837.2 (M$^+$−1).

Preparation of Compound 1021

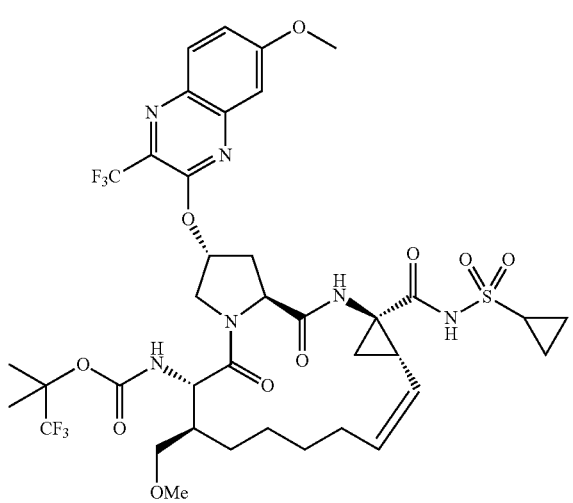

Compound 1021

Compound 1021 was prepared using the intermediates described herein and by following the general procedure described for the synthesis of Compound 1016.
Compound 1021: 1,1,1-trifluoro-2-methylpropan-2-yl ((2R,6S,7R,13aS,14aR,16aS,Z)-14a-((cyclopropylsulfonyl)carbamoyl)-2-((7-methoxy-3-(trifluoromethyl)quinoxalin-2-yl)oxy)-7-(methoxymethyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, CD$_3$OD): δ ppm 7.99 (d, J=9.29 Hz, 1H) 7.40 (m, 1H) 7.24 (d, J=7.53 Hz, 1H) 5.97 (br. s., 1H) 5.69 (d, J=9.79 Hz, 1H) 5.10 (t, J=9.66 Hz, 1H) 4.91 (br. s., 2H) 4.81 (s, 1H) 4.68 (dd, J=9.79, 7.03 Hz, 2H) 4.15 (dd, J=10.92, 7.65 Hz, 2H) 4.01 (m, 3H) 3.39 (m, 3H) 3.28 (m, 2H) 2.55 (m, 4H) 1.90 (t, J=10.04 Hz, 2H) 1.75 (dd, J=8.28, 5.52 Hz, 2H) 1.64 (dd, J=9.54, 5.52 Hz, 2H) 1.46 (m, 3H) 1.32 (m, 6H) 1.07 (m, 4H). $^{19}$F NMR (400 MHz, CD$_3$OD): δ ppm −68.72 (s, 3F) −85.26 (s, 3F). MS: MS m/z 891.0 (M$^+$−1).

Preparation of Compound 1022

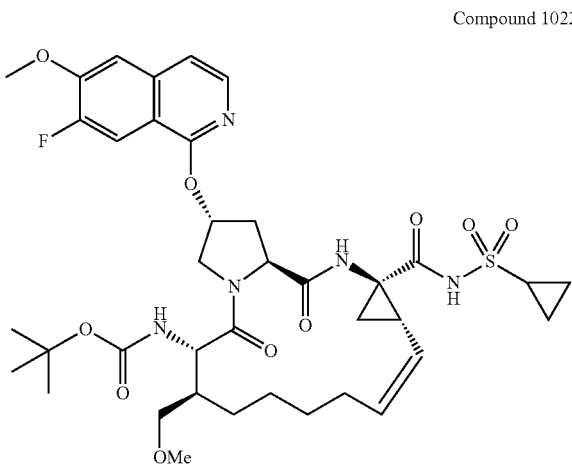 [SMILES: COC[C@@H]1CCCC/C=C\[C@@H]2C[C@@]2(C(=O)NS(=O)(=O)C2CC2)NC(=O)[C@@H]2C[C@@H](Oc3nccc4cc(OC)c(F)cc34)CN2C(=O)[C@H]1NC(=O)OC(C)(C)C(F)(F)F]

Compound 1022

Compound 1022 was prepared using the intermediates described herein and by following the general procedure described for the synthesis of Compound 1010.
Compound 1022: tert-butyl ((2R,6S,7R,13aS,14aR,16aS,Z)-14a-((cyclopropylsulfonyl)carbamoyl)-2-((7-fluoro-6-methoxynaphthalen-1-yl)oxy)-7-(methoxymethyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, CD$_3$OD): δ ppm 7.93 (m, 1H) 7.79 (d, J=11.54 Hz, 1H) 7.38 (d, J=8.28 Hz, 1H) 7.29 (d, J=6.02 Hz, 1H) 5.89 (br. s., 1H) 5.68 (m, 1H) 5.09 (m, 1H) 4.76 (m, 1H) 4.65 (dd, J=9.66, 7.15 Hz, 1H) 4.24 (d, J=10.79 Hz, 1H) 4.00 (m, 3H) 3.45 (br. s., 2H) 3.29 (s, 3H) 2.93 (tt, J=7.87, 4.93 Hz, 1H) 2.73 (m, 1H) 2.52 (m, 3H) 1.93 (m, 5H) 1.75 (m, 3H) 1.44 (m, 8H) 1.07 (m, 10H). MS: MS m/z 786.2 (M$^+$−1).

Preparation of Compound 1023

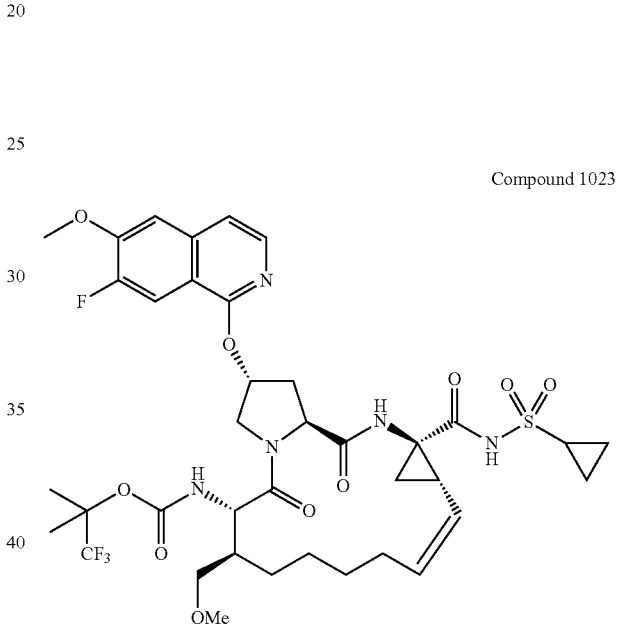

Compound 1023

Compound 1023 was prepared using the intermediates described herein and by following the general procedure described for the synthesis of Compound 1016.
Compound 1023: 1,1,1-trifluoro-2-methylpropan-2-yl ((2R,6S,7R,13aS,14aR,16aS,Z)-14a-((cyclopropylsulfonyl)carbamoyl)-2-((7-fluoro-6-methoxynaphthalen-1-yl)oxy)-7-(methoxymethyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, CD$_3$OD): δ ppm 7.95 (d, J=5.77 Hz, 1H) 7.80 (d, J=11.80 Hz, 1H) 7.40 (d, J=8.03 Hz, 1H) 7.30 (d, J=5.77 Hz, 1H) 5.89 (br. s., 1H) 5.69 (m, 1H) 5.10 (m, 1H) 4.70 (m, 2H) 4.23 (d, J=10.79 Hz, 1H) 4.00 (m, 4H) 3.45 (m, 2H) 3.38 (m, 3H) 3.29 (m, 4H) 2.94 (tt, J=7.91, 4.89 Hz, 1H) 2.74 (dd, J=13.80, 6.78 Hz, 1H) 2.52 (m, 3H) 1.95 (m, 2H) 1.76 (dd, J=8.28, 5.52 Hz, 1H) 1.62 (dd, J=9.41, 5.40 Hz, 1H) 1.45 (m, 7H) 1.31 (m, 1H) 1.08 (m, 6H). $^{19}$F NMR (400 MHz, CD$_3$OD): δ ppm −85.23 (s, 3F) −133.68 (s, 1F). MS: MS m/z 840.2 (M$^+$−1).

Preparation of Compound 1024 and Compound 1025

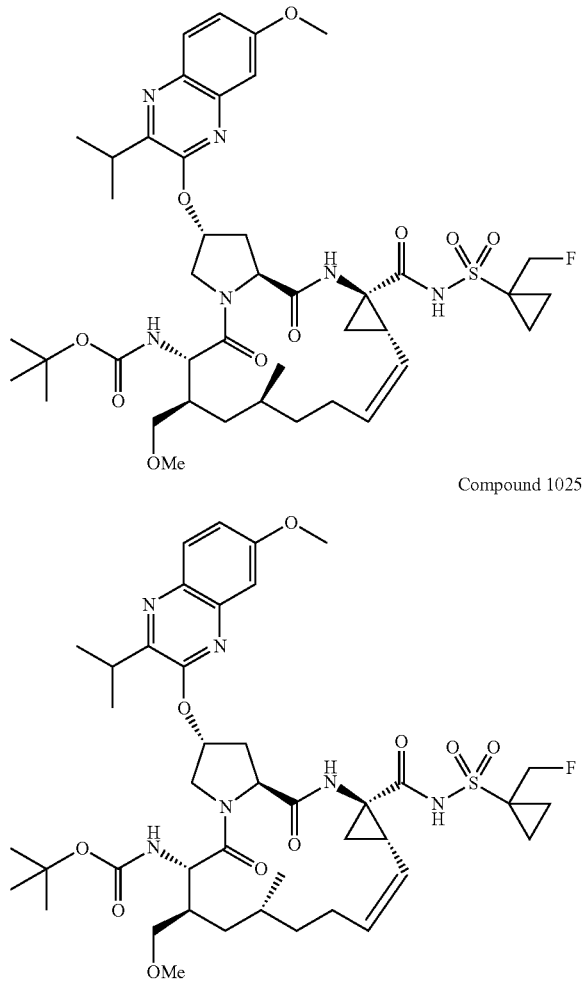

Compound 1024

Compound 1025

Compound 1024 and compound 1025 were prepared using the intermediates described herein and by following the general procedure described for the synthesis of Compound 1010.

Compound 1024: tert-butyl ((2R,6S,7R,9S,13aS,14aR, 16aS,Z)-14a-(((1-(fluoromethyl)cyclopropyl)sulfonyl)carbamoyl)-2-((3-isopropyl-7-methoxyquinoxalin-2-yl)oxy)-7-(methoxymethyl)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate.
$^1$H NMR (400 MHz, CD$_3$OD): δ ppm 7.84 (d, J=9.04 Hz, 1H) 7.27 (d, J=2.51 Hz, 1H) 7.24 (s, 1H) 5.98 (br. s., 1H) 5.69 (br. s., 1H) 4.67 (m, 3H) 4.40 (d, J=11.55 Hz, 1H) 4.13 (d, J=8.53 Hz, 1H) 3.96 (s, 3H) 3.48 (m, 5H) 2.68 (m, 2H) 2.53 (m, 2H) 1.98 (m, 5H) 1.62 (m, 12H) 1.32 (m, 14H) 0.94 (m, 5H). MS: MS m/z 859.4 (M$^+$+1).

sCompound 1025: tert-butyl ((2R,6S,7R,9R,13aS,14aR, 16aS,Z)-14a-(((1-(fluoromethyl)cyclopropyl)sulfonyl)carbamoyl)-2-((3-isopropyl-7-methoxyquinoxalin-2-yl)oxy)-7-(methoxymethyl)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate.

$^1$H NMR (400 MHz, CD$_3$OD): δ ppm 7.83 (d, J=9.04 Hz, 1H) 7.26 (d, J=2.51 Hz, 1H) 7.21 (dd, J=9.04, 3.01 Hz, 1H) 5.95 (br. s., 1H) 5.59 (d, J=5.02 Hz, 1H) 4.66 (m, 3H) 4.26 (d, J=11.04 Hz, 1H) 4.09 (m, 1H) 3.95 (m, 3H) 3.48 (m, 3H) 3.28 (s, 3H) 2.67 (m, 2H) 2.46 (m, 2H) 1.94 (m, 3H) 1.73 (m, 1H) 1.54 (m, 5H) 1.30 (m, 7H) 1.19 (m, 14H) 0.98 (m, 4H). MS: MS m/z 859.4 (M$^+$+1).

Preparation of Compound 1026

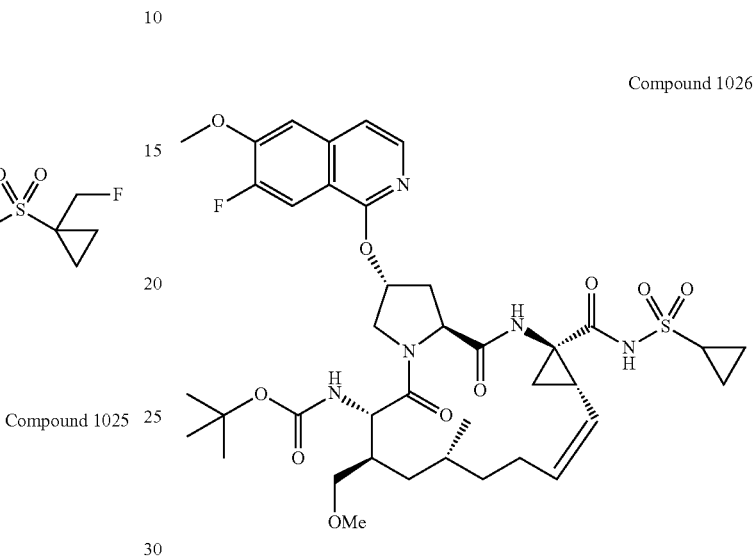

Compound 1026

Compound 1026 was prepared using the intermediates described herein and by following the general procedure described for the synthesis of Compound 1010.

Compound 1026: tert-butyl ((2R,6S,7R,9R,13aS,14aR, 16aS,Z)-14a-((cyclopropylsulfonyl)carbamoyl)-2-((7-fluoro-6-methoxynaphthalen-1-yl)oxy)-7-(methoxymethyl)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 802 (M$^+$+1).

Preparation of Compound 1027 and Compound 1028

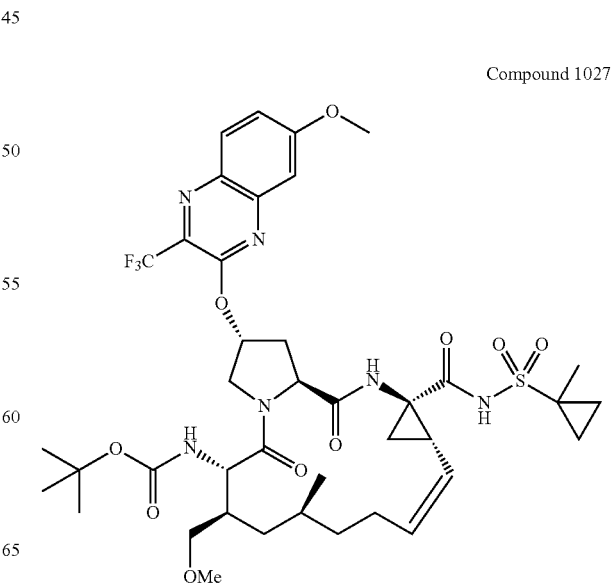

Compound 1027

Preparation of Compound 1029 and Compound 1030

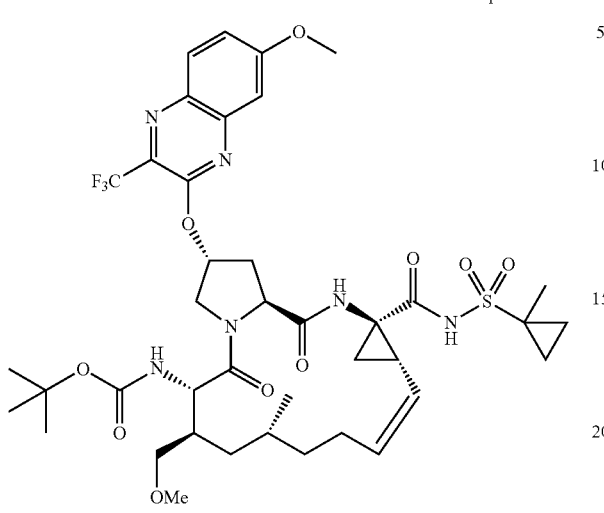

Compound 1028

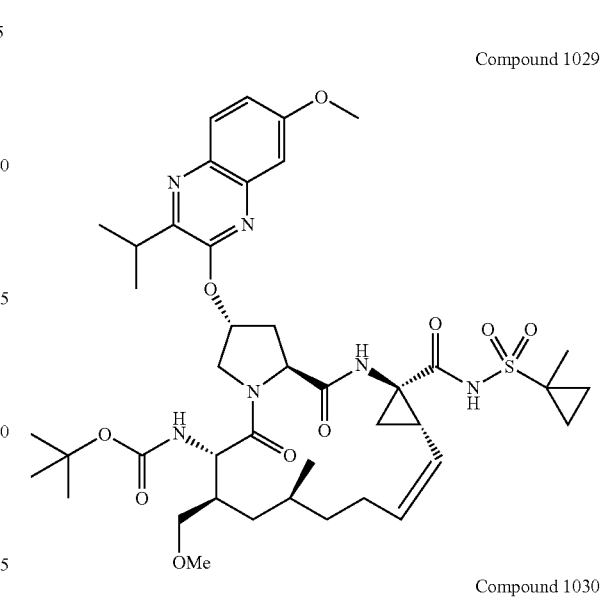

Compound 1029

Compound 1030

Compound 1027 and compound 1028 were prepared using the intermediates described herein and by following the general procedure described for the synthesis of Compound 1010.

Compound 1027: tert-butyl ((2R,6S,7R,9S,13aS,14aR, 16aS,Z)-2-((7-methoxy-3-(trifluoromethyl)quinoxalin-2-yl) oxy)-7-(methoxymethyl)-9-methyl-14a-(((1-methylcyclopropyl)sulfonyl)carbamoyl)-5,16-dioxo-1,2,3,5,6,7,8,9,10, 11,13a,14,14a,15,16,16a-hexadecahydrocyclopropa[e] pyrrolo[1,2-a][1,4]diazacyclopentadecin-6-yl)carbamate.
$^1$H NMR (400 MHz, CD$_3$OD): δ ppm 7.98 (d, J=9.04 Hz, 1H) 7.38 (m, 2H) 6.02 (br. s., 1H) 5.69 (br. s., 1H) 4.69 (m, 1H) 4.55 (m, 2H) 4.13 (d, J=8.53 Hz, 1H) 4.01 (m, 3H) 3.48 (m, 5H) 2.68 (m, 1H) 2.55 (m, 2H) 2.00 (m, 3H) 1.74 (m, 5H) 1.57 (m, 8H) 1.31 (m, 14H) 0.95 (m, 4H). MS: MS m/z 865.2 (M$^+$−1).

Compound 1028: tert-butyl ((2R,6S,7R,9R,13aS,14aR, 16aS,Z)-2-((7-methoxy-3-(trifluoromethyl)quinoxalin-2-yl) oxy)-7-(methoxymethyl)-9-methyl-14a-(((1-methylcyclopropyl)sulfonyl)carbamoyl)-5,16-dioxo-1,2,3,5,6,7,8,9,10, 11,13a,14,14a,15,16,16a-hexadecahydrocyclopropa[e] pyrrolo[1,2-a][1,4]diazacyclopentadecin-6-yl)carbamate.
$^1$H NMR (400 MHz, CD$_3$OD): δ ppm 7.96 (m, 1H) 7.38 (m, 2H) 5.98 (br. s., 1H) 5.62 (m, 1H) 4.99 (m, 1H) 4.63 (m, 1H) 4.16 (m, 1H) 4.04 (m, 4H) 3.45 (m, 2H) 3.27 (s, 3H) 2.72 (m, 2H) 2.48 (m, 2H) 1.93 (m, 2H) 1.77 (m, 2H) 1.61 (m, 3H) 1.46 (m, 5H) 1.27 (m, 4H) 1.07 (s, 9H) 0.95 (m, 5H). MS: MS m/z 865.2 (M$^+$−1).

Compound 1029 and compound 1030 were prepared using the intermediates described herein and by following the general procedure described for the synthesis of Compound 1010.

Compound 1029: tert-butyl ((2R,6S,7R,9S,13aS,14aR, 16aS,Z)-2-((3-isopropyl-7-methoxyquinoxalin-2-yl)oxy)-7-(methoxymethyl)-9-methyl-14a-(((1-methylcyclopropyl) sulfonyl)carbamoyl)-5,16-dioxo-1,2,3,5,6,7,8,9,10,11,13a, 14,14a,15,16,16a-hexadecahydrocyclopropa[e]pyrrolo[1,2-a][1,4]diazacyclopentadecin-6-yl)carbamate. $^1$H NMR (400 MHz, CD$_3$OD): δ ppm 7.83 (d, J=9.04 Hz, 1H) 7.23 (m, 2H) 5.96 (br. s., 1H) 5.64 (br. s., 1H) 4.66 (m, 2H) 4.26 (d, J=10.54 Hz, 1H) 4.08 (d, J=9.54 Hz, 1H) 3.96 (s, 3H) 3.48 (m, 4H) 3.29 (s, 3H) 2.71 (br. s., 1H) 2.48 (m, 2H) 1.94 (d, J=17.07 Hz, 1H) 1.78 (m, 2H) 1.50 (m, 7H) 1.32 (m, 9H) 1.17 (m, 11H) 0.92 (m, 5H). MS: MS m/z 839.2 (M$^+$−1).

Compound 1030: tert-butyl ((2R,6S,7R,9R,13aS,14aR, 16aS,Z)-2-((3-isopropyl-7-methoxyquinoxalin-2-yl)oxy)-7-(methoxymethyl)-9-methyl-14a-(((1-methylcyclopropyl) sulfonyl)carbamoyl)-5,16-dioxo-1,2,3,5,6,7,8,9,10,11,13a, 14,14a,15,16,16a-hexadecahydrocyclopropa[e]pyrrolo[1,2-a][1,4]diazacyclopentadecin-6-yl)carbamate. $^1$H NMR (400 MHz, CD$_3$OD): δ ppm 7.84 (d, J=9.04 Hz, 1H) 7.24 (m, 2H) 5.96 (br. s., 1H) 5.61 (br. s., 1H) 4.62 (m, 2H) 4.37 (br. s., 1H) 4.17 (br. s., 1H) 3.96 (s, 3H) 2.65 (m, 1H) 2.01 (m, 2H) 1.79 (m, 7H) 1.57 (m, 12H) 1.40-1.32 (m, 19H) 0.93 (m, 5H). MS: MS m/z 839.2 (M$^+$−1).

Preparation of Compound 1031 and Compound 1032

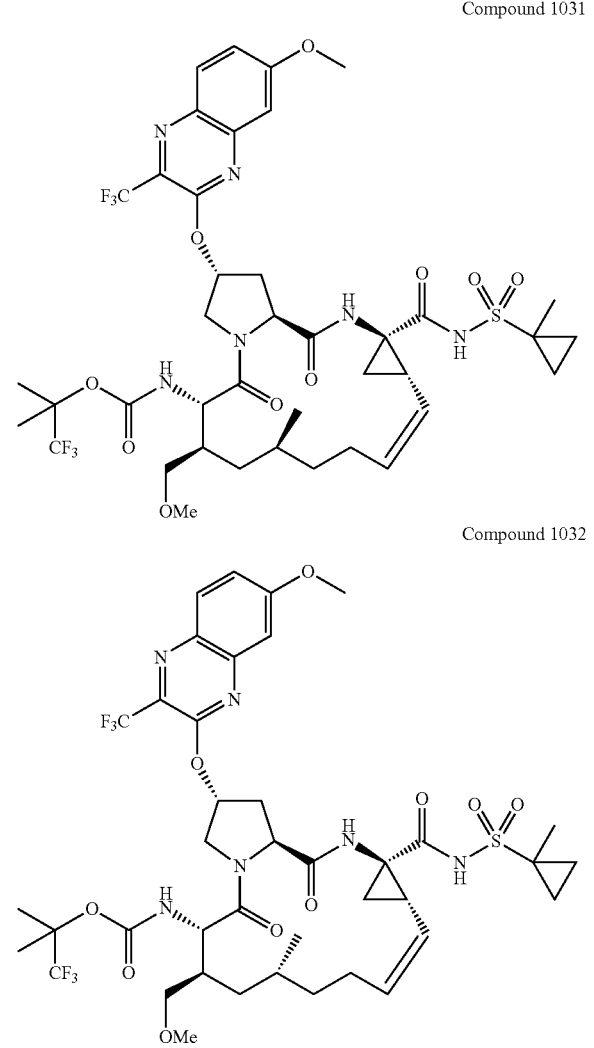

Compound 1031

Compound 1032

Compound 1031 and compound 1032 were prepared using the intermediates described herein and by following the general procedure described for the synthesis of Compound 1016.

Compound 1031: 1,1,1-trifluoro-2-methylpropan-2-yl ((2R,6S,7R,9S,13aS,14aR,16aS,Z)-2-((7-methoxy-3-(trifluoromethyl)quinoxalin-2-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 921.2 (M$^+$+1).

Compound 1032: 1,1,1-trifluoro-2-methylpropan-2-yl ((2R,6S,7R,9R,13aS,14aR,16aS,Z)-2-((7-methoxy-3-(trifluoromethyl)quinoxalin-2-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, CD$_3$OD): δ ppm 7.99 (d, J=9.04 Hz, 1H) 7.40 (m, 2H) 5.98 (br. s., 1H) 5.63 (m, 1H) 5.01 (m, 1H) 4.13 (m, 1H) 4.04 (m, 4H) 3.45 (m, 2H) 3.27 (m, 3H) 2.71 (m, 2H) 2.48 (m, 2H) 1.94 (m, 2H) 1.77 (dd, J=8.28, 5.77 Hz, 1H) 1.67 (d, J=10.04 Hz, 1H) 1.59 (m, 1H) 1.53 (s, 4H) 1.43 (m, 2H) 1.20 (d, J=9.54 Hz, 6H) 1.00 (m, 7H) 0.90 (m, 3H). $^{19}$F NMR (400 MHz, CD$_3$OD): δ ppm −68.72 (s, 3F) −85.26 (s, 3F). MS: MS m/z 921.2 (M$^+$+1).

Preparation of Compound 1033 and Compound 1034

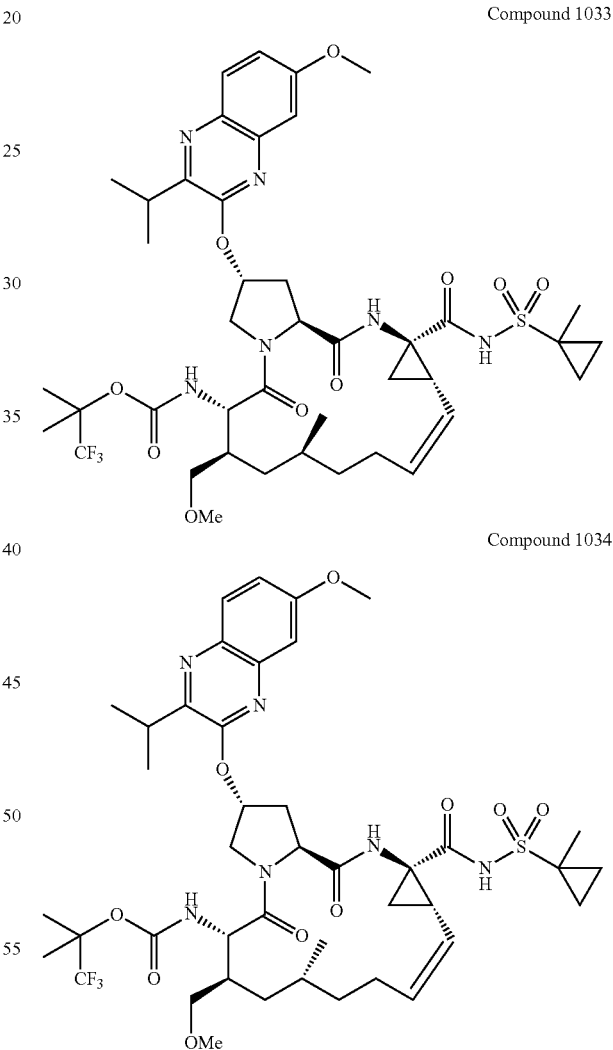

Compound 1033

Compound 1034

Compound 1033 and compound 1034 were prepared using the intermediates described herein and by following the general procedure described for the synthesis of Compound 1016.

Compound 1033: 1,1,1-trifluoro-2-methylpropan-2-yl ((2R,6S,7R,9S,13aS,14aR,16aS,Z)-2-((3-isopropyl-7-methoxyquinoxalin-2-yl)oxy)-7-(methoxymethyl)-9-methyl-14a-

(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, CD$_3$OD): δ ppm 7.84 (d, J=9.04 Hz, 1H) 7.29 (d, J=3.01 Hz, 1H) 7.23 (m, 1H) 5.98 (br. s., 1H) 5.75 (d, J=10.54 Hz, 1H) 5.02 (m, 1H) 4.72 (t, J=8.53 Hz, 1H) 4.57 (m, 1H) 4.45 (d, J=12.55 Hz, 1H) 4.09 (m, 1H) 3.97 (s, 3H) 3.47 (m, 7H) 2.70 (m, 1H) 2.48 (m, 1H) 1.99 (m, 1H) 1.72 (m, 1H) 1.63 (m, 2H) 1.52 (m, 5H) 1.45 (m, 7H) 1.34 (m, 12H) 0.93 (m, 4H). $^{19}$F NMR (400 MHz, CD$_3$OD): δ ppm −85.1 (s, 3F) MS: MS m/z 893.2 (M$^+$−1).

Compound 1034: 1,1,1-trifluoro-2-methylpropan-2-yl ((2R,6S,7R,9R,13aS,14aR,16aS,Z)-2-((3-isopropyl-7-methoxyquinoxalin-2-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 893.2 (M$^+$−1).

Compound 1035 and compound 1036 were prepared using the intermediates described herein and by following the general procedure described for the synthesis of Compound 1010.

Compound 1035: tert-butyl ((2R,6S,7R,9R,13aS,14aR,16aS,Z)-14a-(((1-(fluoromethyl)cyclopropyl)sulfonyl)carbamoyl)-2-((7-methoxy-3-(trifluoromethyl)quinoxalin-2-yl)oxy)-7-(methoxymethyl)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 884.2 (M$^+$−1).

Compound 1036: tert-butyl ((2R,6S,7R,9R,13aS,14aR,16aS,Z)-14a-(((1-(fluoromethyl)cyclopropyl)sulfonyl)carbamoyl)-2-((3-isopropyl-7-methoxyquinoxalin-2-yl)oxy)-7-(methoxymethyl)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 884.2 (M$^+$−1).

Preparation of Compound 1037 and Compound 1038

Preparation of Compound 1035 and Compound 1036

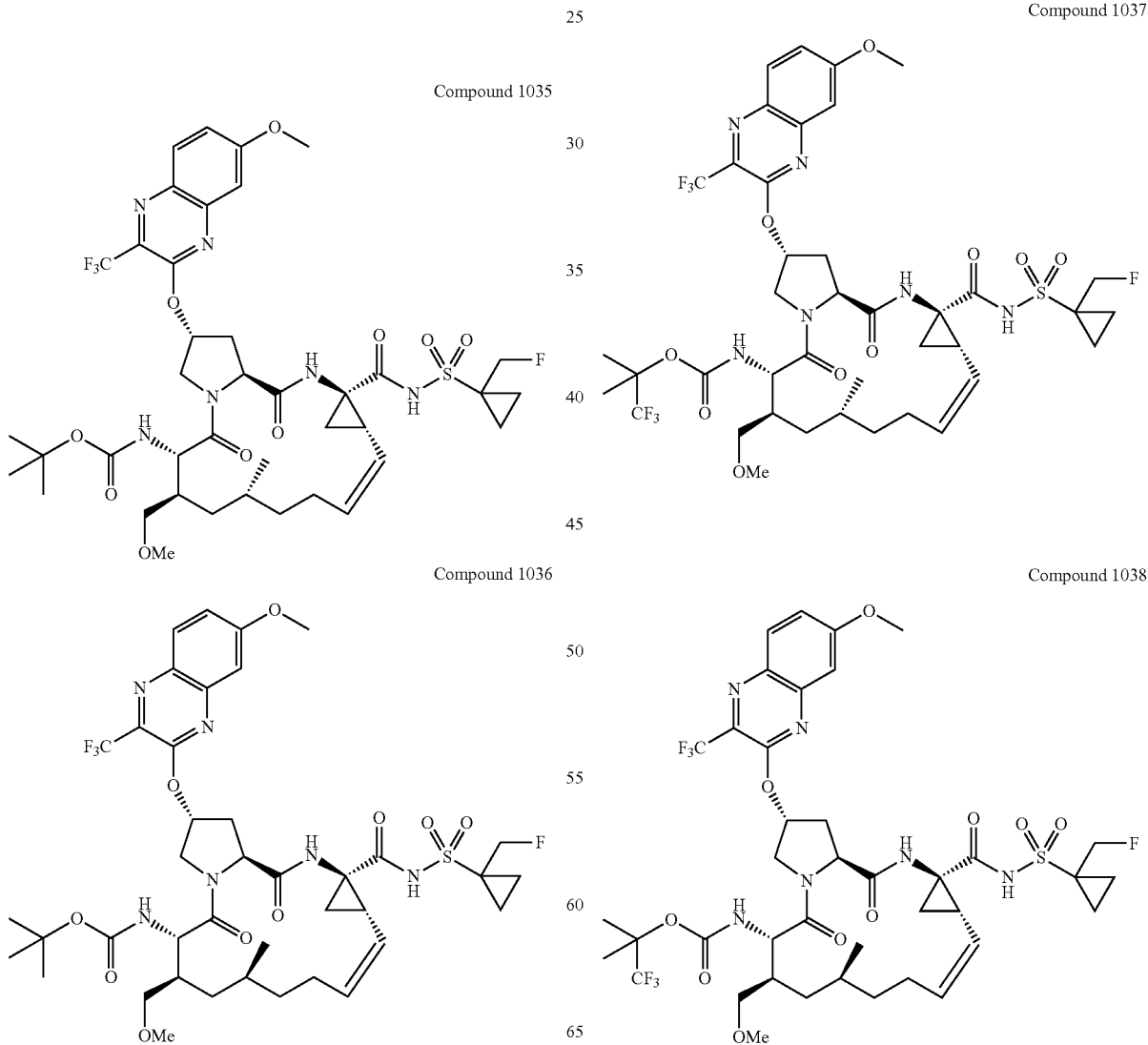

Compound 1035

Compound 1036

Compound 1037

Compound 1038

Compound 1037 and compound 1038 were prepared using the intermediates described herein and by following the general procedure described for the synthesis of Compound 1016.

Compound 1037: 1,1,1-trifluoro-2-methylpropan-2-yl ((2R,6S,7R,9R,13aS,14aR,16aS,Z)-14a-(((1-(fluoromethyl)cyclopropyl)sulfonyl)carbamoyl)-2-((7-methoxy-3-(trifluoromethyl)quinoxalin-2-yl)oxy)-7-(methoxymethyl)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, CD$_3$OD): δ ppm 7.98 (m, 1H) 7.38 (m, 2H) 5.96 (br. s., 1H) 5.57 (br. s., 1H) 4.67 (m, 3H) 4.14 (d, J=11.04 Hz, 1H) 4.01 (m, 4H) 3.46 (m, 3H) 3.26 (m, 3H) 2.71 (m, 1H) 2.47 (m, 1H) 1.93 (m, 4H) 1.66 (m, 5H) 1.38 (m, 5H) 1.07 (m, 11H). MS: MS m/z 939.2 (M$^+$+1).

Compound 1038: 1,1,1-trifluoro-2-methylpropan-2-yl ((2R,6S,7R,9S,13aS,14aR,16aS,Z)-14a-(((1-(fluoromethyl)cyclopropyl)sulfonyl)carbamoyl)-2-((7-methoxy-3-(trifluoromethyl)quinoxalin-2-yl)oxy)-7-(methoxymethyl)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, CD$_3$OD): δ ppm 7.98 (d, J=9.04 Hz, 1H) 7.39 (m, 2H) 5.95 (br. s., 1H) 5.61 (br. s., 1H) 4.60 (m, 5H) 4.12 (d, J=8.53 Hz, 1H) 4.00 (m, 3H) 3.51 (m, 2H) 3.43 (s, 3H) 2.64 (m, 2H) 2.00 (m, 2H) 1.73 (br. s., 2H) 1.49 (m, 6H) 1.32 (m, 9H) 1.06 (br. s., 2H) 0.92 (d, J=6.53 Hz, 3H). MS: MS m/z 939.2 (M$^+$+1).

Preparation of Compound 1039 and Compound 1040

Compound 1039

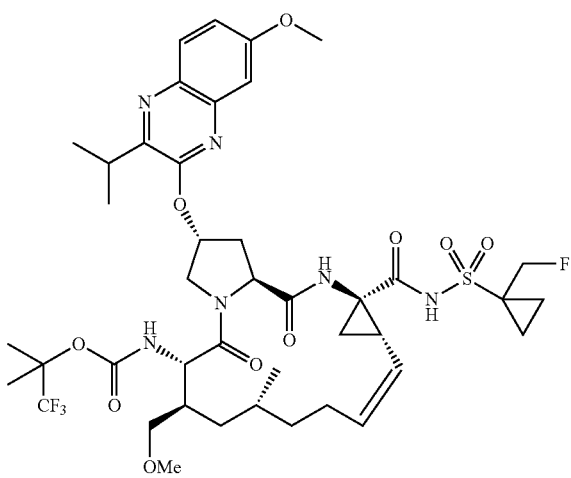

Compound 1040

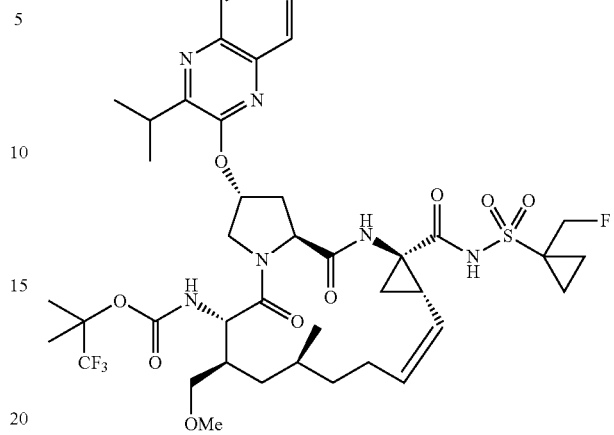

Compound 1039 and compound 1040 were prepared using the intermediates described herein and by following the general procedure described for the synthesis of Compound 1016.

Compound 1039: 1,1,1-trifluoro-2-methylpropan-2-yl ((2R,6S,7R,9R,13aS,14aR,16aS,Z)-14a-(((1-(fluoromethyl)cyclopropyl)sulfonyl)carbamoyl)-2-(3-isopropyl-7-methoxyquinoxalin-2-yl)oxy)-7-(methoxymethyl)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, CD$_3$OD): δ ppm 7.83 (d, J=9.04 Hz, 1H) 7.28 (d, J=3.01 Hz, 1H) 7.22 (dd, J=9.29, 2.76 Hz, 1H) 5.92 (br. s., 1H) 5.59 (d, J=5.52 Hz, 1H) 4.65 (m, 3H) 4.24 (d, J=11.04 Hz, 1H) 4.07 (dd, J=11.80, 3.26 Hz, 1H) 3.95 (m, 3H) 3.46 (m, 3H) 3.26 (m, 3H) 2.56 (m, 3H) 1.94 (m, 2H) 1.61 (m, 6H) 1.33 (m, 11H) 1.21 (m, 9H) 1.01 (d, J=6.53 Hz, 3H). $^{19}$F NMR (400 MHz, CD$_3$OD): δ ppm −85.1 (s, 3F). MS: MS m/z 913.4 (M$^+$+1).

Compound 1040: 1,1,1-trifluoro-2-methylpropan-2-yl ((2R,6S,7R,9S,13aS,14aR,16aS,Z)-14a-(((1-(fluoromethyl)cyclopropyl)sulfonyl)carbamoyl)-2-((3-isopropyl-7-methoxyquinoxalin-2-yl)oxy)-7-(methoxymethyl)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, CD$_3$OD): δ ppm 7.84 (d, J=9.04 Hz, 1H) 7.28 (d, J=3.01 Hz, 1H) 7.22 (m, 1H) 5.94 (br. s., 1H) 5.67 (br. s., 1H) 4.62 (m, 3H) 4.44 (d, J=12.05 Hz, 1H) 3.96 (m, 3H) 3.48 (m, 5H) 2.69 (m, 2H) 1.57 (m, 9H) 1.32 (m, 11H) 1.21 (m, 9H) 0.93 (m, 4H). MS: MS m/z 913.4 (M$^+$+1).

Preparation of Compound 1041 and Compound 1042

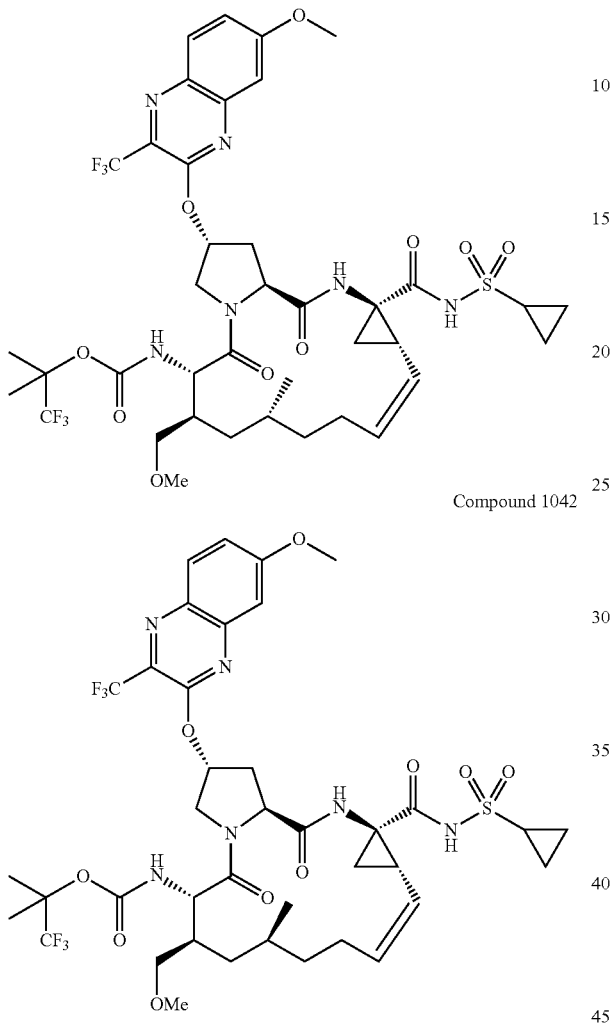

Compound 1041

Compound 1042

Compound 1041 and compound 1042 were prepared using the intermediates described herein and by following the general procedure described for the synthesis of Compound 1016.

Compound 1041: 1,1,1-trifluoro-2-methylpropan-2-yl ((2R,6S,7R,9R,13aS,14aR,16aS,Z)-14a-((cyclopropylsulfonyl)carbamoyl)-2-((7-methoxy-3-(trifluoromethyl)quinoxalin-2-yl)oxy)-7-(methoxymethyl)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, CD$_3$OD): δ ppm 8.00 (m, 1H) 7.39 (m, 2H) 5.97 (br. s., 1H) 5.62 (td, J=9.91, 5.77 Hz, 1H) 5.07 (br. s., 1H) 4.64 (m, 1H) 4.12 (d, J=11.04 Hz, 1H) 4.01 (m, 4H) 3.43 (m, 2H) 3.28 (m, 3H) 2.94 (br. s., 1H) 2.71 (m, 2H) 2.47 (m, 2H) 1.93 (m, 2H) 1.78 (dd, J=8.53, 5.52 Hz, 1H) 1.56 (m, 5H) 1.25 (m, 11H) 1.07 (m, 6H). $^{19}$F NMR (400 MHz, CD$_3$OD): δ ppm −68.72 (s, 3F) −85.26 (s, 3F). MS: m/z 907.2 (M$^+$+1).

Compound 1042: 1,1,1-trifluoro-2-methylpropan-2-yl ((2R,6S,7R,9S,13aS,14aR,16aS,Z)-14a-((cyclopropylsulfonyl)carbamoyl)-2-((7-methoxy-3-(trifluoromethyl)quinoxalin-2-yl)oxy)-7-(methoxymethyl)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, CD$_3$OD): δ ppm 7.99 (d, J=9.04 Hz, 1H) 7.39 (m, 2H) 5.99 (br. s., 1H) 5.70 (br. s., 1H) 4.71 (t, J=8.28 Hz, 1H) 4.60 (m, 1H) 4.45 (d, J=6.02 Hz, 1H) 4.04 (m, 5H) 3.46 (m, 6H) 2.94 (br. s., 1H) 2.69 (m, 1H) 2.06 (m, 2H) 1.68 (m, 4H) 1.44 (d, J=9.54 Hz, 2H) 1.28 (m, 10H) 1.08 (m, 4H) 0.94 (d, J=7.03 Hz, 3H). MS: MS m/z 907.2 (M$^+$+1).

Preparation of Compound 1043

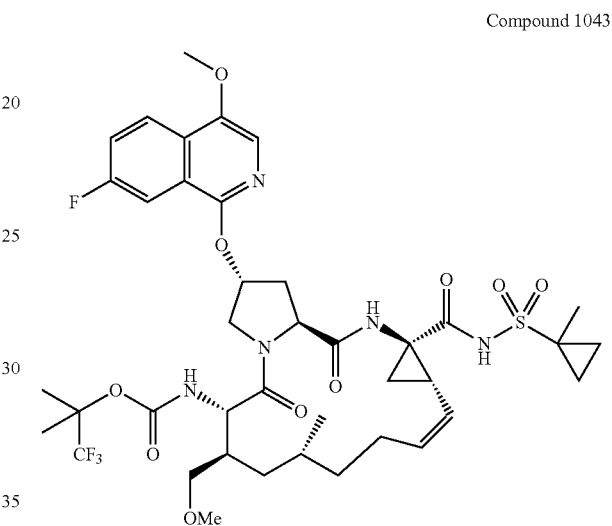

Compound 1043

Compound 1043 was prepared using the intermediates described herein and by following the general procedure described for the synthesis of Compound 1016.

Compound 1043: 1,1,1-trifluoro-2-methylpropan-2-yl ((2R,6S,7R,9R,13aS,14aR,16aS,Z)-2-((7-fluoro-4-methoxynaphthalen-1-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, CD$_3$OD): δ ppm 8.19 (dd, J=9.29, 5.27 Hz, 1H) 7.76 (m, 1H) 7.55 (m, 2H) 5.84 (br. s., 1H) 5.61 (br. s., 1H) 4.78 (m, 1H) 4.64 (m, 1H) 4.22 (m, 1H) 4.00 (m, 4H) 3.47 (m, 2H) 2.75 (m, 2H) 2.44 (m, 2H) 1.94 (d, J=8.03 Hz, 2H) 1.77 (m, 1H) 1.52 (m, 9H) 1.29 (m, 7H) 1.06 (s, 3H) 0.96 (m, 5H). MS: MS m/z 867.2 (M$^+$−1).

Scheme: Preparation of 1-Chloro-4-ethoxy-6-methoxyisoquinoline
Synthesis of 1-Chloro-ethoxy-6-methoxyisoquinoline:

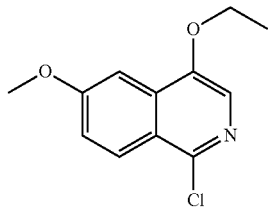

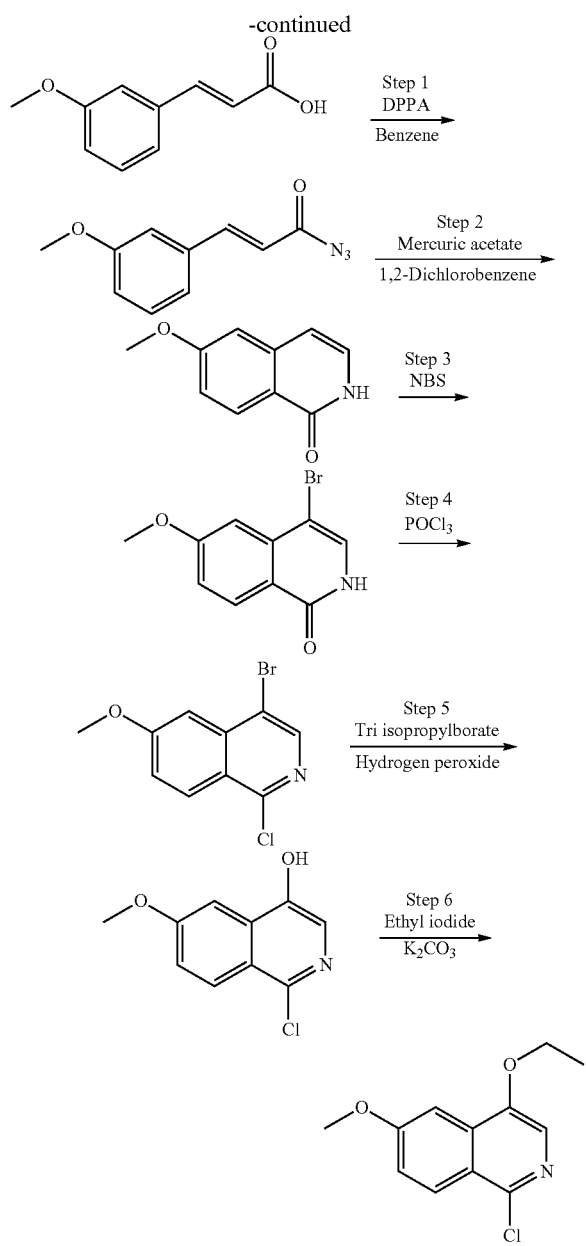

Step 1: Preparation of (E)-3-(3-methoxyphenyl)acryloyl azide

To a solution of (E)-3-(3-methoxyphenyl)acrylic acid (15 g, 84 mmol) in benzene (100 ml) was added triethylamine (11.73 ml, 84 mmol) followed by DPPA (23.17 g, 84 mmol) at room temperature. The reaction mass was stirred at the same temperature for 18 h. The solvent was evaporated under reduced pressure and the residue was diluted with water and extracted with dichloromethane. The organic layer was dried over anhydrous sodium sulfate, filtered and evaporated to get crude compound. The crude compound was purified by conventional column chromatography (Silica gel, 60-120 mesh) using 10% ethyl acetate in pet ether as mobile phase to get the desire compound as white solid (15 g, 88%). $^1$H NMR (400 MHz, CDCl$_3$): δ ppm 7.75-7.70 (d, J=20 Hz, 1H), 7.36-6.97 (m, 4H), 6.45-6.40 (d, J=20 Hz, 1H), 3.85 (s, 3H).

Step 2: Preparation of 6-methoxyisoquinolin-1(2H)-one

To a solution of (E)-3-(3-methoxyphenyl)acryloylazide (2.0 g, 9.84 mmol) in 1,2-dichlorobenzene (10 ml) was added mercuric acetate (0.031 g, 0.098 mmol). The reaction was heated at 120° C. and stirred for 5 minutes at this temperature and then it was heated to 180° C. for 1 h. The reaction mass was cooled to room temperature and diluted with pet ether. The precipitated solid was filtered washed with pet ether to get crude compound (1.2 g, 69.6%). The crude compound was taken to the next step without further purification. $^1$H NMR (400 MHz, DMSO-d$_6$): δ ppm 11.03 (s, 1H), 8.08-8.06 (d, J=8 Hz, 1H), 7.14-7.03 (m, 3H), 6.48-6.46 (d, J=8 Hz, 1H), 3.87 (s, 3H); MS: MS m/z 176.1 (M$^+$+1).

Step 3: Preparation of 4-bromo-6-methoxyisoquinolin-1(2H)-one

To a solution of 6-methoxyisoquinolin-1(2H)-one (2.5 g, 14.27 mmol) in acetonitrile (10 ml) was added NBS (2.54 g, 14.27 mmol) at room temperature under argon atmosphere. The reaction mass was stirred at the same temperature for 2 hr. The precipitated solid was filtered to get crude compound (2 g, 55.2%). The crude compound was taken to the next step without further purification. $^1$H NMR (400 MHz, DMSO-d$_6$): δ ppm 11.41 (s, 1H), 8.17-8.15 (d, J=8 Hz, 1H), 7.53 (s, 1H), 7.19-7.11 (m, 2H), 3.93 (s, 3H); MS: MS m/z 256.06 (M$^+$+2).

Step 4: Preparation of 4-bromo-1-chloro-6-methoxyisoquinoline

A solution of 4-bromo-6-methoxyisoquinolin-1(2H)-one (1.5 g, 5.90 mmol) in POCl$_3$ (15 ml) was refluxed for overnight. The solvent was evaporated under reduced pressure and the residue was diluted with cold water. The aqueous solution was basified by solid sodium carbonate and extracted with ethyl acetate. The combine organic layer was dried over anhydrous sodium sulfate, filtered and evaporated under reduced pressure to get crude compound. The crude compound was purified by silica gel chromatography (10% ethyl acetate in pet ether) to get desired compound (1.1 g, 65%) as white solid. $^1$H NMR (400 MHz, DMSO-d$_6$): δ ppm 8.53 (s, 1H), 8.27-8.24 (d, J=12 Hz, 1H), 7.56-7.53 (d, J=12 Hz, 1H), 7.41 (s, 1H), 4.02 (s, 3H); MS: MS m/z 273.99 (M$^+$+1).

Step 5: Preparation of 1-chloro-6-methoxyisoquinolin-4-ol

To a solution of 4-bromo-1-chloro-6-methoxyisoquinoline (0.25 g, 0.917 mmol) in THF (30 ml) was added n-butyllithium (1.147 ml, 1.835 mmol) at −78° C. under nitrogen. The reaction mixture was stirred for 30 minutes and triisopropyl borate (0.426 ml, 1.835 mmol) was added and stirred for another 30 minutes. To this hydrogen peroxide (0.273 ml, 8.90 mmol) (30% solution 1.5M) was added followed by the addition of sodium hydroxide (0.917 ml, 0.917 mmol). The resulting mixture was stirred for additional 1 h at room temperature. The reaction mixture was cooled to −40° C. and added sodium sulfite solution in water (1.156 g, 9.17 mmol). The resulting slurry was neutralized with 6N HCl solution and extracted with ethyl acetate. The combine organic layer was dried over anhydrous sodium sulfate, filtered and evaporated under reduced pressure to get crude compound. The crude compound was purified by silica gel chromatography (20% ethyl acetate in pet ether) to get desired compound (0.13 g, 67.6%) as solid. MS: MS m/z 210.06 (M$^+$+1).

Step 6: Preparation of 1-chloro-4-ethoxy-6-methoxyisoquinoline

To a solution of 1-chloro-6-methoxyisoquinolin-4-ol (0.05 g, 0.239 mmol) in acetonitrile (5 ml) was added potassium carbonate (0.099 g, 0.716 mmol) followed by iodoethane (0.039 ml, 0.477 mmol) at room temperature. The reaction mass was stirred at the same temperature for 18 h. The solvent was evaporated under reduced pressure and the residue was diluted with water and extracted with dichloromethane. The organic layer was dried over anhydrous sodium sulfate, filtered and evaporated to get crude compound. The crude compound was purified by silica gel chromatography (10% ethyl acetate in pet ether) to get desired compound (0.015 g, 25.1%) as solid. $^1$H NMR (400 MHz, DMSO-d$_6$): δ ppm 8.14-8.12 (d, J=8 Hz, 1H), 7.90 (s, 1H), 7.46-7.42 (m, 2H), 4.34-4.27 (q, J=8 Hz, 2H), 3.95 (s, 3H), 1.48 (t, J=10 Hz, 3H).

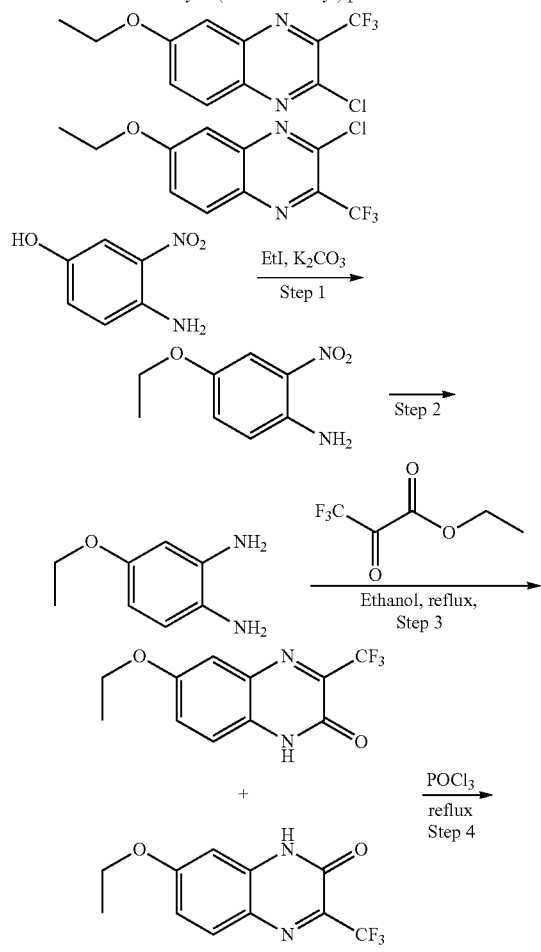

Scheme: Preparation of 2-chloro-6-ethoxy-3-(trifluoromethyl)quinoxaline and 3-chloro-6-ethoxy-2-(trifluoromethyl)quinoxaline
2-chloro-6-ethoxy-3-(trifluoromethyl)quinoxaline &
3-chloro-6-ethoxy-2-(trifluoromethyl)quinoxaline

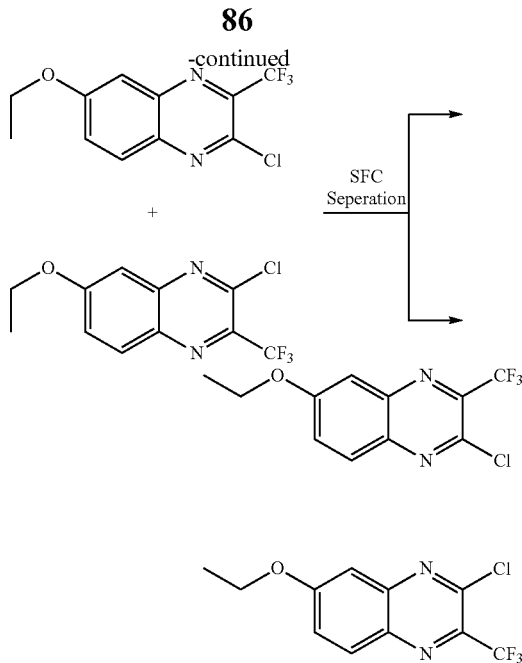

Step 1: Preparation of 4-ethoxy-2-nitroaniline

To a solution of 4-amino-3-nitrophenol (5.0 g, 32.4 mmol) in acetonitrile (100 mL) was added K$_2$CO$_3$ (13.45 g, 97 mmol) followed by ethyl iodide (13.11 mL, 162 mmol) at room temperature. The reaction mixture was stirred at room temperature for overnight. The reaction mixture was filtered through celite bed and washed with acetonitrile. The filtrate was evaporated under reduced pressure to get crude compound. The crude compound was purified by ISCO using 10-30% ethyl acetate in hexane as mobile phase to get 4-ethoxy-2-nitroaniline (3.0 g, 16.47 mmol, 50.8% yield) as red color solid. $^1$H NMR (400 MHz, DMSO-d$_6$): δ ppm 7.35-7.34 (d, J=4 Hz, 1H), 7.23 (s, 2H), 7.16-7.13 (dd, J=9.2 Hz, 3.2 Hz, 1H), 7.00-6.97 (d, J=90.6 Hz, 1H), 3.99-3.94 (q, J=6.8 Hz, 6H), 1.31-1.28 (t, J=6.8 Hz, 3H). MS: MS m/z 181.2 (M$^+$−1).

Step 2: Preparation of 4-ethoxybenzene-1,2-diamine

The same procedure was followed as described for 4-fluoro-5-methoxybenzene-1,2-diamine but 4-ethoxy-2-nitroaniline used as starting materials instead of 4-fluoro-5-methoxy-2-nitroaniline. $^1$H NMR (400 MHz, DMSO-d$_6$): δ ppm 6.40-6.38 (d, J=8 Hz, 1H), 6.15-6.14 (d, J=3.6 Hz, 1H), 5.97-5.93 (dd, J=11.2 Hz, 3.6 Hz, 1H), 4.45 (bs, 2H), 3.975-3.970 (bs, 2H), 3.84-3.77 (q, J=9.2 Hz, 2H), 1.29-1.21 (t, J=16.4 Hz, 3H).

Step 3: Preparation of 6-ethoxy-3-(trifluoromethyl)quinoxalin-2(1H)-one and 7-ethoxy-3-(trifluoromethyl)quinoxalin-2(1H)-one The same procedure was followed as described for 7-fluoro-6-methoxy-3-(trifluoromethyl)quinoxalin-2(1H)-one but 4-ethoxybenzene-1,2-diamine was used as starting material instead of 4-fluoro-5-methoxybenzene-1,2-diamine. $^1$H NMR (400 MHz, DMSO-d6): δ ppm 12.92 (br, s, 2H), 7.84-7.81 (d, J=12 Hz, 1H), 7.44-7.33 (m, 4H), 7.82 (s, 1H), 3.87 (s, 6H), MS: MS m/z 245.15 (M$^+$+1).

Step 4: Preparation of 2-chloro-6-ethoxy-3-(trifluoromethyl)quinoxaline and 3-chloro-6-ethoxy-2-(trifluoromethyl)quinoxaline The same procedure was followed as described for 2-chloro-7-fluoro-6-methoxy-3-(trifluoromethyl)quinoxaline but 6-ethoxy-3-(trifluoromethyl)quinoxalin-2(1H)-one and 7-ethoxy-3-(trifluoromethyl)quinoxalin-2(1H)-one was used as starting material instead of 2-chloro-7-fluoro-6-methoxy-3-(trifluoromethyl)quinoxaline and 2-chloro-6-fluoro-7-methoxy-3-(trifluoromethyl)quinoxaline.

2-chloro-6-ethoxy-3-(trifluoromethyl)quinoxaline: $^1$H NMR (400 MHz, DMSO-d6): δ ppm 8.10-8.07 (d, J=12 Hz, 1H), 7.75-7.44 (m, 2H), 3.95 (s, 3H); $^{19}$F NMR: δ ppm −65.36 (1F) MS: MS m/z 263.10 (M$^+$+1).

3-chloro-6-ethoxy-2-(trifluoromethyl)quinoxaline: $^1$H NMR (400 MHz, DMSO-d6): δ ppm 8.11-8.08 (d, J=12 Hz, 1H), 7.78-7.75 (d, J=12 Hz, 1H), 7.68 (s, 1H), 4.00 (s, 3H). $^{19}$F NMR: δ ppm −65.36 (1F) MS: MS m/z 263.09 (M$^+$+1).

Scheme: Preparation of 2-chloro-6-isopropoxy-3-(trifluoromethyl)quinoxaline & 3-chloro-6-isopropyl-2-(trifluoromethyl)quinoxaline 2-chloro-6-isopropoxy-3-(trifluoromethyl)quinoxaline & 3-chloro-6-isopropoxy-2-(trifluoromethyl)quinoxaline

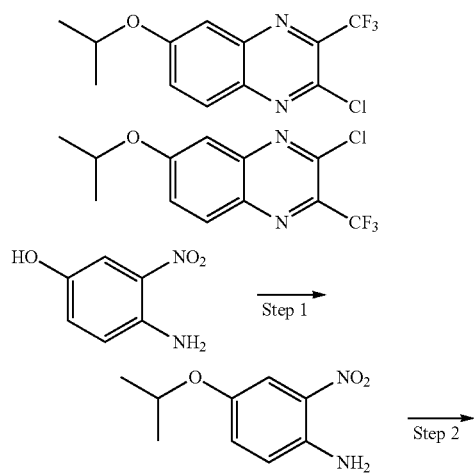

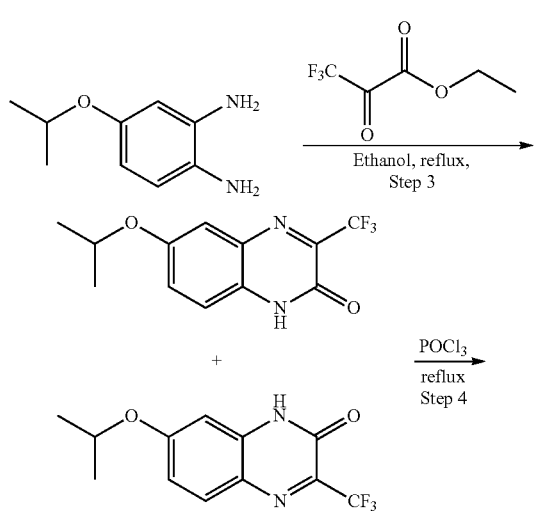

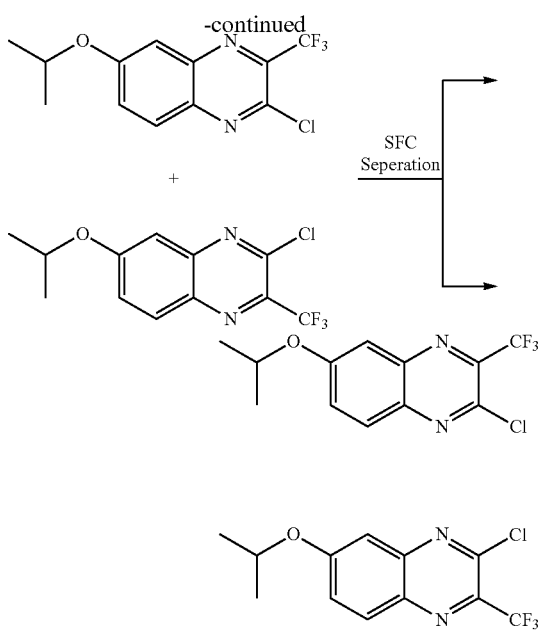

Step 1: Preparation of 4-isopropoxy-2-nitroaniline

To a solution of 4-amino-3-nitrophenol (5 g, 32.4 mmol) in DMF (30 mL) was added cesium carbonate (21.14 g, 64.9 mmol) and 2-bromopropane (3.05 mL, 32.4 mmol) at room temperature. The reaction mass was heated at 80° C. for 3 h. Solvent was removed under educed pressure and the residue was diluted with ethyl acetate. The organic solution was washed with water, dried over anhydrous sodium sulphate and concentrated to get the crude compound. The crude compound was purified using flash column chromatography and the product was eluted with 30% ethyl acetate in pet-ether to afford 4-isopropoxy-2-nitroaniline (6 g, 26.9 mmol, 83% yield) as a brown crystalline solid. $^1$H NMR (400 MHz, DMSO-d$_6$): δ ppm 7.37 (d, J=2.51 Hz, 1H) 7.21 (s, 2H) 7.14 (dd, J=9.29, 2.76 Hz, 1H) 6.99 (d, J=9.04 Hz, 1H) 4.38-4.52 (m, 1H) 1.13-1.31 (m, 6H) MS: MS m/z 197.15 (M$^+$+1).

Step 2: Preparation of 4-isopropoxybenzene-1,2-diamine

The same procedure was followed as described for 4-fluoro-5-methoxybenzene-1,2-diamine but 4-isopropoxy-2-nitroaniline was used as starting materials instead of 4-fluoro-5-methoxy-2-nitroaniline. $^1$H NMR (400 MHz, DMSO-d$_6$): δ ppm 6.39 (d, J=8.31 Hz, 1H) 6.15 (d, J=3.02 Hz, 1H) 5.96 (dd, J=8.31, 2.64 Hz, 1H) 4.36 (bs, 2H) 4.19-4.32 (m, 1H) 3.9 (bs, 2H) 1.17 (d, J=6.04 Hz, 6H) MS: MS m/z 167.1 (M$^+$+1).

Step 3: Preparation of 6-isopropoxy-3-(trifluoromethyl)quinoxalin-2(1H)-one and 7-isopropoxy-3-(trifluoromethyl)quinoxalin-2(1H)-one The same procedure was followed as described for 7-fluoro-6-methoxy-3-(trifluoromethyl)quinoxalin-2(1H)-one but 4-isopropoxybenzene-1,2-diamine was used as starting material instead of 4-fluoro-5-methoxybenzene-1,2-diamine. $^1$H NMR (400 MHz, DMSO-d6): δ ppm 12.98 (s, 1H) 7.40-7.31 (m, 3H) 4.73 (m, 1H) 4.19-4.32 (m, 1H) 1.28 (m, 6H) $^{19}$F NMR: δ ppm −67.86 (3F) MS: MS m/z 273.1 (M$^+$+1).

Step 4: Preparation of 2-chloro-7-isopropoxy-3-(trifluoromethyl)quinoxaline

The same procedure was followed as described for 2-chloro-7-fluoro-6-methoxy-3-(trifluoromethyl)quinoxaline but 6-isopropoxy-3-(trifluoromethyl)quinoxalin-2(1H)-one and 7-isopropoxy-3-(trifluoromethyl)quinoxalin-2(1H)-one was used as starting material instead of 2-chloro-7-fluoro-6-methoxy-3-(trifluoromethyl)quinoxaline and 2-chloro-6-fluoro-7-methoxy-3-(trifluoromethyl)quinoxaline. $^1$H NMR (400 MHz, DMSO-d6): δ ppm 8.04-8.20 (m, 1H) 7.55-7.75 (m, 2H) 4.92-5.05 (m, 1H) 1.33-1.43 (m, 6H) $^{19}$F NMR: δ ppm −66.10 (3F) MS: MS m/z 291.5 (M$^+$+1). Structure was confirmed by single crystal X-ray studies.

Scheme: Preparation of 2-chloro-4,5-dimethoxyquinazoline
2-chloro-4,5-dimethoxyquinazoline

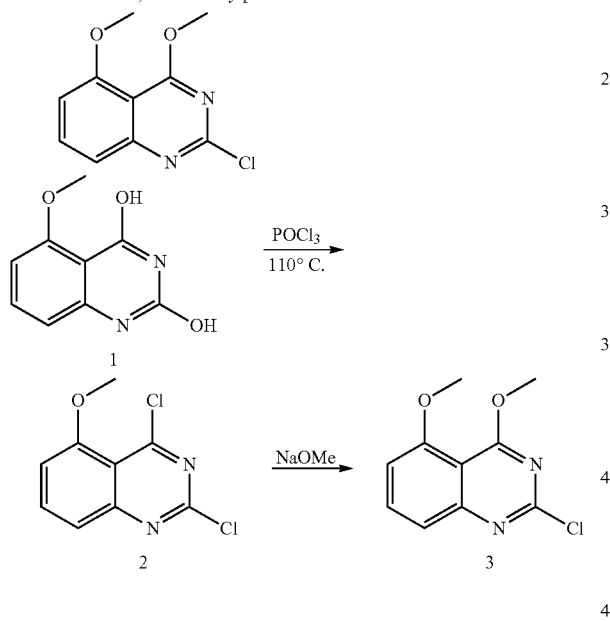

Step 1: 2,4-dichloro-5-methoxyquinazoline

To the stirred solution of 5-methoxyquinazoline-2,4-diol (1.1 g, 5.72 mmol) in was added POCl$_3$ (5.34 ml, 57.2 mmol) at room temperature, then the reaction mixture was stirred at 110° C. for overnight. After completion of the reaction, reaction mixture was quenched with ice water (100 mL), extracted with DCM (2×150 mL), then the combined organic layer was washed with 10% sodium bicarbonate solution (100 mL, brine solution, dried over sodium sulphate and concentrated to get residue. The crude compound was purified by ISCO (Silica gel) using 7% ethyl acetate in hexane as mobile phase to get 2,4-dichloro-5-methoxyquinazoline (0.8 g, 3.49 mmol, 61.0% yield). MS: MS m/z 229.0 (M$^+$+1), $^1$H NMR (400 MHz, CHLOROFORM-d) δ ppm 7.86 (t, J=8.28 Hz, 1H) 7.44-7.64 (m, 1H) 7.02 (dd, J=8.13, 0.53 Hz, 1H) 3.84-4.28 (m, 3H).

Step 2: 2-chloro-4,5-dimethoxyquinazoline

To a stirred solution of 2,4-dichloro-5-methoxyquinazoline (250 mg, 1.091 mmol) in MeOH (5 mL) was added SODIUM METHOXIDE (64.9 mg, 1.201 mmol) at room temperature, then the reaction mixture was stirred at room temperature and stirred for 24 hours. After completion of the reaction mixture was concentrated under vacuum to get crude residue, then the residue was quenched with 1.5 N HCl (pH=6-7) and extracted with ethyl acetate (2×25 mL), then the combined organic layer was washed with brine solution, dried over sodium sulphate and concentrated under vacuum to get crude compound. The crude compound was purified by ISCO (Silica gel) using 5% ethyl acetate in hexane as mobile phase to get 2-chloro-4,5-dimethoxyquinazoline (150 mg, 0.668 mmol, 61.2% yield). MS: MS m/z 225.0 (M$^+$+1), $^1$H NMR (300 MHz, CHLOROFORM-d) δ ppm 7.74 (t, J=8.26 Hz, 1H) 7.46 (dd, J=8.36, 0.94 Hz, 1H) 6.94 (dd, J=8.10, 0.59 Hz, 1H) 4.21 (s, 3H) 4.01 (s, 3H).

Scheme: Preparation of 2-chloro-7-fluoro-6-methoxy-3-(trifluoromethyl)quinoxaline and 2-chloro-6-fluoro-7-methoxy-3-(trifluoromethyl)quinoxaline
2-chloro-7-fluoro-6-methoxy-3-(trifluoromethyl)quinoxaline & 2-chloro-6-fluoro-7-methoxy-3-(trifluoromethyl)quinoxaline

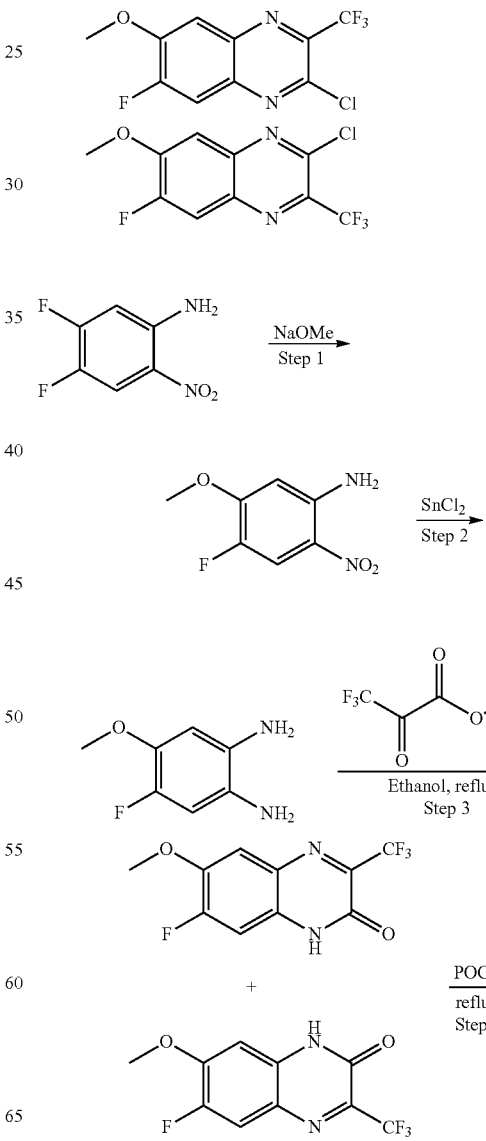

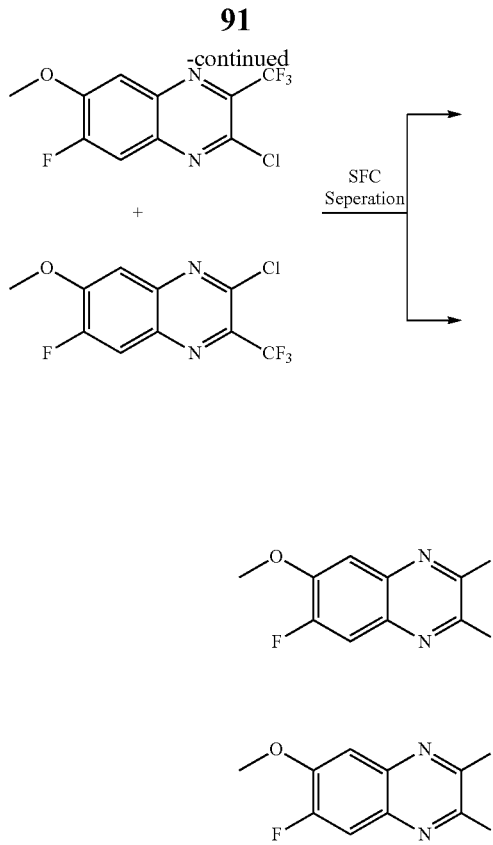

Step 1: Preparation of 4-fluoro-5-methoxy-2-nitroaniline

To an ice cooled 100 ml round bottom flask charged with methanol (30 mL) was added sodium methoxide (1.551 g, 28.7 mmol). After the solution was homogeneous, 4,5-difluoro-2-nitroaniline (2 g, 11.49 mmol) was added portion wise. The solution turns a bright yellow and slowly yellow precipitation was observed. Solvent was removed under reduced pressure and the residue was diluted with water and acidified using 1.5N HCl solution. The aqueous layer was extracted with ethyl acetate twice, the combined organic layer was washed with water, brine solution, dried over anhydrous sodium sulphate and concentrated to dryness to get 4-fluoro-5-methoxy-2-nitroaniline (1.8 g, 9.48 mmol, 82% yield) as pale yellow solid. $^1$H NMR (400 MHz, CDCl$_3$): δ ppm 7.76 (d, J=12.55 Hz, 1H) 7.54 (br. s., 2H) 6.65 (s, 1H) 3.86 (s, 3H). $^{19}$F NMR: δ ppm −147.64 (1F); MS: MS m/z 185.2 (M$^+$−1)

Step 2: Preparation of 4-fluoro-5-methoxybenzene-1,2-diamine

To the Suspension of tin(II) chloride di-hydrate (6.55 g, 29.0 mmol) in water (40 mL) was added con. HCl (8 mL) slowly and the resulting solution was stirred for 10 min. 5-fluoro-4-methoxy-2-nitroaniline (1.8 g, 9.67 mmol) was added portion wise to the reaction mass and heated to 70° C. overnight. The reaction was allowed to cool to room temperature and was made alkaline by drop wise addition of 10% NaOH solution (pH=10-11). The aqueous reaction mass was extracted with ethyl acetate. The combined organic layer was washed with water, brine Solution, dried over anhydrous sodium sulphate and concentrated to get crude 4-fluoro-5-methoxybenzene-1,2-diamine (1.2 g, 7.68 mmol, 79% yield) as brown solid. The crude compound was taken to the next step without further purification. $^1$H NMR (400 MHz, DMSO-d$_6$): δ ppm 6.32-6.43 (m, 2H) 4.32 (br. s., 4H) 3.65 (s, 3H); $^{19}$F NMR: δ ppm −149.03 (1F); MS: MS m/z 157.3 (M$^+$+1).

Step 3: Preparation of 7-fluoro-6-methoxy-3-(trifluoromethyl)quinoxalin-2(1H)-one and 6-fluoro-7-methoxy-3-(trifluoromethyl)quinoxalin-2(1H)-one To a solution of 4-fluoro-5-methoxybenzene-1,2-diamine (13 g, 83 mmol) in ethanol (100 mL) was added ethyl 3,3,3-trifluoro-2-oxopropanoate (13.15 mL, 108 mmol) at room temperature. The reaction mass was heated at reflux for 18 h. The solvent was evaporated under reduced pressure and the residue was washed with diethyl ether to get crude compound 7-fluoro-6-methoxy-3-(trifluoromethyl)quinoxalin-2-ol (15 g, 49.2 mmol, 59.1% yield) as mixture of regioisomer. The crude compound was taken directly to the next step without separation of isomers. MS: MS m/z 263.1 (M$^+$+1).

Step 4: Preparation of 2-chloro-7-fluoro-6-methoxy-3-(trifluoromethyl)quinoxaline and 2-chloro-6-fluoro-7-methoxy-3-(trifluoromethyl)quinoxaline A solution of 7-fluoro-6-methoxy-3-(trifluoromethyl)quinoxalin-2-ol (12 g, 45.8 mmol) in POCl$_3$ (100 mL) was heated at reflux for 3 h. Excess POCl$_3$ was removed under reduced pressure and the residue was diluted with cold water and basified by using 10% NaOH Solution (pH=~10). The aqueous reaction mass was extracted with ethyl acetate. The combined organic layer was washed with water, brine Solution, dried over anhydrous sodium sulphate and concentrated to get crude compound as mixture of regioisomer. The mixture of regioisomer was separated by SFC to get 2-chloro-7-fluoro-6-methoxy-3-(trifluoromethyl)quinoxaline (3.5 g, 12.22 mmol, 26.7% yield) and 2-chloro-6-fluoro-7-methoxy-3-(trifluoromethyl)quinoxaline (5 g, 17.46 mmol, 38.1% yield).

2-chloro-6-fluoro-7-methoxy-3-(trifluoromethyl)quinoxaline: $^1$H NMR (400 MHz, CDCl$_3$): δ ppm 7.83-7.81 (d, J=10.4 Hz, 1H) 7.46-7.44 (d, J=8 Hz, 1H), 4.09 (s, 3H). $^{19}$F NMR: δ ppm −66.32 (3F), −122.46 (1F). The structure was confirmed by single crystal x-ray studies.

2-chloro-7-fluoro-6-methoxy-3-(trifluoromethyl)quinoxaline: $^1$H NMR (400 MHz, CDCl$_3$): δ ppm 7.73-7.71 (d, J=10.8 Hz, 1H) 7.58-7.56 (d, J=8.4 Hz, 1H), 4.08 (s, 3H). $^{19}$F NMR: δ ppm −66.58 (3F), −119.04 (1F).

Preparation of Compound 1045 and Compound 1047

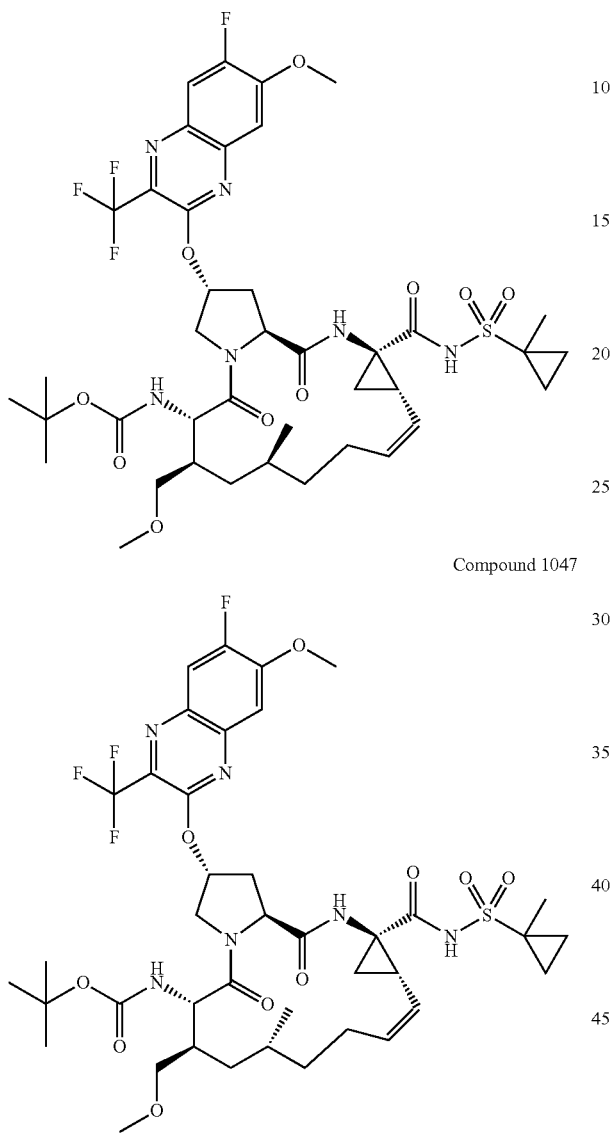

Compound 1045

Compound 1047

Compound 1045 and compound 1047 were prepared using the intermediates described herein and by following the general procedure described for the synthesis of Compound 1010.

Compound 1045: tert-butyl ((2R,6S,7R,9S,13aS,14aR,16aS,Z)-2-((6-fluoro-7-methoxy-3-(trifluoromethyl)quinoxalin-2-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, METHANOL-d$_4$) δ ppm 7.77 (d, J=11.04 Hz, 1H) 7.58 (d, J=8.53 Hz, 1H) 6.01 (br. s., 1H) 5.73 (m, J=10.04 Hz, 1H) 5.06 (m, 1H) 4.71 (t, J=8.03 Hz, 1H) 4.44-4.63 (m, 3H) 4.12 (s, 4H) 3.42-3.49 (m, 2H) 2.51-2.72 (m, 3H) 2.38-2.50 (m, 1H) 2.05-2.17 (m, 1H) 1.93-2.05 (m, 1H) 1.69-1.76 (m, 1H) 1.55-1.69 (m, 3H) 1.52 (s, 3H) 1.38-1.49 (m, 3H) 1.24-1.37 (m, 3H) 1.15-1.23 (m, 8H) 0.94 (d, J=7.03 Hz, 6H). MS: MS m/z 885.3 (M$^+$+1).

Compound 1047: tert-butyl ((2R,6S,7R,9R,13aS,14aR,16aS,Z)-2-((6-fluoro-7-methoxy-3-(trifluoromethyl)quinoxalin-2-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, METHANOL-d$_4$) δ ppm 7.77 (d, J=11.04 Hz, 1H) 7.58 (d, J=8.53 Hz, 1H) 6.01 (br. s., 1H) 5.73 (m, J=10.04 Hz, 1H) 5.06 (m, 1H) 4.71 (t, J=8.03 Hz, 1H) 4.44-4.63 (m, 3H) 4.12 (s, 4H) 3.42-3.49 (m, 2H) 2.51-2.72 (m, 3H) 2.38-2.50 (m, 1H) 2.05-2.17 (m, 1H) 1.93-2.05 (m, 1H) 1.69-1.76 (m, 1H) 1.55-1.69 (m, 3H) 1.52 (s, 3H) 1.38-1.49 (m, 3H) 1.24-1.37 (m, 3H) 1.15-1.23 (m, 8H) 0.94 (d, J=7.03 Hz, 6H). MS: MS m/z 885.4 (M$^+$+1).

Preparation of Compound 1046 and Compound 1048

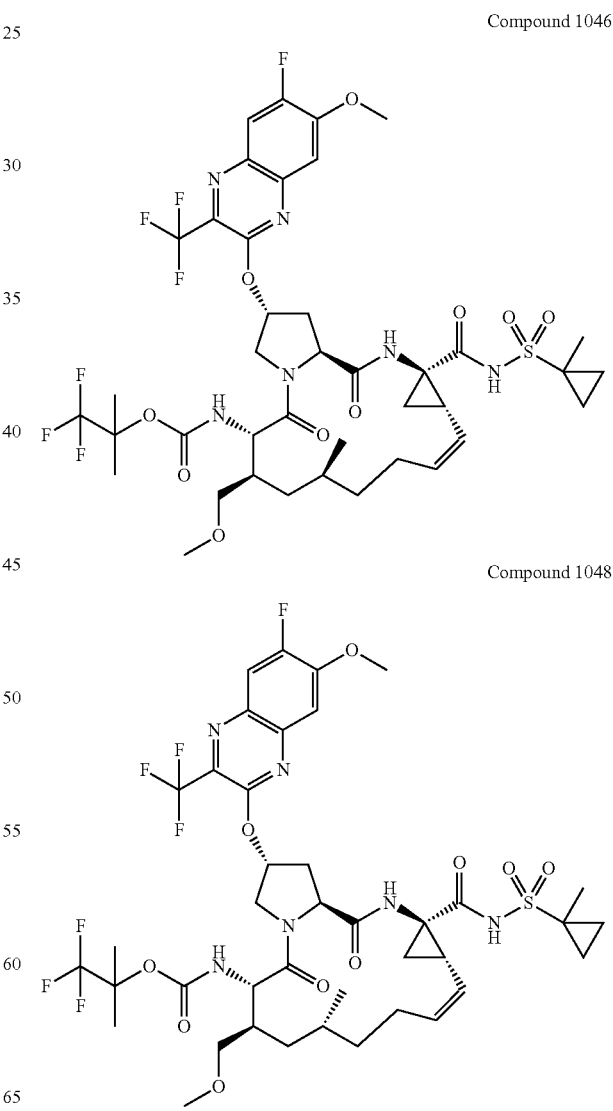

Compound 1046

Compound 1048

Compound 1046 and Compound 1048 were prepared using the intermediates described herein and by following the general procedure described for the synthesis of Compound 1016.

Compound 1046: 1,1,1-trifluoro-2-methylpropan-2-yl ((2R,6S,7R,9S,13aS,14aR,16aS,Z)-2-((6-fluoro-7-methoxy-3-(trifluoromethyl)quinoxalin-2-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, METHANOL-d$_4$) δ ppm 7.80 (s, 1H) 7.59 (s, 1H) 6.00 (br. s., 1H) 5.71 (m., 1H) 5.06 (t, 2H) 4.96 (s, 1H) 4.67-4.78 (m, 2H) 4.51-4.62 (m, 2H) 4.46 (d, J=6.02 Hz, 1H) 4.04-4.16 (m, 4H) 3.41-3.49 (m, 2H) 2.68 (t, J=7.28 Hz, 2H) 2.54 (m, 1H) 2.36-2.49 (m, 1H) 2.00 (m, 2H) 1.71 (d, J=8.03 Hz, 1H) 1.61 (m, 1H) 1.52 (s, 4H) 1.39-1.50 (m, 4H) 1.15-1.38 (m, 7H) 0.81-0.98 (m, 6H). MS: MS m/z 939.4 (M$^+$+1).

Compound 1048: 1,1,1-trifluoro-2-methylpropan-2-yl ((2R,6S,7R,9R,13aS,14aR,16aS,Z)-2-((6-fluoro-7-methoxy-3-(trifluoromethyl)quinoxalin-2-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, METHANOL-d$_4$) δ ppm 7.81 (s, 1H) 7.58 (s, 1H) 5.97 (br. s., 1H) 5.63 (td, J=10.16, 5.77 Hz, 1H) 5.02 (t, J=10.04 Hz, 2H) 4.56-4.71 (m, 2H) 4.12 (d, J=10.54 Hz, 5H) 4.04 (dd, J=12.05, 3.51 Hz, 1H) 3.44 (dd, J=7.53, 2.51 Hz, 2H) 2.63-2.79 (m, 2H) 2.33-2.58 (m, 2H) 1.86-2.02 (m, 2H) 1.77 (s, 1H) 1.64-1.71 (m, 1H) 1.36-1.62 (m, 8H) 1.14-1.34 (m, 8H) 1.00 (d, J=6.53 Hz, 3H) 0.90 (s, 3H). MS: MS m/z 839.4 (M$^+$+1).

Preparation of Compound 1049 and Compound 1050

Compound 1049

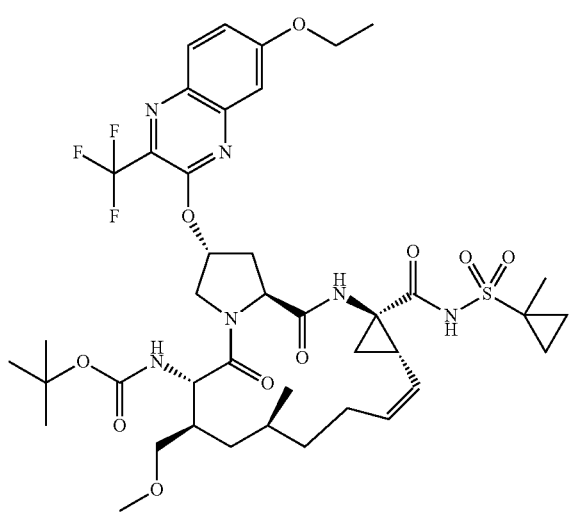

Compound 1050

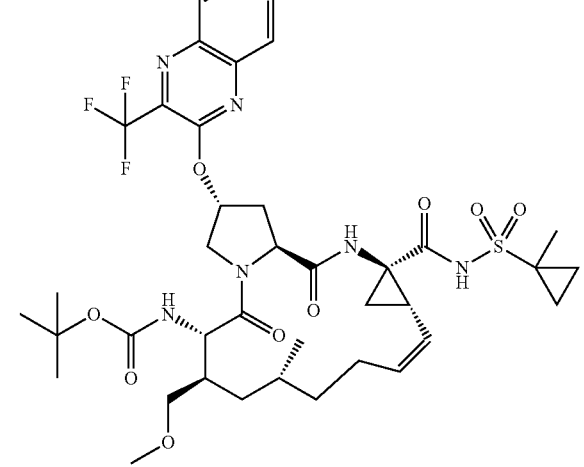

Compound 1049 and Compound 1050 were prepared using the intermediates described herein and by following the general procedure described for the synthesis of Compound 1010.

Compound 1049: tert-butyl ((2R,6S,7R,9S,13aS,14aR,16aS,Z)-2-((7-ethoxy-3-(trifluoromethyl)quinoxalin-2-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, METHANOL-d$_4$) δ ppm 7.97 (d, J=9.04 Hz, 1H) 7.29-7.43 (m, 2H) 6.03 (br. s., 1H) 5.73 (m, J=9.54 Hz, 1H) 5.07 (m, 1H) 4.71 (t, J=8.28 Hz, 2H) 4.47-4.63 (m, 3H) 4.28 (qd, J=7.03, 1.51 Hz, 3H) 4.06-4.18 (m, 1H) 3.47 (br. s., 3H) 2.50-2.71 (m, 4H) 2.38-2.49 (m, 1H) 2.06-2.17 (m, 1H) 1.92-2.05 (m, 1H) 1.69-1.76 (m, 1H) 1.56-1.68 (m, 1H) 1.37-1.55 (m, 9H) 1.29 (s, 3H) 1.10-1.23 (m, 9H) 0.83-0.98 (m, 5H). MS: MS m/z 880.4 (M$^+$+1).

Compound 1050: tert-butyl ((2R,6S,7R,9R,13aS,14aR,16aS,Z)-2-((7-ethoxy-3-(trifluoromethyl)quinoxalin-2-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, METHANOL-d$_4$) δ ppm 7.97 (d, J=9.04 Hz, 1H) 7.29-7.43 (m, 2H) 6.03 (br. s., 1H) 5.73 (m, J=9.54 Hz, 1H) 5.07 (m, 1H) 4.71 (t, J=8.28 Hz, 2H) 4.47-4.63 (m, 3H) 4.28 (qd, J=7.03, 1.51 Hz, 3H) 4.06-4.18 (m, 1H) 3.47 (br. s., 3H) 2.50-2.71 (m, 4H) 2.38-2.49 (m, 1H) 2.06-2.17 (m, 1H) 1.92-2.05 (m, 1H) 1.69-1.76 (m, 1H) 1.56-1.68 (m, 1H) 1.37-1.55 (m, 9H) 1.29 (s, 3H) 1.10-1.23 (m, 9H) 0.83-0.98 (m, 5H). MS: MS m/z 880.5 (M$^+$+1).

Preparation of Compound 1051 and Compound 1052

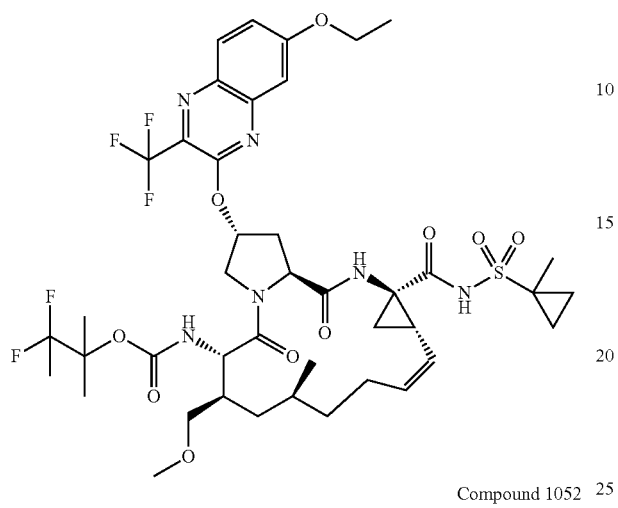

Compound 1051

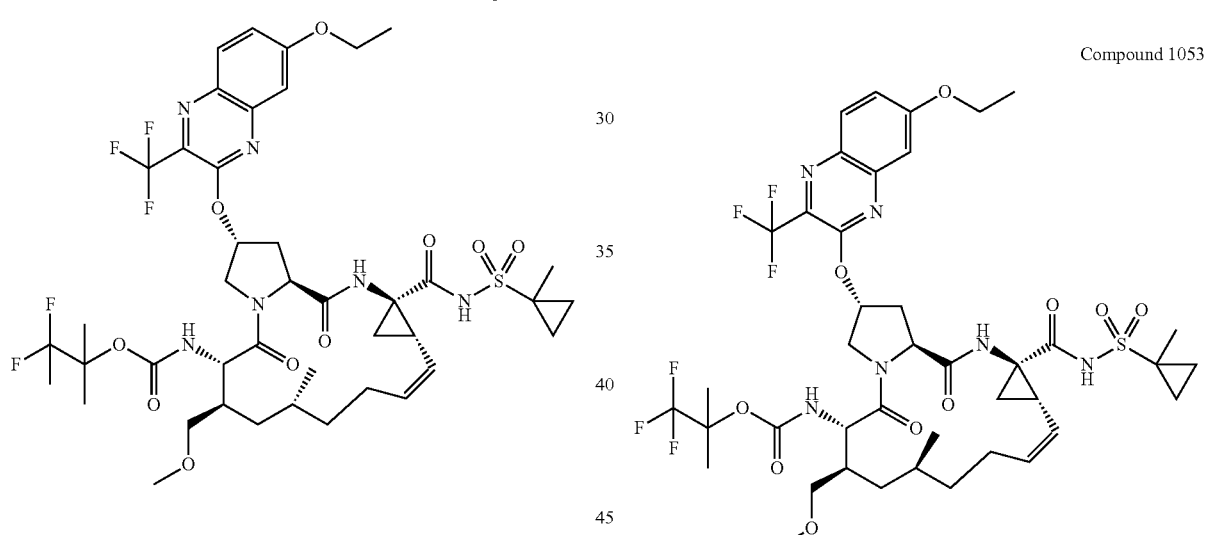

Compound 1052

Compound 1051 and Compound 1052 were prepared using the intermediates described herein and by following the general procedure described for the synthesis of Compound 1016 using 3,3-difluoro-2-methylbutan-2-ylpyridin-2-yl carbonate instead of pyridin-2-yl (1,1,1-trifluoro-2-methylpropan-2-yl) carbonate.

Compound 1051: 3,3-difluoro-2-methylbutan-2-yl ((2R,6S,7R,9S,13aS,14aR,16aS,Z)-2-((7-ethoxy-3-(trifluoromethyl)quinoxalin-2-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, METHANOL-$d_4$) δ ppm 7.92-8.04 (m, 1H) 7.38 (dq, J=5.02, 2.51 Hz, 2H) 7.02 (d, J=8.03 Hz, 1H) 5.98 (br. s., 1H) 5.63 (td, J=10.29, 5.52 Hz, 1H) 5.02 (t, J=9.79 Hz, 1H) 4.66 (dd, J=10.29, 7.28 Hz, 1H) 4.29 (m, J=10.35, 6.75, 6.75, 3.26 Hz, 2H) 4.15 (d, J=3.01 Hz, 1H) 4.05 (dd, J=11.80, 3.26 Hz, 1H) 3.39-3.48 (m, 2H) 2.71 (d, J=8.53 Hz, 2H) 2.37-2.55 (m, 2H) 1.94 (d, J=12.55 Hz, 2H) 1.77 (m, J=8.03, 5.52 Hz, 1H) 1.67 (d, J=10.54 Hz, 1H) 1.37-1.62 (m, 13H) 1.19-1.35 (m, 3H) 1.10 (d, J=9.54 Hz, 5H) 1.00 (d, J=6.53 Hz, 3H) 0.84-0.94 (m, 2H) MS: MS m/z 931.4 (M$^+$+1).

Compound 1052: 3,3-difluoro-2-methylbutan-2-yl ((2R,6S,7R,9R,13aS,14aR,16aS,Z)-2-((7-ethoxy-3-(trifluoromethyl)quinoxalin-2-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, METHANOL-$d_4$) δ ppm 7.91-8.05 (m, 1H) 7.38 (dq, J=5.02, 2.51 Hz, 2H) 7.02 (d, J=8.03 Hz, 1H) 5.98 (br. s., 1H) 5.63 (td, J=10.29, 5.52 Hz, 1H) 5.02 (t, J=9.79 Hz, 1H) 4.66 (dd, J=10.29, 7.28 Hz, 1H) 4.22-4.35 (m, 2H) 4.15 (d, J=3.01 Hz, 1H) 4.05 (dd, J=11.80, 3.26 Hz, 1H) 3.40-3.48 (m, 2H) 2.71 (d, J=8.53 Hz, 2H) 2.36-2.55 (m, 2H) 1.94 (d, J=12.55 Hz, 2H) 1.77 (m, J=8.03, 5.52 Hz, 1H) 1.67 (d, J=10.54 Hz, 1H) 1.40-1.62 (m, 13H) 1.18-1.34 (m, 3H) 1.10 (d, J=9.54 Hz, 5H) 1.00 (d, J=6.53 Hz, 3H) 0.83-0.94 (m, 2H). MS: MS m/z 931.4 (M$^+$+1).

Preparation of Compound 1053 and Compound 1054

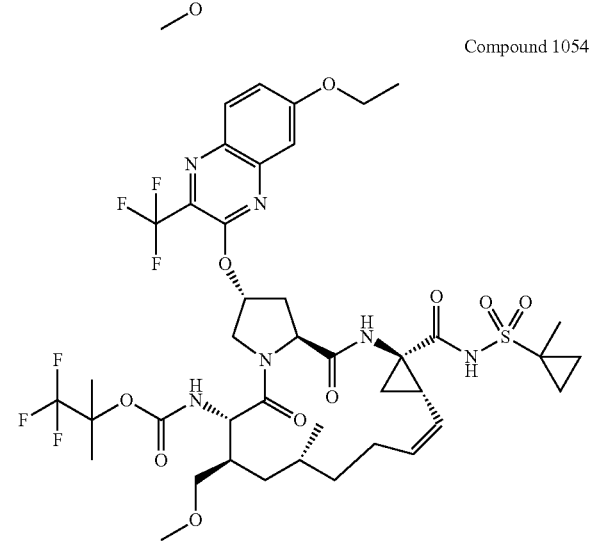

Compound 1053

Compound 1054

Compound 1053 and Compound 1054 were prepared using the intermediates described herein and by following the general procedure described for the synthesis of Compound 1016.

Compound 1053: 1,1,1-trifluoro-2-methylpropan-2-yl ((2R,6S,7R,9S,13aS,14aR,16aS,Z)-2-((7-ethoxy-3-(trifluoromethyl)quinoxalin-2-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, METHANOL-d$_4$) δ ppm 7.95-8.02 (m, 1H) 7.34-7.43 (m, 2H) 7.20-7.28 (m, 1H) 5.99 (d, J=12.55 Hz, 1H) 5.73 (d, J=8.53 Hz, 1H) 5.63 (td, J=10.16, 5.77 Hz, 1H) 4.98-5.09 (m, 1H) 4.70-4.77 (m, 1H) 4.66 (dd, J=10.04, 7.03 Hz, 1H) 4.58 (d, J=12.05 Hz, 1H) 4.46 (d, J=6.53 Hz, 1H) 4.21-4.36 (m, 2H) 4.12 (br. s., 2H) 3.42-3.49 (m, 2H) 2.70 (d, J=9.54 Hz, 2H) 2.38-2.63 (m, 3H) 2.07-2.17 (m, 1H) 1.85-2.05 (m, 2H) 1.77 (dd, J=8.28, 5.77 Hz, 1H) 1.64-1.73 (m, 2H) 1.59 (dd, J=9.54, 5.52 Hz, 2H) 1.39-1.55 (m, 7H) 1.15-1.38 (m, 7H) 0.84-1.05 (m, 5H). MS: MS m/z 835.3 (M$^+$+41).

Compound 1054: 1,1,1-trifluoro-2-methylpropan-2-yl ((2R,6S,7R,9R,13aS,14aR,16aS,Z)-2-((7-ethoxy-3-(trifluoromethyl)quinoxalin-2-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, METHANOL-d$_4$) δ ppm 7.94-8.01 (m, 1H) 7.33-7.44 (m, 2H) 5.98 (br. s., 1H) 5.63 (td, J=10.42, 5.27 Hz, 1H) 5.02 (t, J=10.29 Hz, 1H) 4.66 (dd, J=10.04, 7.03 Hz, 1H) 4.22-4.36 (m, 2H) 4.13 (d, J=11.04 Hz, 2H) 3.99-4.08 (m, 2H) 3.44 (dd, J=7.03, 2.51 Hz, 2H) 2.71 (s, 2H) 2.49 (s, 3H) 1.84-2.02 (m, 2H) 1.77 (dd, J=8.03, 5.52 Hz, 1H) 1.64-1.72 (m, 2H) 1.59 (dd, J=9.29, 5.77 Hz, 2H) 1.35-1.55 (m, 9H) 1.26 (br. s., 2H) 1.20 (d, J=7.03 Hz, 5H) 1.00 (d, J=6.53 Hz, 3H) 0.85-0.94 (m, 2H). MS: MS m/z 835.4 (M$^+$+1).

Preparation of Compound 1055 and Compound 1056

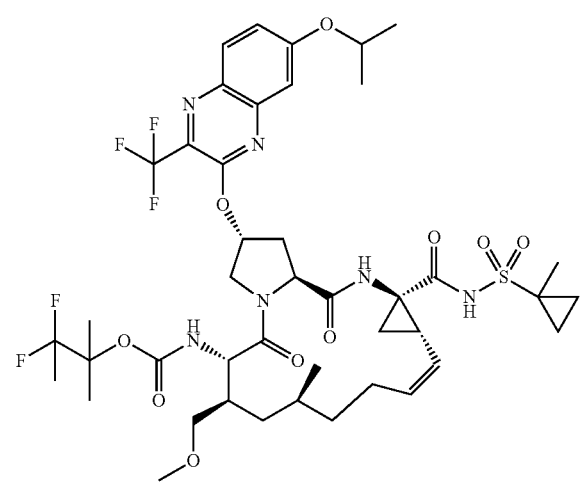

Compound 1055

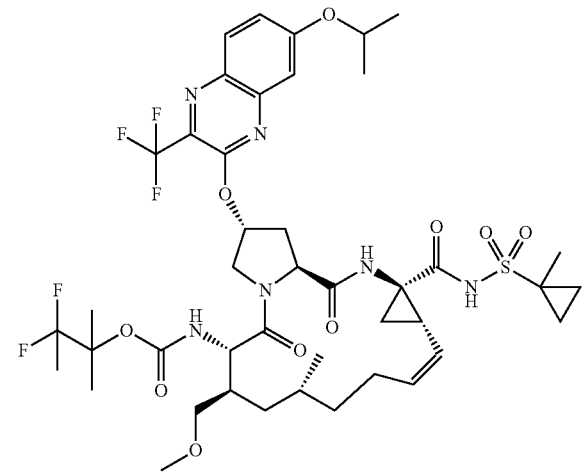

Compound 1056

Compound 1055 and Compound 1056 were prepared using the intermediates described herein and by following the general procedure described for the synthesis of Compound 1016 using 3,3-difluoro-2-methylbutan-2-ylpyridin-2-yl carbonate instead of pyridin-2-yl (1,1,1-trifluoro-2-methylpropan-2-yl) carbonate.

Compound 1055: 3,3-difluoro-2-methylbutan-2-yl ((2R,6S,7R,9S,13aS,14aR,16aS,Z)-2-((7-isopropoxy-3-(trifluoromethyl)quinoxalin-2-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, METHANOL-d$_4$) δ ppm 7.99 (s, 1H) 7.27-7.44 (m, 2H) 6.02 (br. s., 1H) 5.64-5.79 (m, 1H) 5.06 (t, J=9.54 Hz, 1H) 4.90-4.97 (m, 1H) 4.67-4.77 (m, 1H) 4.56 (d, J=13.55 Hz, 1H) 4.48 (d, J=6.02 Hz, 1H) 4.06-4.16 (m, 1H) 3.47 (d, J=6.02 Hz, 2H) 2.66 (d, J=7.03 Hz, 1H) 2.55 (dd, J=9.04, 4.02 Hz, 3H) 2.07-2.19 (m, 1H) 2.01 (s, 1H) 1.72 (dd, J=8.03, 5.52 Hz, 1H) 1.38-1.69 (m, 15H) 1.15-1.37 (m, 9H) 0.83-0.98 (m, 6H). MS: MS m/z 945.4 (M$^+$+1).

Compound 1056: 3,3-difluoro-2-methylbutan-2-yl ((2R,6S,7R,9R,13aS,14aR,16aS,Z)-2-((7-isopropoxy-3-(trifluoromethyl)quinoxalin-2-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, METHANOL-d$_4$) δ ppm 7.99 (s, 1H) 7.30-7.42 (m, 2H) 5.99 (br. s., 1H) 5.63 (td, J=10.29, 6.02 Hz, 1H) 5.02 (t, J=10.04 Hz, 1H) 4.89-4.97 (m, 1H) 4.55-4.69 (m, 2H) 4.16 (d, J=11.04 Hz, 1H) 4.06 (dd, J=11.80, 3.26 Hz, 1H) 3.44 (dd, J=4.77, 2.76 Hz, 2H) 3.27 (s, 2H) 2.71 (d, J=9.04 Hz, 2H) 2.48 (d, J=13.55 Hz, 2H) 1.94 (d, J=11.04 Hz, 2H) 1.77 (dd, J=8.28, 5.77 Hz, 1H) 1.67 (d, J=10.04 Hz, 1H) 1.40-1.62 (m, 14H) 1.27 (d, J=11.55 Hz, 3H) 0.96-1.16 (m, 9H) 0.83-0.95 (m, 3H). MS: MS m/z 945.4 (M$^+$+1).

Preparation of Compound 1057 and Compound 1058

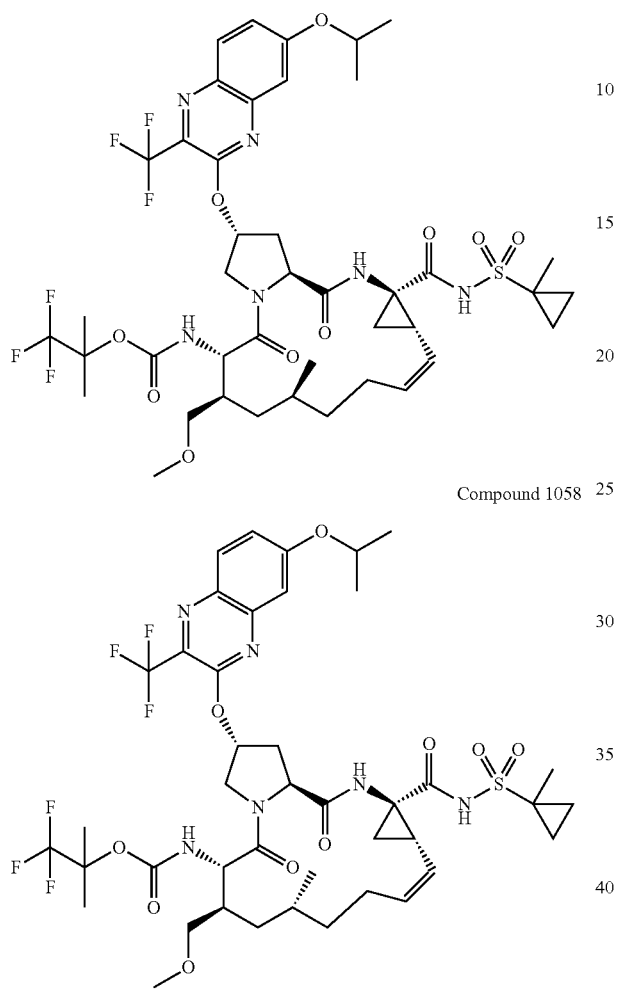

Compound 1057

Compound 1058

Compound 1057 and Compound 1058 were prepared using the intermediates described herein and by following the general procedure described for the synthesis of Compound 1016.

Compound 1057: 1,1,1-trifluoro-2-methylpropan-2-yl ((2R,6S,7R,9S,13aS,14aR,16aS,Z)-2-((7-isopropoxy-3-(trifluoromethyl)quinoxalin-2-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, METHANOL-$d_4$) δ ppm 7.99 (s, 1H) 7.30-7.42 (m, 2H) 6.01 (br. s., 1H) 5.66-5.81 (m, 1H) 5.00-5.11 (m, 1H) 4.90-4.98 (m, 1H) 4.66-4.78 (m, 1H) 4.57 (d, J=11.55 Hz, 1H) 4.47 (d, J=6.53 Hz, 1H) 4.09 (dd, J=11.80, 3.26 Hz, 1H) 3.40-3.49 (m, 2H) 2.69 (dd, J=13.55, 7.53 Hz, 3H) 2.49-2.63 (m, 3H) 2.44 (d, J=8.03 Hz, 3H) 2.11 (br. s., 1H) 2.01 (br. s., 2H) 1.69-1.76 (m, 1H) 1.55-1.68 (m, 2H) 1.39-1.54 (m, 9H) 1.13-1.38 (m, 7H) 0.79-1.02 (m, 7H). MS: MS m/z 949.5 (M$^+$+1).

Compound 1058: 1,1,1-trifluoro-2-methylpropan-2-yl ((2R,6S,7R,9R,13aS,14aR,16aS,Z)-2-((7-isopropoxy-3-(trifluoromethyl)quinoxalin-2-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, METHANOL-$d_4$) δ ppm 7.99 (s, 1H) 7.30-7.41 (m, 2H) 5.98 (br. s., 1H) 5.63 (td, J=10.16, 5.27 Hz, 1H) 5.02 (t, J=10.29 Hz, 1H) 4.90-4.97 (m, 1H) 4.53-4.71 (m, 1H) 4.15 (d, J=10.54 Hz, 1H) 4.05 (d, J=8.53 Hz, 1H) 3.44 (dd, J=5.77, 2.76 Hz, 2H) 2.70 (d, J=8.53 Hz, 3H) 2.48 (d, J=14.06 Hz, 3H) 1.85-2.05 (m, 3H) 1.77 (dd, J=8.28, 5.77 Hz, 1H) 1.63-1.72 (m, 1H) 1.59 (dd, J=9.29, 5.77 Hz, 2H) 1.36-1.55 (m, 11H) 1.11-1.34 (m, 7H) 1.00 (d, J=6.53 Hz, 4H) 0.83-0.95 (m, 3H). MS: MS m/z 949.5 (M$^+$+1).

Preparation of Compound 1059 and 1060

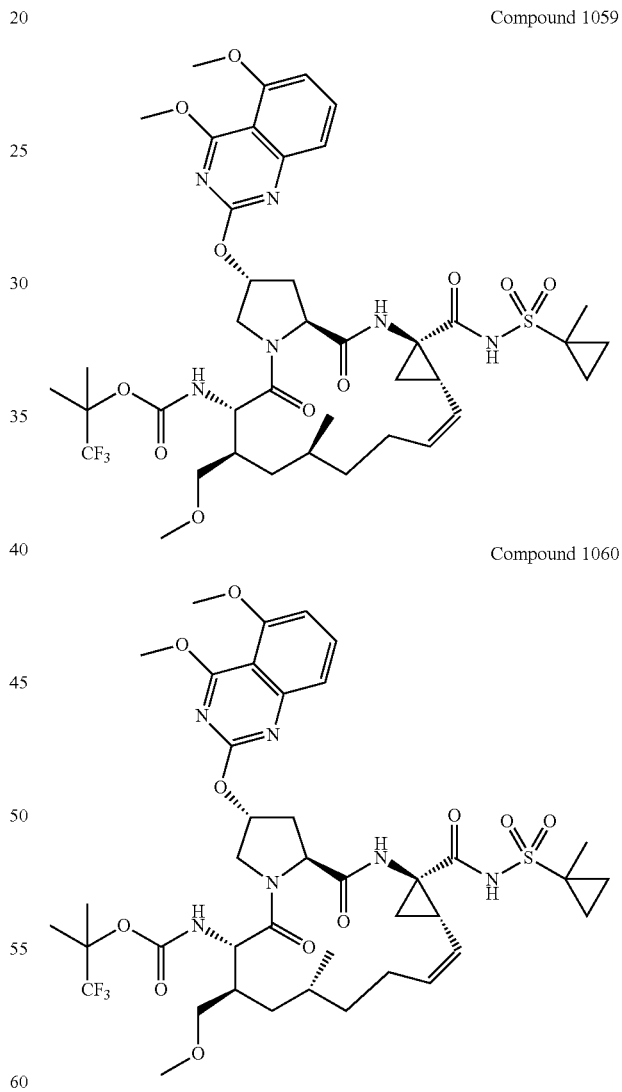

Compound 1059

Compound 1060

Compound 1059 and compound 1060 were prepared using the intermediates described herein and by following the general procedure described for the synthesis of Compound 1016.

Compound 1059: 1,1,1-trifluoro-2-methylpropan-2-yl ((2R,6S,7R,9S,13aS,14aR,16aS,Z)-2-((4,5-dimethoxyquinazolin-2-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. ¹H NMR (400 MHz, METHANOL-d₄) δ ppm 7.68 (t, J=8.28 Hz, 1H) 7.13-7.27 (m, 1H) 6.90 (d, J=7.78 Hz, 1H) 5.76 (br. s., 1H) 5.60 (td, J=10.35, 5.65 Hz, 1H) 5.00 (t, J=10.16 Hz, 1H) 4.73-4.80 (m, 1H) 4.50-4.68 (m, 1H) 4.08-4.25 (m, 4H) 3.96-4.08 (m, 1H) 3.83 (s, 3H) 3.37-3.50 (m, 2H) 3.21-3.29 (m, 3H) 2.57-2.72 (m, 2H) 2.28-2.47 (m, 2H) 1.83-2.02 (m, 2H) 1.75 (dd, J=8.41, 5.65 Hz, 1H) 1.59-1.69 (m, 1H) 1.39-1.55 (m, 9H) 1.20-1.34 (m, 6H) 1.05-1.15 (m, 3H) 0.90-1.00 (m, 3H) 0.81 (br. s., 2H). MS: MS m/z 883.4 (M⁺+1)

Compound 1060: 1,1,1-trifluoro-2-methylpropan-2-yl ((2R,6S,7R,9R,13aS,14aR,16aS,Z)-2-((4,5-dimethoxyquinazolin-2-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. ¹H NMR (400 MHz, METHANOL-d₄) δ ppm 7.69 (t, J=8.28 Hz, 1H) 7.21 (d, J=8.03 Hz, 1H) 6.90 (d, J=8.03 Hz, 1H) 5.64-5.83 (m, 2H) 5.03 (br. s., 1H) 4.66 (t, J=8.66 Hz, 1H) 4.47-4.59 (m, 3H) 4.16 (s, 3H) 4.06 (d, J=8.78 Hz, 1H) 3.95 (s, 3H) 3.38-3.53 (m, 3H) 2.53-2.68 (m, 4H) 2.44 (br. s., 3H) 2.05-2.17 (m, 2H) 1.98 (s, 1H) 1.36-1.72 (m, 14H) 1.15-1.33 (m, 6H) 0.80-0.97 (m, 5H). MS: MS m/z 883.3 (M⁺+1).

Preparation of Compound 1061

Compound 1061

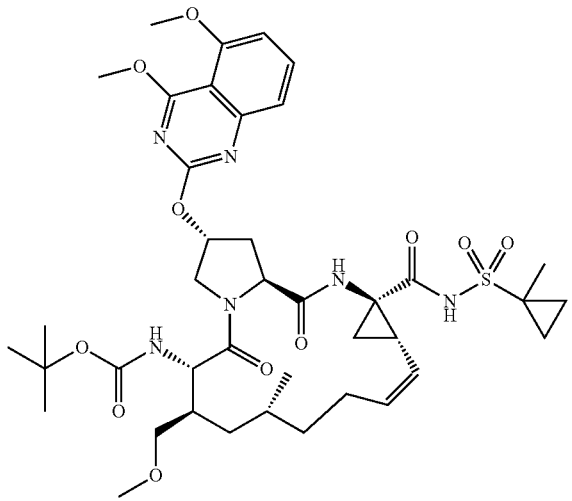

Compound 1061 was prepared using the intermediates described herein and by following the general procedure described for the synthesis of Compound 1010.

Compound 1061: tert-butyl ((2R,6S,7R,9R,13aS,14aR,16aS,Z)-2-((4,5-dimethoxyquinazolin-2-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. ¹H NMR (400 MHz, METHANOL-d₄) δ ppm 7.69 (t, J=8.28 Hz, 1H) 7.21 (d, J=8.53 Hz, 1H) 6.90 (d, J=8.03 Hz, 1H) 5.80 (br. s., 1H) 5.62 (td, J=10.29, 5.52 Hz, 1H) 4.91-5.10 (m, 2H) 4.71-4.81 (m, 2H) 4.52-4.66 (m, 3H) 4.14-4.29 (m, 3H) 4.06 (dd, J=11.80, 3.26 Hz, 1H) 3.91-4.01 (m, 3H) 3.37-3.52 (m, 2H) 3.24-3.30 (m, 3H) 2.63-2.78 (m, 2H) 2.33-2.51 (m, 2H) 1.88-2.05 (m, 10H) 1.77 (dd, J=8.28, 5.77 Hz, 1H) 1.61-1.69 (m, 1H) 1.41-1.55 (m, 6H) 1.04-1.38 (m, 10H) 0.93-1.04 (m, 3H) 0.80-0.92 (m, 3H), MS: MS m/z 829.2 (M⁺+1).

Preparation of Compound 1062

Compound 1062

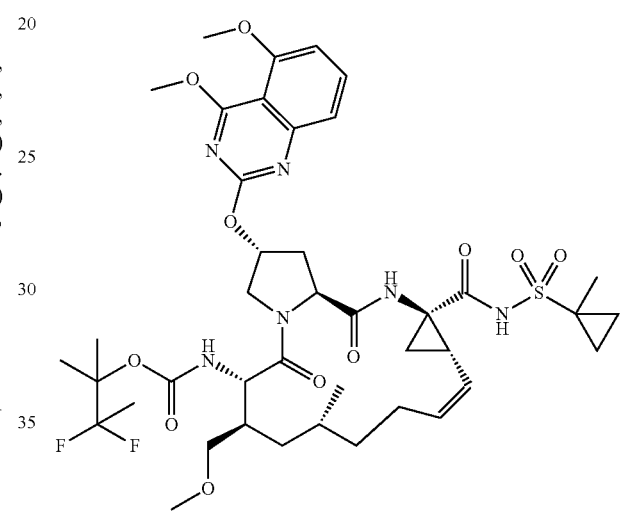

Compound 1062 was prepared using the intermediates described herein and by following the general procedure described for the synthesis of Compound 1016 using 3,3-difluoro-2-methylbutan-2-ylpyridin-2-yl carbonate instead of pyridin-2-yl (1,1,1-trifluoro-2-methylpropan-2-yl) carbonate.

Compound 1062: 3,3-difluoro-2-methylbutan-2-yl ((2R,6S,7R,9R,13aS,14aR,16aS,Z)-2-((4,5-dimethoxyquinazolin-2-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. ¹H NMR (400 MHz, METHANOL-d₄) ppm 7.71 (t, J=8.28 Hz, 1H) 7.22 (d, J=7.53 Hz, 1H) 6.94 (s, 1H) 5.79 (br. s., 1H) 5.62 (s, 1H) 4.99 (s, 1H) 4.81 (d, J=13.05 Hz, 2H) 4.51-4.70 (m, 1H) 4.14-4.32 (m, 4H) 4.06 (dd, J=12.05, 3.51 Hz, 1H) 3.98 (s, 3H) 3.38-3.50 (m, 2H) 3.28 (s, 4H) 2.68 (dd, J=14.31, 7.28 Hz, 2H) 2.31-2.53 (m, 2H) 1.85-2.05 (m, 2H) 1.77 (dd, J=8.28, 5.77 Hz, 1H) 1.39-1.64 (m, 14H) 1.09-1.34 (m, 6H) 0.92-1.08 (m, 6H) 0.89 (br. s., 2H). MS: MS m/z 880.3 (M⁺+1).

Preparation of Compound 1063 and 1064

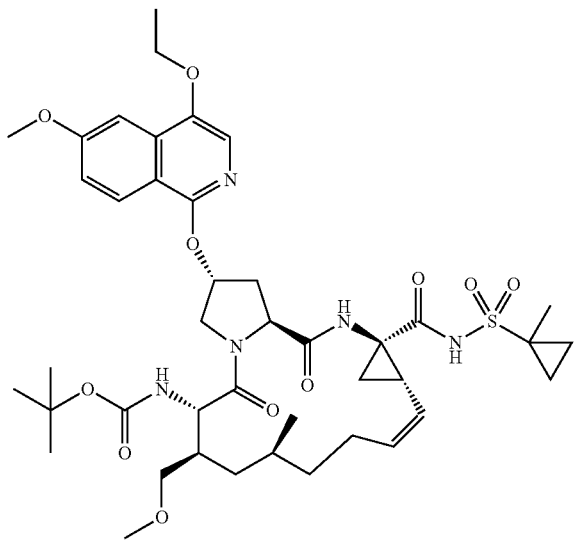

Compound 1063

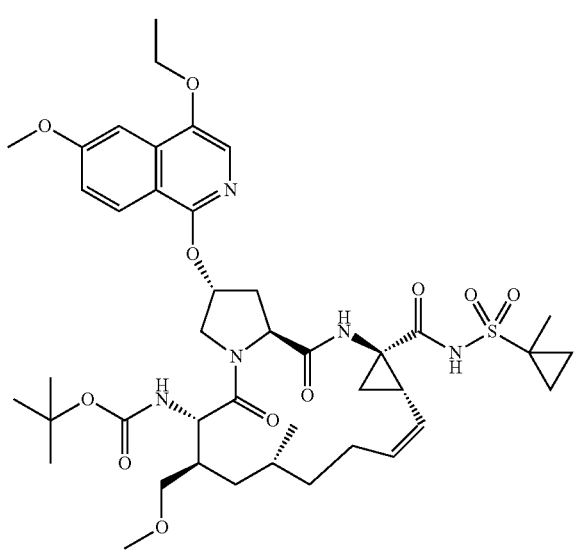

Compound 1064

Compound 1063 and Compound 1064 were prepared using the intermediates described herein and by following the general procedure described for the synthesis of Compound 1010.

Compound 1063: tert-butyl ((2R,6S,7R,9S,13aS,14aR,16aS,Z)-2-((4-ethoxy-6-methoxyisoquinolin-1-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, METHANOL-d$_4$) δ ppm 8.09 (br. s., 1H) 7.39-7.57 (m, 2H) 7.05-7.23 (m, 1H) 5.66-5.92 (m, 2H) 4.98-5.10 (m, 1H) 4.54-4.73 (m, 2H) 4.36-4.50 (m, 1H) 4.24 (q, J=6.86 Hz, 2H) 4.01-4.15 (m, 1H) 3.96 (s, 3H) 3.38-3.56 (m, 4H) 2.53-2.77 (m, 2H) 2.28-2.51 (m, 2H) 2.07-2.23 (m, 1H) 1.89-2.03 (m, 1H) 1.72 (br. s., 1H) 1.39-1.66 (m, 9H) 1.03-1.35 (m, 9H) 0.82-1.00 (m, 4H). MS: MS m/z 842.6 (M$^+$+1).

Compound 1064: tert-butyl ((2R,6S,7R,9R,13aS,14aR,16aS,Z)-2-((4-ethoxy-6-methoxyisoquinolin-1-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 842.6 (M$^+$+1).

Preparation of Compound 1065 and 1066

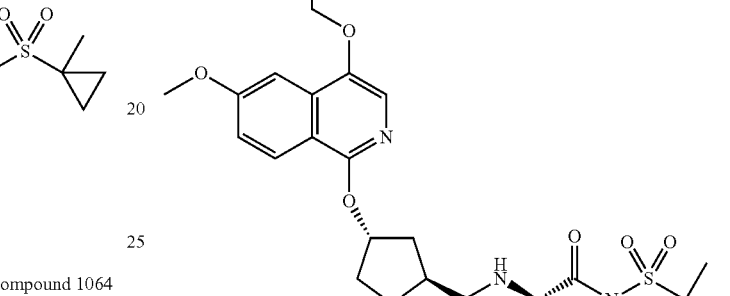

Compound 1065 and Compound 1066 were prepared using the intermediates described herein and by following the general procedure described for the synthesis of Compound 1016.

Compound 1065: 1,1,1-trifluoro-2-methylpropan-2-yl ((2R,6S,7R,9S,13aS,14aR,16aS,Z)-2-((4-ethoxy-6-methoxyisoquinolin-1-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a- hexadecahydrocyclopropa[e]pyrrolo[1,2-a][1,4]diazacyclopentadecin-6-yl)carbamate. MS: MS m/z 896.5 (M$^+$+1).

Compound 1066: 1,1,1-trifluoro-2-methylpropan-2-yl ((2R,6S,7R,9R,13aS,14aR,16aS,Z)-2-((4-ethoxy-6-methoxyisoquinolin-1-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, METHANOL-d$_4$) δ ppm 8.08 (d, J=9.54 Hz, 1H) 7.53 (s, 1H) 7.45 (d, J=2.51 Hz, 1H) 7.15 (dd, J=9.29, 2.76 Hz, 1H) 5.80 (br. s., 1H) 5.55-5.70 (m, 1H) 4.94-5.08 (m, 1H) 4.72-4.79 (m, 1H) 4.53-4.69 (m, 2H) 4.16-4.33 (m, 3H) 3.96 (s, 4H) 3.46 (dd, J=5.27, 2.76 Hz, 2H) 2.63-2.82 (m, 2H) 2.25-2.52 (m, 3H) 1.87-2.10 (m, 2H) 1.73-1.82 (m, 1H) 1.62-1.71 (m, 1H) 1.16-1.61 (m, 14H) 0.96-1.09 (m, 4H) 0.90 (s, 2H). MS: MS m/z 896.5 (M$^+$+1).

Preparation of Compound 1067 and 1068

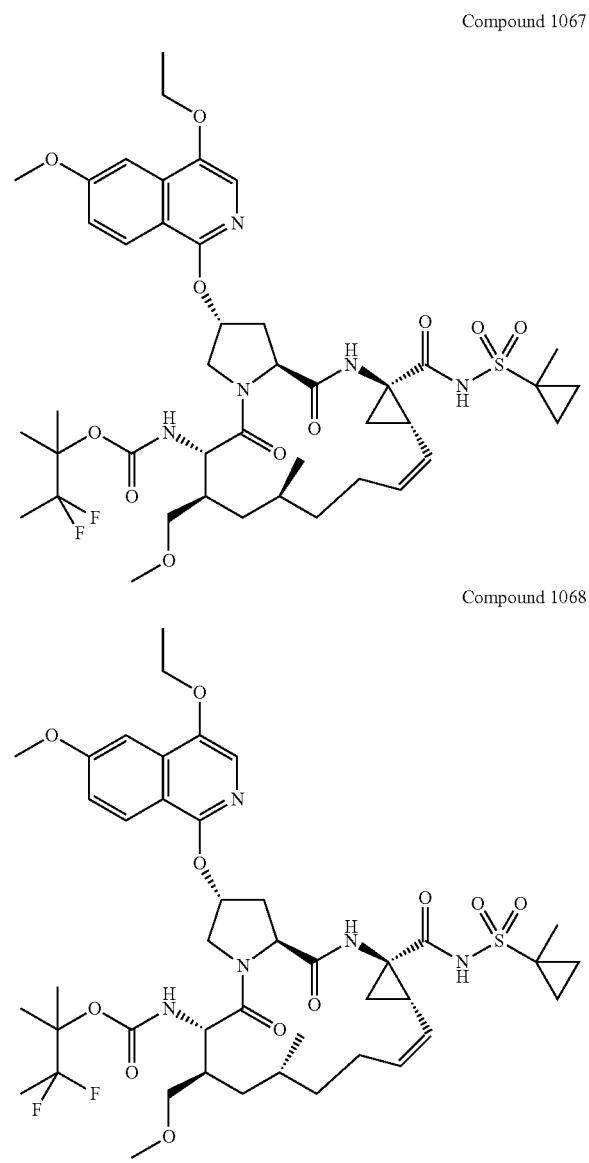

Compound 1067

Compound 1068

Compound 1067 and Compound 1068 were prepared using the intermediates described herein and by following the general procedure described for the synthesis of Compound 1016 using 3,3-difluoro-2-methylbutan-2-ylpyridin-2-yl carbonate instead of pyridin-2-yl (1,1,1-trifluoro-2-methylpropan-2-yl) carbonate.

Compound 1067: 3,3-difluoro-2-methylbutan-2-yl ((2R,6S,7R,9S,13aS,14aR,16aS,Z)-2-((4-ethoxy-6-methoxyisoquinolin-1-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, METHANOL-d$_4$) δ ppm 8.10 (d, J=9.04 Hz, 1H) 7.52 (s, 1H) 7.45 (d, J=2.51 Hz, 1H) 7.15 (dd, J=9.04, 2.51 Hz, 1H) 5.82 (br. s., 2H) 4.99-5.11 (m, 1H) 4.70 (br. s., 1H) 4.58 (s, 1H) 4.45 (d, J=11.04 Hz, 1H) 4.24 (q, J=7.03 Hz, 2H) 4.05 (br. s., 1H) 3.96 (s, 2H) 3.45-3.56 (m, 2H) 2.70 (br. s., 2H) 2.43 (br. s., 2H) 1.83-2.25 (m, 3H) 1.72 (br. s., 1H) 1.39-1.67 (m, 9H) 1.14-1.36 (m, 3H) 0.80-1.01 (m, 3H). MS: MS m/z 892.4 (M$^+$+1).

Compound 1068: 3,3-difluoro-2-methylbutan-2-yl ((2R,6S,7R,9R,13aS,14aR,16aS,Z)-2-((4-ethoxy-6-methoxyisoquinolin-1-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 892.3 (M$^+$+1).

Biological Studies

HCV NS3/4A protease complex enzyme assays and cell-based HCV replicon assays were utilized in the present disclosure, and were prepared, conducted and validated as follows:

Generation of Recombinant HCV NS3/4A Protease Complex

HCV NS3 protease complexes, derived from the BMS strain, H77 strain or J4L6S strain, were generated, as described below. These purified recombinant proteins were generated for use in a homogeneous assay (see below) to provide an indication of how effective compounds of the present disclosure would be in inhibiting HCV NS3 proteolytic activity.

Serum from an HCV-infected patient was obtained from Dr. T. Wright, San Francisco Hospital. An engineered full-length cDNA (compliment deoxyribonucleic acid) template of the HCV genome (BMS strain) was constructed from DNA fragments obtained by reverse transcription-PCR (RT-PCR) of serum RNA (ribonucleic acid) and using primers selected on the basis of homology between other genotype 1a strains. From the determination of the entire genome sequence, a genotype 1a was assigned to the HCV isolate according to the classification of Simmonds et al. (See P Simmonds, K A Rose, S Graham, S W Chan, F McOmish, B C Dow, E A Follett, P L Yap and H Marsden, *J. Clin. Microbiol.*, 31(6), 1493-1503 (1993)). The amino acid sequence of the nonstructural region, NS2-5B, was shown to be >97% identical to HCV genotype 1a (H77) and 87% identical to genotype 1b (J4L6S). The infectious clones, H77 (1a genotype) and J4L6S (1b genotype) were obtained from R. Purcell (NIH) and the sequences are published in Genbank (AAB67036, see Yanagi, M., Purcell, R. H., Emerson, S. U. and Bukh, *J. Proc. Natl. Acad. Sci. U.S.A.* 94(16), 8738-8743 (1997); AF054247, see Yanagi, M., St Claire, M., Shapiro, M., Emerson, S. U., Purcell, R. H. and Bukh, J., *Virology* 244 (1), 161-172. (1998)).

The H77 and J4L6S strains were used for production of recombinant NS3/4A protease complexes. DNA encoding the recombinant HCV NS3/4A protease complex (amino acids 1027 to 1711) for these strains was manipulated as described by P. Gallinari et al. (see Gallinari P, Paolini C, Brennan D, Nardi C, Steinkuhler C, De Francesco R. *Biochemistry.* 38(17):5620-32, (1999)). Briefly, a three-lysine solubilizing tail was added at the 3'-end of the NS4A coding region. The cysteine in the P1 position of the NS4A-NS4B cleavage site (amino acid 1711) was changed to a glycine to avoid the proteolytic cleavage of the lysine tag. Furthermore, a cysteine to serine mutation was introduced by PCR at amino acid position 1454 to prevent the autolytic cleavage in the NS3 helicase domain. The variant DNA fragment was cloned in the pET21b bacterial expression vector (Novagen) and the NS3/4A complex was expressed in *Escherichia coli* strain BL21 (DE3) (Invitrogen) following the protocol described by P. Gallinari et al. (see Gallinari P, Brennan D, Nardi C, Brunetti M, Tomei L, Steinkuhler C, De Francesco R., *J Virol.* 72(8):6758-69 (1998)) with modifications. Briefly, the NS3/4A protease complex expression was induced with 0.5 millimolar (mM) Isopropyl β-D-1-thiogalactopyranoside (IPTG) for 22 hours (h) at 20° C. A typical fermentation (1 Liter (L)) yielded approximately 10 grams (g) of wet cell paste. The cells were resuspended in lysis buffer (10 mL/g) consisting of 25 mM N-(2-Hydroxyethyl)Piperazine-N'-(2-Ethane Sulfonic acid) (HEPES), pH 7.5, 20% glycerol, 500 mM Sodium Chloride (NaCl), 0.5% Triton X-100, 1 microgram/milliliter ("μg/mL") lysozyme, 5 mM Magnesium Chloride ($MgCl_2$), 1 μg/ml DnaseI, 5 mM β-Mercaptoethanol (βME), Protease inhibitor-Ethylenediamine Tetraacetic acid (EDTA) free (Roche), homogenized and incubated for 20 minutes (min) at 4° C. The homogenate was sonicated and clarified by ultra-centrifugation at 235000 g for 1 hour (h) at 4° C. Imidazole was added to the supernatant to a final concentration of 15 mM and the pH adjusted to 8.0. The crude protein extract was loaded on a Nickel-Nitrilotriacetic acid (Ni-NTA) column pre-equilibrated with buffer B (25 mM HEPES, pH 8.0, 20% glycerol, 500 mM NaCl, 0.5% Triton X-100, 15 mM imidazole, 5 mM βME). The sample was loaded at a flow rate of 1 mL/min. The column was washed with 15 column volumes of buffer C (same as buffer B except with 0.2% Triton X-100). The protein was eluted with 5 column volumes of buffer D (same as buffer C except with 200 mM Imidazole).

NS3/4A protease complex-containing fractions were pooled and loaded on a desalting column Superdex-S200 pre-equilibrated with buffer D (25 mM HEPES, pH 7.5, 20% glycerol, 300 mM NaCl, 0.2% Triton X-100, 10 mM βME). Sample was loaded at a flow rate of 1 mL/min. NS3/4A protease complex-containing fractions were pooled and concentrated to approximately 0.5 mg/ml. The purity of the NS3/4A protease complexes, derived from the BMS, H77 and J4L6S strains, were judged to be greater than 90% by SDS-PAGE and mass spectrometry analyses. The enzyme was stored at −80° C., thawed on ice and diluted prior to use in assay buffer.

FRET Peptide Assay to Monitor HCV NS3/4A Proteolytic Activity

The purpose of this in vitro assay was to measure the inhibition of HCV NS3 protease complexes, derived from the BMS strain, H77 strain or J4L6S strain, as described above, by compounds of the present disclosure. This assay provides an indication of how effective compounds of the present disclosure would be in inhibiting HCV NS3 proteolytic activity.

In order to monitor HCV NS3/4A protease activity, an NS3/4A peptide substrate was used. The substrate was RET S1 (Resonance Energy Transfer Depsipeptide Substrate; AnaSpec, Inc. cat #22991)(FRET peptide), described by Taliani et al. in *Anal. Biochem.* 240(2):60-67 (1996). The sequence of this peptide is loosely based on the NS4A/NS4B natural cleavage site for the HCV NS3 protease except there is an ester linkage rather than an amide bond at the cleavage site. The peptide also contains a fluorescence donor, EDANS, near one end of the peptide and an acceptor, DABCYL, near the other end. The fluorescence of the peptide is quenched by intermolecular resonance energy transfer (RET) between the donor and the acceptor, but as the NS3 protease cleaves the peptide the products are released from RET quenching and the fluorescence of the donor becomes apparent.

The peptide substrate was incubated with one of the three recombinant NS3/4A protease complexes, in the absence or presence of a compound of the present disclosure. The inhibitory effects of a compound were determined by monitoring the formation of fluorescent reaction product in real time using a Cytofluor Series 4000.

The reagents were as follow: HEPES and Glycerol (Ultrapure) were obtained from GIBCO-BRL. Dimethyl Sulfoxide (DMSO) was obtained from Sigma. β-Mercaptoethanol was obtained from Bio Rad.

Assay buffer: 50 mM HEPES, pH 7.5; 0.15 M NaCl; 0.1% Triton; 15% Glycerol; 10 mM βME. Substrate: 2 μM final concentration (from a 2 mM stock solution in DMSO stored at −20° C.). HCV NS3/4A protease type 1a (1b), 2-3 nM final concentration (from a 5 μM stock solution in 25 mM HEPES, pH 7.5, 20% glycerol, 300 mM NaCl, 0.2% Triton-X100, 10 mM βME). For compounds with potencies approaching the assay limit, the assay was made more sensitive by adding 50 μg/ml Bovine Serum Albumin (Sigma) to the assay buffer and reducing the end protease concentration to 300 pM.

The assay was performed in a 96-well polystyrene black plate from Falcon. Each well contained 25 μl NS3/4A protease complex in assay buffer, 50 μl of a compound of the present disclosure in 10% DMSO/assay buffer and 25 μl substrate in assay buffer. A control (no compound) was also prepared on the same assay plate. The enzyme complex was mixed with compound or control solution for 1 min before initiating the enzymatic reaction by the addition of substrate. The assay plate was read immediately using the Cytofluor Series 4000 (Perspective Biosystems). The instrument was set to read an emission of 340 nm and excitation of 490 nm at 25° C. Reactions were generally followed for approximately 15 min.

The percent inhibition was calculated with the following equation:

$$100-[(\delta F_{inh}/\delta F_{con})\times 100]$$

where δF is the change in fluorescence over the linear range of the curve. A non-linear curve fit was applied to the inhibition-concentration data, and the 50% effective concentration ($IC_{50}$) was calculated by the use of Excel XLfit software using the equation, $y=A+((B-A)/(1+((C/x)^D)))$.

Compounds of the present disclosure, which were tested against more than one type of NS3/4A complex, were found to have similar inhibitory properties though the compounds uniformly demonstrated greater potency against the 1b strains as compared to the 1a strains.

Generation of HCV Replicon

An HCV replicon whole cell system was established as described by Lohmann V, Korner F, Koch J, Herian U, Theilmann L, Bartenschlager R., Science 285(5424):110-3 (1999) and modified to introduce a luciferase reporter, as first described by Krieger et al (Krieger N, Lohmann V, and Bartenschlager R, *J. Virol.* 75(10):4614-4624 (2001)). CDNA encoding a humanized form of the *Renilla luciferase* gene and a linker sequence fused directly to the 3'-end of the luciferase gene were introduced into the replicon construct using an Asc1 restriction site located in core, directly upstream of the neomycin marker gene. The adaptive mutation at position 1179 (serine to isoleucine) was also introduced (Blight K J, Kolykhalov, A A, Rice, C M, *Science* 290(5498):1972-1974). A stable cell line constitutively expressing this HCV replicon construct was generated by first linearizing plasmid DNAs with ScaI. RNA transcripts were synthesized in vitro using the T7 MegaScript transcription kit (Ambion, Austin, Tex.) according to manufacturer's directions. In vitro transcripts of the cDNA were transfected into the human hepatoma cell line, HUH-7. Selection for cells constitutively expressing the HCV replicon was achieved in the presence of the selectable marker, neomycin (G418). Resulting cell lines were characterized for positive and negative strand RNA production and protein production over time.

A stable HCV replicon luciferase reporter cell line representing the genotype 1a H77 strain (Yanagi M, Purcell R H, Emerson S U, et al. Transcripts from a single full-length cDNA clone of hepatitis C virus are infectious when directly transfected into the liver of a chimpanzee. Proc Natl Acad Sci USA 1997; 94(16):8738-8743) was generated as described previously for the genotype 1b (Con1) replicon luciferase cell line. The replicon construct was modified by introducing mutations were introduced into the genes encoding the NS3 helicase domain (proline replaced by leucine at position 1496) and NS5A (serine to isoleucine at position 2204) to improve replication in cell culture.

HCV Replicon Luciferase Reporter Assay

HCV replicon luciferase assays were developed to monitor the inhibitory effects of compounds described in the disclosure on HCV genotypes 1a and 1b viral replication. HUH-7 cells, constitutively expressing the HCV replicon, were grown in Dulbecco's Modified Eagle Media (DMEM) (Gibco-BRL) containing 10% Fetal calf serum (FCS) (Sigma) and 1 mg/mL G418 (Gibco-BRL). Compounds were serially diluted 3 folds in DMSO for a twenty-point titration and subsequently transferred to sterile 384-well tissue-culture treated plates (Corning cat #3571). The plates were then seeded with 50 µL of cells at a density of $3.0 \times 10^3$ cells/well in DMEM containing 4% FCS (final DMSO concentration at 0.5%). After 3 days incubation at 37° C., cells were analyzed for *Renilla Luciferase* activity using the EnduRen as substrate (Promega cat #E6485). The EnduRen substrate was diluted in DMEM and then added to the plates to a final concentration of 7.5 µM. The plates were incubated for 2 hrs at 37° C. and then read immediately for 30 seconds with Viewlux Imager (PerkinElmer) using a luminescence program. To assess cytotoxicity of compounds, $CC_{50}$ values were generated by multiplexing the EnduRen-containing plates with Cell Titer-Blue (Promega, cat # G8082). Cell-Titer Blue (3 µL) was added to each well and incubated for 8 hrs at 37° C. The fluorescence signal from each well was read, with an excitation wavelength at 525/10 nm and an emission wavelength of 598/10 nm, using the Viewlux Imager.

The $EC_{50}$ values for compounds were calculated by using a four-parameter logistic equation:

$$y=A+((B-A)/(1+((C/x)\hat{\,}D))),$$

where A and B denotes minimal and maximal % inhibition, respectively, C is the $EC_{50}$, D is the hill slope and x represents compound concentration.

Table 2 shows the EC50 values of representative compounds of the present disclosure. Ranges are as follows: A=0.10 nM-0.50 nM; B=0.51 nM-1.00 nM; C=1.01 nM-5.00 nM; D=5.01 nM-35.00 nM; E=35.01 nM-620 nM.

TABLE 2

| Compound Number | LE_1a (EC50, nM) | LE_1a (EC50, range) | LE_1b (EC50, nM) | LE_1b (EC50, range) |
|---|---|---|---|---|
| 1001 | | C | | B |
| 1002 | | B | | A |
| 1003 | | B | | A |
| 1004 | | C | | C |
| 1005 | | C | | A |
| 1006 | | D | | C |
| 1007 | | C | | B |
| 1008 | | C | | C |
| 1009 | | C | | C |
| 1010 | | B | | A |
| 1011 | | C | | C |
| 1012 | | B | | A |
| 1013 | | C | | C |
| 1014 | | C | | B |
| 1015 | | C | | C |
| 1016 | 0.84 | B | 0.26 | A |
| 1017 | | C | | B |
| 1018 | | C | | C |
| 1019 | | C | | B |
| 1020 | | C | | B |
| 1021 | | C | | A |
| 1022 | | C | | C |
| 1023 | | C | | A |
| 1024 | | E | | D |
| 1025 | 7.01 | D | 1.38 | C |
| 1027 | | D | | C |
| 1028 | | B | | A |
| 1029 | 1.78 | C | 0.63 | B |
| 1030 | | E | | D |
| 1031 | | D | | C |
| 1032 | | B | | A |
| 1033 | | D | | C |
| 1034 | | C | | B |
| 1035 | | C | | C |
| 1036 | | E | | D |
| 1037 | | C | | C |
| 1038 | 35.02 | E | 14.72 | D |
| 1039 | | D | | C |
| 1040 | | E | | E |
| 1041 | 0.61 | B | 0.75 | B |
| 1042 | | D | | C |
| 1043 | | C | | B |
| 1045 | | | | C |
| 1046 | | | | C |
| 1047 | | | | B |
| 1048 | | | 0.27 | A |
| 1049 | | | | C |
| 1050 | | | | A |
| 1051 | | | | C |
| 1052 | | | | A |
| 1053 | | | | C |
| 1054 | | | | A |
| 1055 | | | | C |
| 1056 | | | | A |
| 1057 | | | | D |

TABLE 2-continued

| Compound Number | LE_1a (EC50, nM) | LE_1a (EC50, range) | LE_1b (EC50, nM) | LE_1b (EC50, range) |
|---|---|---|---|---|
| 1058 | | | | A |
| 1059 | | | | E |
| 1060 | | | | C |
| 1061 | | | | D |
| 1062 | | | | C |
| 1063 | | | | A |
| 1064 | | | | A |
| 1065 | | | | A |
| 1066 | | | | A |
| 1067 | | | 0.50 | |
| 1068 | | | | A |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A compound of formula (I)

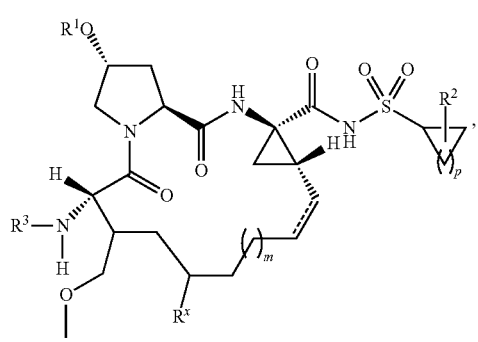

or a pharmaceutically acceptable salt thereof, wherein
p is 1 or 2;
----- is a single or double bond;
m is 0, 1, or 2;
$R^1$ is

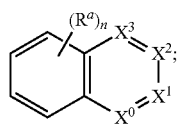

wherein $R^1$ is attached to the parent molecular moiety through any substitutable carbon atom in the ring;
n is 0, 1, 2, 3, 4, 5, or 6;
$X^0$ is selected from CH and N;
$X^1$ is selected from CH and N;
$X^2$ and $X^3$ are independently selected from CH, C($R^a$) and N; provided that at least one of $X^1$, $X^2$, and $X^3$ is other than N;
each $R^a$ is independently selected from alkenyloxy, alkoxy, alkoxyalkoxy, alkoxycarbonyl, alkyl, benzodi-oxanyl, carboxamido, carboxy, carboxyalkoxy, cyano, cycloalkyl, cycloalkylalkoxy, cycloalkyloxy, deuteroalkoxy, dialkylamino, halo, haloalkyl, haloalkoxy, haloalkoxycarbonyl, hydroxy, imidazolyl, morpholinyl, oxazolyl, phenyl, piperazinyl, pyrazolyl, pyridinyl, pyrrolidinyl, thiazolyl, and —$NR^qR^{q'}$, wherein the imidazolyl, the morpholinyl, the oxazolyl, the phenyl, the piperazinyl, the pyridinyl, the pyrrolidinyl, and the thiazolyl are optionally substituted with one or two groups independently selected from alkoxy, alkyl, alkylsulfonyl, halo, haloalkoxy, haloalkyl, and morpholinyl; and wherein two adjacent $R^a$ groups, together with the carbon atoms to which they are attached, can optionally form a ring selected from dioxanyl, dioxolanyl, furanyl, morpholinyl, pyranyl, and phenyl, wherein the ring is optionally substituted with one or two groups independently selected from alkyl and halo;
$R^x$ is selected from hydrogen and methyl;
$R^2$ is selected from hydrogen, alkyl, deuteroalkyl, halo, haloalkoxy, haloalkyl, and hydroxyalkyl;
$R^3$ is selected from hydrogen, alkoxyalkoxycarbonyl, alkoxycarbonyl, alkylaminocarbonyl, alkylcarbonyl, cycloalkylalkoxycarbonyl, cycloalkylcarbonyl, cycloalkyloxycarbonyl, deuteroalkoxycarbonyl, deuterohaloalkoxycarbonyl, dialkylaminocarbonyl, dialkylaminocarbonylcarbonyl, haloalkoxycarbonyl, haloalkylaminocarbonyl, haloalkylcarbonyl, heterocyclylcarbonyl, heterocyclyloxycarbonyl, phenylcarbonyl, and phenyloxycarbonyl, wherein the cycloalkyl part of the cycloalkylalkoxycarbonyl, the cycloalkylcarbonyl, and the cycloalkyloxycarbonyl, the heterocyclyl part of the heterocyclylcarbonyl and the heterocyclyloxycarbonyl, and the phenyl part of the phenylcarbonyl and the phenyloxycarbonyl, is optionally substituted with one, two, or three groups independently selected from alkyl, alkylamino, alkylcarbonyl, cycloalkyl, dialkylamino, halo, haloalkoxy, and haloalkyl; and
one of $R^q$ and $R^{q'}$ is selected from hydrogen and alkyl and the other is selected from alkylcarbonyl and phenylcarbonyl.

2. A compound of claim 1, or a pharmaceutically acceptable salt thereof, wherein p is 1.

3. A compound of claim 2, or a pharmaceutically acceptable salt thereof, wherein ----- is a double bond.

4. A compound of claim 3, or a pharmaceutically acceptable salt thereof, wherein m is 1.

5. A compound of claim 4 wherein $R^1$ is

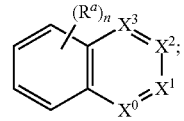

wherein $R^1$ is attached to the parent molecular moiety through any substitutable carbon atom in the ring;
n is 1,
q is 0, 1, 2, 3, or 4;
$X^0$ is selected from CH and N;
$X^1$ is selected from CH and N;
$X^2$ and $X^3$ are independently selected from CH, C($R^a$) and N; provided that at least one of $X^1$, $X^2$, and $X^3$ is other than N;

X⁴ is selected from CH and CR$^a$;
each R$^a$ is independently selected from alkoxy, alkyl, halo, and haloalkyl.

6. A compound of claim 1, or a pharmaceutically acceptable salt thereof, wherein R² is selected from hydrogen, alkyl, and haloalkyl.

7. A compound of claim 1, or a pharmaceutically acceptable salt thereof, wherein R³ is selected from alkoxycarbonyl and haloalkoxycarbonyl.

8. A compound of claim 1, or a pharmaceutically acceptable salt thereof, wherein
p is 1;
---- is a double bond;
m is 1; and
R¹ is

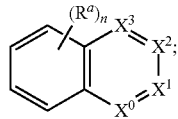

wherein
wherein R¹ is attached to the parent molecular moiety through any substitutable carbon atom in the ring;
n is 1,
q is 0, 1, 2, 3, or 4;
X⁰ is selected from CH and N;
X¹ is selected from CH and N;
X² and X³ are independently selected from CH, C(R$^a$) and N; provided that at least one of X¹, X², and X³ is other than N;
X⁴ is selected from CH and CR$^a$; and
each R$^a$ is independently selected from alkoxy, alkyl, halo, and haloalkyl.

9. A compound selected from
tert-butyl ((2R,6S,7R,9R,13aS,14aR,16aS,Z)-2-((4-methoxyisoquinolin-1-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

tert-butyl ((2R,6S,7R,9S,13aS,14aR,16aS,Z)-2-((4-methoxyisoquinolin-1-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9R,13aS,14aR,16aS,Z)-2-((4-methoxyisoquinolin-1-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl) carbamate;

1,1,1-trifluoro-2-methylpropan-2-yl ((2R,6S,7R,9S,13aS,14aR,16aS,Z)-2-((4-methoxyisoquinolin-1-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl) carbamate 1,1,1-trifluoro-2-methylpropan-2-yl ((2R,6S,7R,13aS,14aR,16aS,Z)-2-((6-methoxyisoquinolin-1-yl)oxy)-7-(methoxymethyl)-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,13aS,14aR,16aS,Z)-2-((4-methoxyisoquinolin-1-yl)oxy)-7-(methoxymethyl)-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

tert-butyl ((2R,6S,7R,9R,13aS,14aR,16aS,Z)-14a-((cyclopropylsulfonyl)carbamoyl)-2-((4-methoxyisoquinolin-1-yl)oxy)-7-(methoxymethyl)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

tert-butyl ((2R,6S,7R,9S,13aS,14aR,16aS,Z)-14a-((cyclopropylsulfonyl)carbamoyl)-2-((4-methoxyisoquinolin-1-yl)oxy)-7-(methoxymethyl)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

tert-butyl ((2R,6S,7R,9R,13aS,14aR,16aS,Z)-2-((6-methoxyisoquinolin-1-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

tert-butyl ((2R,6S,7R,9S,13aS,14aR,16aS,Z)-2-((6-methoxyisoquinolin-1-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

tert-butyl ((2R,6S,7R,13aS,14aR,16aS,Z)-2-((4-methoxyisoquinolin-1-yl)oxy)-7-(methoxymethyl)-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

tert-butyl ((2R,6S,7R,9S,13aS,14aR,16aS,Z)-14a-((cyclopropylsulfonyl)carbamoyl)-2-((6-methoxyisoquinolin-1-yl)oxy)-7-(methoxymethyl)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

tert-butyl ((2R,6S,7R,9R,13aS,14aR,16aS,Z)-14a-((cyclopropylsulfonyl)carbamoyl)-2-((6-methoxyisoquinolin-1-yl)oxy)-7-(methoxymethyl)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9R,13aS,14aR,16aS,Z)-14a-((cyclopropylsulfonyl)carbamoyl)-2-((4-methoxyisoquinolin-1-yl)oxy)-7-(methoxymethyl)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9S,13aS,14aR,16aS,Z)-14a-((cyclopropylsulfonyl)carbamoyl)-2-((4-methoxyisoquinolin-1-yl)oxy)-7-(methoxymethyl)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl((2R,6S,7R,9R,13aS,14aR,16aS,Z)-2-((6-methoxyisoquinolin-1-yl)oxy)-7-(methoxymethyl)-9-methyl-14a-(((1-methylcyclopropyl)sulfonyl)carbamoyl)-5,16-dioxo-1,2,3,5,6,7,8,9, 10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl((2R,6S,7R,9S,13aS,14aR,16aS,Z)-2-((6-methoxyisoquinolin-1-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9S,13aS,14aR,16aS,Z)-14a-((cyclopropylsulfonyl)carbamoyl)-2-((6-methoxyisoquinolin-1-yl)oxy)-7-(methoxymethyl)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9R,13aS,14aR,16aS,Z)-14a-((cyclopropylsulfonyl)carbamoyl)-2-((6-methoxyisoquinolin-1-yl)oxy)-7-(methoxymethyl)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

tert-butyl ((2R,6S,7R,13aS,14aR,16aS,Z)-14a-((cyclopropylsulfonyl)carbamoyl)-2-((7-methoxy-3-(trifluoromethyl)quinoxalin-2-yl)oxy)-7-(methoxymethyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,13aS,14aR,16aS,Z)-14a-((cyclopropylsulfonyl)carbamoyl)-2-((7-methoxy-3-(trifluoromethyl)quinoxalin-2-yl)oxy)-7-(methoxymethyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

tert-butyl ((2R,6S,7R,13aS,14aR,16aS,Z)-14a-((cyclopropylsulfonyl)carbamoyl)-2-((7-fluoro-6-methoxynaphthalen-1-yl)oxy)-7-(methoxymethyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,13aS,14aR,16aS,Z)-14a-((cyclopropylsulfonyl)carbamoyl)-2-((7-fluoro-6-methoxynaphthalen-1-yl)oxy)-7-(methoxymethyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

tert-butyl ((2R,6S,7R,9S,13aS,14aR,16aS,Z)-14a-(((1-(fluoromethyl)cyclopropyl)sulfonyl)carbamoyl)-2-((3-isopropyl-7-methoxyquinoxalin-2-yl)oxy)-7-(methoxymethyl)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

tert-butyl ((2R,6S,7R,9R,13aS,14aR,16aS,Z)-14a-(((1-(fluoromethyl)cyclopropyl)sulfonyl)carbamoyl)-2-((3-isopropyl-7-methoxyquinoxalin-2-yl)oxy)-7-(methoxymethyl)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

tert-butyl ((2R,6S,7R,9R,13aS,14aR,16aS,Z)-14a-((cyclopropylsulfonyl)carbamoyl)-2-((7-fluoro-6-methoxynaphthalen-1-yl)oxy)-7-(methoxymethyl)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

tert-butyl ((2R,6S,7R,9S,13aS,14aR,16aS,Z)-2-((7-methoxy-3-(trifluoromethyl)quinoxalin-2-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

tert-butyl ((2R,6S,7R,9R,13aS,14aR,16aS,Z)-2-((7-methoxy-3-(trifluoromethyl)quinoxalin-2-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

tert-butyl ((2R,6S,7R,9S,13aS,14aR,16aS,Z)-2-((3-isopropyl-7-methoxyquinoxalin-2-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

tert-butyl ((2R,6S,7R,9R,13aS,14aR,16aS,Z)-2-((3-isopropyl-7-methoxyquinoxalin-2-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9S,13aS,14aR,16aS,Z)-2-((7-methoxy-3-(trifluoromethyl)quinoxalin-2-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9R,13aS,14aR,16aS,Z)-2-((7-methoxy-3-(trifluoromethyl)quinoxalin-2-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9S,13aS,14aR,16aS,Z)-2-((3-isopropyl-7-methoxyquinoxalin-2-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9R,13aS,14aR,16aS,Z)-2-((3-isopropyl-7-methoxyquinoxalin-2-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

tert-butyl ((2R,6S,7R,9R,13aS,14aR,16aS,Z)-14a-(((1-(fluoromethyl)cyclopropyl)sulfonyl)carbamoyl)-2-((7-methoxy-3-(trifluoromethyl)quinoxalin-2-yl)oxy)-7-(methoxymethyl)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

tert-butyl ((2R,6S,7R,9R,13aS,14aR,16aS,Z)-14a-(((1-(fluoromethyl)cyclopropyl)sulfonyl)carbamoyl)-2-(((3-isopropyl-7-methoxyquinoxalin-2-yl)oxy)-7-(methoxymethyl)-9-methyl-5,16-dioxo-1,2,3,5,6,7,8,9, 10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9R,13aS,14aR,16aS,Z)-14a-(((1-(fluoromethyl)cyclopropyl)sulfonyl)carbamoyl)-2-((7-methoxy-3-(trifluoromethyl)quinoxalin-2-yl)oxy)-7-(methoxymethyl)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9S,13aS,14aR,16aS,Z)-14a-(((1-(fluoromethyl)cyclopropyl)sulfonyl)carbamoyl)-2-((7-methoxy-3-(trifluoromethyl)quinoxalin-2-yl)oxy)-7-(methoxymethyl)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9R,13aS,14aR,16aS,Z)-14a-(((1-(fluoromethyl)cyclopropyl)sulfonyl)carbamoyl)-2-((3-isopropyl-7-methoxyquinoxalin-2-yl)oxy)-7-(methoxymethyl)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9S,13aS,14aR,16aS,Z)-14a-(((1-(fluoromethyl)cyclopropyl)sulfonyl)carbamoyl)-2-((3-isopropyl-7-methoxyquinoxalin-2-yl)oxy)-7-(methoxymethyl)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9R,13aS,14aR,16aS,Z)-14a-((cyclopropylsulfonyl)carbamoyl)-2-((7-methoxy-3-(trifluoromethyl)quinoxalin-2-yl)oxy)-7-(methoxymethyl)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9S,13aS,14aR,16aS,Z)-14a-((cyclopropylsulfonyl)carbamoyl)-2-((7-methoxy-3-(trifluoromethyl)quinoxalin-2-yl)oxy)-7-(methoxymethyl)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9R,13aS,14aR,16aS,Z)-2-((7-fluoro-4-methoxynaphthalen-1-yl)oxy)-7-(methoxymethyl)-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

tert-butyl ((2R,6S,7R,9S,13aS,14aR,16aS,Z)-2-((6-fluoro-7-methoxy-3-(trifluoromethyl)quinoxalin-2-yl)oxy)-7-(methoxymethyl)-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

tert-butyl ((2R,6S,7R,9R,13aS,14aR,16aS,Z)-2-((6-fluoro-7-methoxy-3-(trifluoromethyl)quinoxalin-2-yl)oxy)-7-(methoxymethyl)-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9S,13aS,14aR,16aS,Z)-2-((6-fluoro-7-methoxy-3-(trifluoromethyl)quinoxalin-2-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9R,13aS,14aR,16aS,Z)-2-((6-fluoro-7-methoxy-3-(trifluoromethyl)quinoxalin-2-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

tert-butyl ((2R,6S,7R,9S,13aS,14aR,16aS,Z)-2-((7-ethoxy-3-(trifluoromethyl)quinoxalin-2-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

tert-butyl ((2R,6S,7R,9R,13aS,14aR,16aS,Z)-2-((7-ethoxy-3-(trifluoromethyl)quinoxalin-2-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

3,3-difluoro-2-methylbutan-2-yl ((2R,6S,7R,9S,13aS,14aR,16aS,Z)-2-((7-ethoxy-3-(trifluoromethyl)quinoxalin-2-yl)oxy)-7-(methoxymethyl)-9-methyl-14a-(((l-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

3,3-difluoro-2-methylbutan-2-yl ((2R,6S,7R,9R,13aS,14aR,16aS,Z)-2-((7-ethoxy-3-(trifluoromethyl)quinoxalin-2-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9S,13aS,14aR,16aS,Z)-2-((7-ethoxy-3-(trifluoromethyl)quinoxalin-2-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9R,13aS,14aR,16aS,Z)-2-((7-ethoxy-3-(trifluoromethyl)quinoxalin-2-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

3,3-difluoro-2-methylbutan-2-yl ((2R,6S,7R,9S,13aS,14aR,16aS,Z)-2-((7-isopropoxy-3-(trifluoromethyl)quinoxalin-2-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

3,3-difluoro-2-methylbutan-2-yl ((2R,6S,7R,9R,13aS,14aR,16aS,Z)-2-((7-isopropoxy-3-(trifluoromethyl)quinoxalin-2-yl)oxy)-7-(methoxymethyl)-9-methyl-14a-(((1-methylcyclopropyl)sulfonyl)carbamoyl)-5, 16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9S,13aS,14aR,16aS,Z)-2-((7-isopropoxy-3-(trifluoromethyl)quinoxalin-2-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9R,13aS,14aR,16aS,Z)-2-((7-isopropoxy-3-(trifluoromethyl)quinoxalin-2-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9S,13aS,14aR,16aS,Z)-2-((4,5-dimethoxyquinazolin-2-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9R,13aS,14aR,16aS,Z)-2-((4,5-dimethoxyquinazolin-2-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

tert-butyl ((2R,6S,7R,9R,13aS,14aR,16aS,Z)-2-((4,5-dimethoxyquinazolin-2-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

3,3-difluoro-2-methylbutan-2-yl ((2R,6S,7R,9R,13aS,14aR,16aS,Z)-2-((4,5-dimethoxyquinazolin-2-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

tert-butyl ((2R,6S,7R,9S,13aS,14aR,16aS,Z)-2-((4-ethoxy-6-methoxyisoquinolin-1-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

tert-butyl ((2R,6S,7R,9R,13aS,14aR,16aS,Z)-2-((4-ethoxy-6-methoxyisoquinolin-1-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9S,13aS,14aR,16aS,Z)-2-((4-ethoxy-6-methoxyisoquinolin-1-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

1,1,1-trifluoro-2-methylpropan-2-yl ((2R,6S,7R,9R,13aS,14aR,16aS,Z)-2-((4-ethoxy-6-methoxyisoquinolin-1-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

3,3-difluoro-2-methylbutan-2-yl ((2R,6S,7R,9S,13aS,14aR,16aS,Z)-2-((4-ethoxy-6-methoxyisoquinolin-1-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; and 3,3-difluoro-2-methylbutan-2-yl ((2R,6S,7R,9R,13aS,14aR,16aS,Z)-2-((4-ethoxy-6-methoxyisoquinolin-1-yl)oxy)-7-(methoxymethyl)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;

or a pharmaceutically acceptable salt thereof.

10. A composition comprising a compound of claim 1, or a pharmaceutically acceptable salt thereof, and a pharmaceutically acceptable carrier.

11. The composition of claim 10 further comprising at least one additional compound having anti-HCV activity.

12. The composition of claim 11 wherein at least one of the additional compounds is an interferon or a ribavirin.

13. The composition of claim 12 wherein the interferon is selected from interferon alpha 2B, pegylated interferon alpha, consensus interferon, interferon alpha 2A, and lymphoblastoid interferon tau.

14. The composition of claim 11 wherein at least one of the additional compounds is selected from interleukin 2, interleukin 6, interleukin 12, Imiquimod, ribavirin, an inosine 5'-monophosphate dehydrogenase inhibitor, amantadine, and rimantadine.

15. The composition of claim 11 wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

16. A method of treating an HCV infection in a patient, comprising administering to the patient a therapeutically effective amount of a compound of claim 1, or a pharmaceutically acceptable salt thereof.

17. The method of claim 16 further comprising administering at least one additional compound having anti-HCV activity prior to, after, or simultaneously with the compound of formula (I), or a pharmaceutically acceptable salt thereof.

18. The method of claim 17 wherein at least one of the additional compounds is an interferon or a ribavirin.

19. The method of claim 18 wherein the interferon is selected from interferon alpha 2B, pegylated interferon alpha, consensus interferon, interferon alpha 2A, and lymphoblastoid interferon tau.

20. The method of claim 17 wherein at least one of the additional compounds is selected from interleukin 2, interleukin 6, interleukin 12, Imiquimod, ribavirin, an inosine 5'-monophosphate dehydrogenase inhibitor, amantadine, and rimantadine.

21. The method of claim 17 wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

* * * * *

UNITED STATES PATENT AND TRADEMARK OFFICE
CERTIFICATE OF CORRECTION

PATENT NO. : 9,580,463 B2
APPLICATION NO. : 14/768229
DATED : February 28, 2017
INVENTOR(S) : Nagalakshmi et al.

Page 1 of 1

It is certified that error appears in the above-identified patent and that said Letters Patent is hereby corrected as shown below:

In the Claims

Claim 8, Column 115, Lines 15-24:
Below " 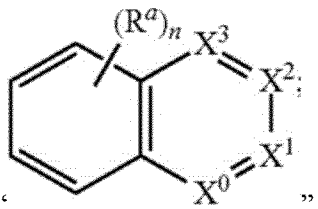 " delete "wherein".

Claim 9, Column 115, Line 63:
After "carbamate" insert -- ; --.

Signed and Sealed this
Twentieth Day of November, 2018

Andrei Iancu
*Director of the United States Patent and Trademark Office*